United States Patent
Jendralla et al.

(10) Patent No.: US 7,161,008 B2
(45) Date of Patent: Jan. 9, 2007

(54) OPTICALLY ACTIVE β-AMINOKETONES, OPTICALLY ACTIVE 1,3-AMINO ALCOHOLS AND PROCESSES FOR PREPARING THEM

(75) Inventors: Heiner Jendralla, Frankfurt (DE); Wilfried Schwab, Wiesbaden-Naurod (DE); Thomas Stuedemann, Kelkheim (DE)

(73) Assignee: Sanofi - Aventis Deutschland GmbH, Frankfurt (DE)

( * ) Notice: Subject to any disclaimer, the term of this patent is extended or adjusted under 35 U.S.C. 154(b) by 199 days.

(21) Appl. No.: 10/430,023

(22) Filed: May 5, 2003

(65) Prior Publication Data
US 2004/0030145 A1    Feb. 12, 2004

Related U.S. Application Data

(60) Provisional application No. 60/410,660, filed on Sep. 13, 2002.

(30) Foreign Application Priority Data
May 3, 2002    (DE)    ............................. 102 19 987

(51) Int. Cl.
C07D 213/36    (2006.01)
C07C 211/00    (2006.01)
(52) U.S. Cl. ..................... 546/264; 564/305
(58) Field of Classification Search ................ 514/342, 514/338; 546/269.7, 256, 267, 264; 564/305
See application file for complete search history.

(56) References Cited

U.S. PATENT DOCUMENTS

| | | | |
|---|---|---|---|
| 5,916,786 A | 6/1999 | Rozzell, Jr. | |
| 6,180,618 B1 * | 1/2001 | Stengelin et al. | ........... 514/176 |
| 6,245,744 B1 | 6/2001 | Frick | |
| 6,303,639 B1 * | 10/2001 | Frick et al. | ................. 514/342 |
| 6,566,340 B1 | 5/2003 | Frick | |
| 6,569,835 B1 | 5/2003 | Frick | |
| 6,596,728 B1 | 7/2003 | Kirsch et al. | |

FOREIGN PATENT DOCUMENTS

WO    WO 98/42643    10/1998

OTHER PUBLICATIONS

"Three-component carbon—carbon bond-forming reactions catalyzed by a Bronsted acid-surfactant -combined catalyst in water", Manable et. al., Tetrahedron 57 (2001)2537-2544.*
Akiyama, et al., HBF4 Catalyzed Mannich-Type Reaction in Aqueous Media, Synlett; 1999; No. 07; pp. 1045-1048.
Andrisano, et al., Stereochemistry of Mannich Bases—V: Lithium Aluminium Hydride Reduction of alpha-Asymmetric-beta-Amino Propiophenones and relative Configuration of the Corresponding Amino-Alcohols, Tetrahedron; 1970; 26; pp. 5247-5253.

Arend, et al., Modern Variants of the Mannich Reaction, Angew. Chem. Int. Ed.Engl.; 1998; 37; pp. 1045-1070.
Barluenga, et al., Diastereoselective Synthesis of gamma-Amino Alcohols with Three Chiral Centers by Reduction of beta-Amino Ketones and Derivatives, J. Org. Chem.; 1985; 50; pp. 4052-4056.
Brienne, et al., Reduction par l'hyrure de lithium et d'aluminium de beta-aminocetones, Bulletin de la Societe Chimique de France; 1969; 7; pp. 2395-2407.
Cicchi, et al., Synthesis of New Enantiopure gamma-aminoalcohols: their use as catalysts in the Alkylation of Benzaldehyde by Diethylzinc, Tetrahedron: Asymmetry; 1997; 8; 2; pp. 293-301.
Couturier, et al., Palladium Catalyzed Activation of Borane-amine Adducts: Rate Enhancement of Amine-borane Methanolysis in the Reduction of Nitrobenzenes to Anilines, Tetrahedron Letters; 2001; 42; pp. 2285-2288.
Denmark, et al., Catalytic Enantioselective Mannich-Type Reactions, Comprehensive Asymmetric Catalysis; Springer-Verlag:New York; 1999, vol. 2; Chapter 26.2.9; pp. 954-958.
Groger, et al., The Application of L-Proline as an Enzyme Mimic and Further New Asymmetric Using Small Organic Molecules as Chiral Catalysts, Agnew. Chem. Int. Ed.; 2001; 40; 3; pp. 529-532.
Ishitani, et al., Enantioselective Mannich-Type Reactions Using a Novel Chiral Zirconium Catalyst for the Synthesis of Optically Active beta-Amino Acid Derivatives, J. Am. Chem Soc.; 2000; 122, pp. 8180-8186.

(Continued)

*Primary Examiner*—Thomas Mckenzie
*Assistant Examiner*—Binta Robinson
(74) *Attorney, Agent, or Firm*—Jiang Lin

(57) ABSTRACT

The invention relates to chiral Mannich bases of formula (I), chiral 1,3-amino alcohols of formula (II) derived therefrom, wherein $R^1$, $R^2$, $R^3$, $R^4$ and $R^5$ are as defined herein, and to processes for preparing Mannich salts of formula (III) containing a chiral anion $Y^{*-}$ and compounds of formulae (I) and (II), wherein $R^1$, $R^2$, $R^3$, $R^4$, $R^5$ and $Y^{*-}$ are as defined herein.

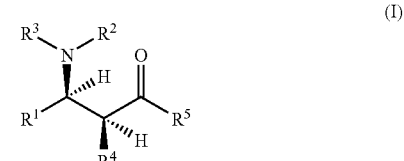

(I)

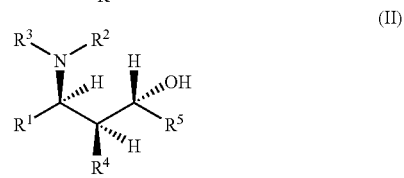

(II)

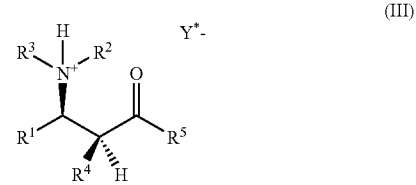

(III)

13 Claims, No Drawings

OTHER PUBLICATIONS

Jiang, et al., Highly Enantioselective Reduction of Achiral Ketones with NaBH4/Me3SiCl Catalyzed by (S)-alpha,alpha-diphenylpyrrolidinemethanol, tetrahedron Letters; 2000; 41; pp. 10281-10283.

List, Benjamin, The Direct Catalytic Asymmetric Three-Component Mannich Reaction, J. AM. Chem. Soc.; 2000; 122; pp. 9336-9337.

Nolen, et al., Diastereoselectivity in the Synthesis of Mannich Bases, Tetrahedron Letters; 1991; 32; 1; pp. 73-74.

Shida, et al., Nickel Catalyzed Imine Aldol Reactions between Activated Imines and Pronucleophiles, Tetrahedron Letters; 1995; 36; 28; pp. 5023-5026.

Yamasaki, et al., Direct catlylic Asymmetric Mannich-type Reaction of Unmodified Ketones utilizing the Cooperation of an AlLibis(binaphthoxide Complex and La(OTf)3.nH2O, Tetrahedron Letters; 40; 1999; pp. 307-310.

Akiyama, et al., HBF4 Catalyzed Mannich-Type Reaction in Aqueous Media, Synlett; 1999; No. 07; pp. 1045-1048.

Andrisano, et al., Stereochemistry of Mannich Bases—V: Lithium Aluminum Hydride Reduction of alpha-Asymmetric-beta-Amino Propiophenones and relative Configuration of the Corresponding Amino-Alcohols, Tetrahedron; 1970; 26; pp. 5247-5253.

Arend, et al., Modern Variants of the Mannich Reaction, Angew. Chem. Int. Ed.Engl.; 1998; 37; pp. 1045-1070.

Barluenga, et al., Diastereoselective Synthesis of gamma-Amino Alcohols with Three Chiral Centers by Reduction of beta-Amino Ketones and Derivatives, J. Org. Chem.; 1985; 50; pp. 4052-4056.

Brienne, et al., Reduction par l'hyrure de lithium el d'aluminium de beta-aminocetones, Bulletin de la Societe Chimique de France; 1969; 7: pp. 2395-2407.

Cicchi, et al., Synthesis of New Enantiopure gamma-aminoalcohols: their use as catalysts in the Alkylation of Benzaldehyde by Diethylzinc, Tetrahedron: Asymmetry; 1997; 8; 2; pp. 293-301.

Couturier, et al., Palladium Catalyzed Activation of Borane-amine Adducts: Rate Enhancement of Amine-borane Methanolysis in the Reduction of Nitrobenzenes to Anilines, Tetrahedron Letters; 2001; 42; pp. 2285-2288.

Denmark, et al., Catalytic Enantioselective Mannich-Type Reactions, Comprehensive Asymmetric Catalysis; Springer-Verlag:New York; 1999, vol. 2; Chapter 26.2.9; pp. 954-958.

Groger, et al., The Application of L-Proline as an Enzyme Mimic and Further New Asymmetric Using Small Organic Molecules as Chiral Catalysts, Agnew. Chem. Int. Ed.;2001; 40; 3; pp. 529-532.

Ishitani, et al., Enantioselective Mannich-Type Reactions Using a Novel Chiral Zirconium Catalyst for the Synthesis of Optically Active beta-Amino Acid Derivatives, J. Am. Chem Soc.; 2000; 122, pp. 8180-8186.

Jiang, et al., Highly Enantioselective Reduction of Achiral Ketones with NaBH4/Me3SiCl Catalyzed by(S)-alpha, alpha-diphenylpyrrolidinemethanol, tetrahedron Letters; 2000; 41; pp. 10281-10283.

List, Benjamin, The Direct Catalytic Asymmetric Three-Component Mannich Reaction, J. AM. Chem. Soc.; 2000; 122; pp. 9336-9337.

Nolen, et al., Diastereoselectivity in the Synthesis of Mannich Bases, Tetrahedron Letters; 1991; 32; 1; pp. 73-74.

Shida, et al., Nickel Catalyzed Imine Aldol Reactions between Activated Imines and Pronucleophiles, Tetrahedron Letters; 1995; 36; 28; pp. 5023-5026.

Yamasaki, et al., Direct catlylic Asymmetric Mannich-type Reaction of Unmodified Ketones utilizing the Cooperation of an AlLibis(binaphthoxide Complex and La(OTf)3.nH2O, Tetrahedron Letters; 40; 1999; pp. 307-310.

Akiyama, et al, HBF4 Catalyzed Mannich-Type Reaction in Aqueous Media, Synlett; 1999; No. 07; pp. 1045-1048.

Andrisano, et al., Stereochemistry of Mannich Bases—V: Lithium Aluminum Hydride Reduction of alpha-Asymmetric-beta-Amino Propiophenones and relative Configuration of the Corresponding Amino-Alcohols, Tetrahedron; 1970; 26; pp. 5247-5253.

Arend, et al., Modern Variants of the Mannich Reaction, Angew. Chem. Int. Ed.Engl.; 1998; 37; pp. 1045-1070.

Barluenga, et al., Diastereoselective Synthesis of gamma-Amino Alcohols with Three Chiral Centers by Reduction of beta-Amino Ketones and Derivatives, J. Org. Chem.; 1985; 50; pp. 4052-4056.

Brienne, et al., Reduction par l'hyrure de lithium et d'aluminium de beta-aminocetones, Bulletin de la Societe Chimique de France; 1969; 7: pp. 2395-2407.

Cicchi, et al., Synthesis of New Enantiopure gamma-aminoalcohols: their use as catalysts in the Alkylation of Benzaldehyde by Diethylzinc, Tetrahedron: Asymmetry; 1997; 8; 2; pp. 293-301.

Couturier, et al., Palladium Catalyzed Activation of Borane-amine Adducts: Rate Enhancement of Amine-borane Methanolysis in the Reduction of Nitrobenzenes to Anilines, Tetrahedron Letters; 2001; 42; pp. 2285-2288.

Denmark, et al., Catalytic Enantioselective Mannich-Type Reactions, Comprehensive Asymmetric Catalysis; Springer-Verlag:New York; 1999, vol. 2; Chapter 26.2.9; pp. 954-958.

Groger, et al., The Application of L-Proline as an Enzyme Mimic and Further New Asymmetric Using Small Organic Molecules as Chiral Catalysts, Agnew. Chem. Int. Ed.; 2001; 40; 3; pp. 529-532.

Ishitani, et al., Enantioselective Mannich-Type Reactions Using a Novel Chiral Zirconium Catalyst for the Synthesis of Optically Active beta-Amino Acid Derivatives, J. Am. Chem Soc.; 2000; 122, pp. 8180-8186.

Jiang, et al., Highly Enantioselective Reduction of Achiral Ketones with NaBH4/Me3SiCl Catalyzed by (S)-alpha,alpha-diphenylpyrrolidinemethanol, tetrahedron Letters; 2000; 41; pp. 10281-10283.

List, Benjamin, The Direct Catalytic Asymmetric Three-Component Mannich Reaction, J. AM. Chem. Soc.; 2000; 122; pp. 9336-9337.

Nolen, et al., Diastereoselectivity in the Synthesis of Mannich Bases, Tetrahedron Letters; 1991; 32; 1; pp. 73-74.

Shida, et al., Nickel Catalyzed Imine Aldol Reactions between Activated Imines and Pronucleophiles, Tetrahedron Letters; 1995; 36; 28; pp. 5023-5026.

Yamasaki, et al., Direct catlytic Asymmetric Mannich-type Reactions of Unmodified Ketones utilizing the Cooperation of an AlLibis(binaphthoxide Complex and La(OTf)3.nH2O, Tetrahedron Letters; 40; 1999; pp. 307-310.

* cited by examiner

OPTICALLY ACTIVE β-AMINOKETONES, OPTICALLY ACTIVE 1,3-AMINO ALCOHOLS AND PROCESSES FOR PREPARING THEM

FIELD OF THE INVENTION

The invention relates to optically active β-aminoketones and optically active 1,3-amino alcohols. The invention further relates to processes for preparing these compounds.

BACKGROUND OF THE INVENTION

Aminoalkylations of CH-acidic compounds have been known for about 100 years. They are referred to as Mannich reactions and are one of the most important C—C bond forming reactions of organic chemistry.

Although silyl enol ethers having certain other silyl groups are more stable, they are more expensive to prepare. The high nucleophilicity of the preformed enolate equivalents has advantages and disadvantages. On the one hand, it allows frequently mild reaction conditions and thus occasionally makes possible Mannich reactions that in the direct variant are accompanied by too many secondary reactions. On the other hand, the aminomethylations of preformed enolate equivalents are frequently low temperature reactions and therefore costly and inconvenient on the industrial scale. Further disadvantages of stereoselective variants using preformed enolate equivalents are the use of industrially problematic Lewis acid catalysts, poor solubilities of reaction components at the low temperature and, for this reason, the necessity of using large amounts of solvent (poor space/time yields) or the use of problematic or expensive solvents.

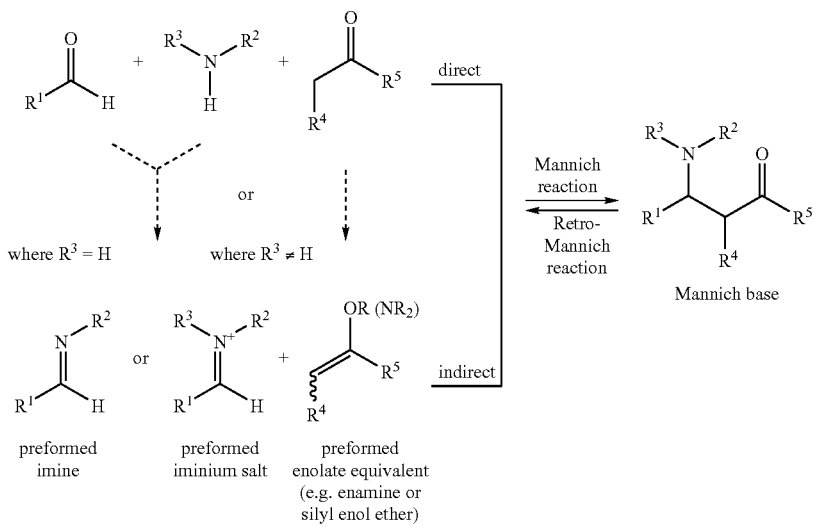

In its original and most well-known form, the Mannich reaction is carried out with three reactants in the form of a "three-component coupling": an enolizable ketone, a non-enolizable aldehyde (frequently formaldehyde or an arylaldehyde) and an amine component (ammonia or a primary or secondary amine) react with one another to form a β-aminoketone. In this "Mannich base" the active hydrogen of the enolizable ketone has been replaced by an aminoalkyl substituent. This direct variant of the Mannich reaction is particularly industrially attractive, because the three reactants specified are usually readily available and inexpensive, and at least very easily obtainable. Also, these reactants are generally not sensitive (i.e., have good storability) and therefore allow simple handling. Finally, the direct three-component coupling of commercially available reactants is a single-stage, i.e., the shortest conceivable, synthesis of β-aminoketones.

In addition, there are less industrially attractive indirect variants of the Mannich reaction in which preformed enolate equivalents (usually enamines or silyl enol ethers) are used. These compounds are generally not commercially available or are expensive. Their preceding preparation is an additional synthetic step. Also, the trimethylsilyl enol ethers in particular and, to a lesser extent, the enamines are acid- and hydrolysis-sensitive, poorly storable and difficult to handle.

Iminium salts in the Mannich reaction are distinctly more reactive (more electrophilic) than imines. This brings advantages and disadvantages that are similar to those described above for preformed enol equivalents.

Asymmetric Mannich reactions are described, for example, in M. Arend et al. (Angew. Chem. Int. Ed. Engl. 1998, 37, 1045–1070), which states on page 1067: "Despite many studies, and some notable successes, penetration into enantiomerically pure Mannich bases is still only beginning. [ . . . ] When one thinks of the many in situ racemization-free routes to derivatization of the kinetic products (to, for example, amino alcohols, diamines, amines etc.), it becomes understandable that the possibility of developing efficient and effective routes to products of controlled absolute configuration may indeed be realizable. Catalytic processes, which are established in many other areas of stereochemisty, are almost completely untouched".

The use of stoichiometric amounts of chiral auxiliaries in an asymmetric Mannich reaction is described, for example, by H. Ishitani et al. (J. Am. Chem. Soc. 2000, 122, 8180–8186). This method has no industrial relevance, since the chiral auxiliary is covalently bonded to the preformed imine (or more rarely to the preformed enolate equivalent), in order to conduct the Mannich reaction as a diastereoselective addition. Synthesis, linking and, after completed Mannich reaction, removal of the chiral auxiliary require a plurality of additional synthetic steps. The Mannich additions were in addition frequently low temperature reactions, and the chiral auxiliaries were difficult to obtain or only available in an absolute configuration.

Catalytic asymmetric Mannich variants were summarized by S. E. Denmark & O. J.-C. Nicaise ("Catalytic Enantioselective Mannich-Type Reactions" in Comprehensive Asymmetric Catalysis, E. N. Jacobsen, A. Pfaltz, H. Yamamoto, Eds.; Springer-Verlag: New York, 1999; Vol. 2, Chapter 26.2.9; pages 954–958). The catalytic variants are for the most part indirect Mannich reactions that limits their industrial attractiveness. Also, complicated chiral transition metal catalysts have to be used.

Direct asymmetric three-component Mannich reactions using unmodified ketones can be induced by heteropolymetallic chiral catalysts based on lanthanides, although, as described in S. Yamasaki et al. (Tetrahedron Lett. 1999, 40, 307–310), result in only moderate chemical yields ($\leq 16\%$) and enantiomeric excesses (<64% ee).

The first direct catalytic asymmetric three-component Mannich reaction which comes near to fulfilling the industrial demands was reported only recently (B. List, J. Am. Chem. Soc. 2000, 122, 9336–9337; cf. H. Gröger & J. Wilken, Angew. Chem. Int. Ed. Engl. 2001, 40, 529–532). In this reaction, unmodified ketones are reacted with aryl- or alkylaldehydes and certain aniline derivatives with catalysis using 35 mol % of (L)-proline in dimethyl sulfoxide or chloroform at room temperature to give optically active Mannich bases. The chemical yields were moderate to good (35–90%), and the optical purities average to very good (73–96% ee).

Mannich bases and their derivatives have numerous industrial applications that are summarized in M. Arend et al. (Angew. Chem. Int. Ed. Engl. 1998, 37, 1044–1070) on page 1045. The most important field of use, in particular of chiral Mannich bases, is the preparation of active ingredients for drugs, for example the neuroleptic Moban. On this subject, it is stated in Arend et al. on page 1047: "The classical Mannich reaction is not suited to the enantioselective synthesis of β-amino ketones and amino aldehydes. Thus, the majority of pharmaceutical products, which are derived from the Mannich reaction, are used in the form of racemates. The application of enantiomerically pure Mannich bases is only possible when these are available by separation of the racemate. This problem becomes more severe when one takes into consideration the increasing importance of stereochemically pure pharmaceuticals (the avoidance of "isomer ballast" and of undesirable side effects)."

Racemic β-aminoketones that can be described by a mixture of a compound of formula (A) and its enantiomer

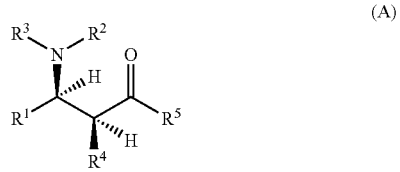

(A)

wherein $R^1$ is phenyl, $R^2$ is H, $R^3$ is phenyl, $R^4$ is methyl and $R^5$ is phenyl, are described in T. Akiyama et al., Synlett 1999, 1045–1048;

wherein $R^1$ is p-tolyl, $R^2$ is H, $R^3$ is p-methoxycarbonylphenyl, $R^4$ is methyl and $R^5$ is phenyl are described in N. Shida et al, Tetrahedron Left. 1995, 36, 5023–5026;

wherein $R^1$ is phenyl, $R^2$ is H, $R^3$ is p-chlorophenyl, $R^4$ is methyl and $R^5$ is phenyl are described in CA120: 257988; and wherein $R^1$ is tert-butyl or phenyl, $R^2$ is $R^3$ is $R^4$ is methyl and $R^5$ is phenyl are described in E. G., Nolen et al., Tetrahedron Lett. 1991, 32, 73–74.

Chiral 1,3-amino alcohols, like, for example, the analgesic tramadol, are important as active pharmaceutical ingredients, and also as chiral auxiliaries for asymmetric syntheses, documented, for example, in S. Cicchi et al. ("Synthesis of new enantiopure β-amino alcohols: their use as catalysts in the alkylation of benzaldehyde by diethylzinc", Tetrahedron: Asymmetry 1997, 8, 293–301).

The limited diastereoselective reduction of Mannich bases with $LiAlH_4$ was described as early as 1985 by J. Barluenga et al. ("Diastereoselective synthesis of β-amino alcohols with three chiral centers by reduction of β-amino ketones and derivatives" J. Org. Chem. 1985, 50, 4052–4056).

A multistage enzymatic method for producing chiral 1,3-amino alcohols starting from racemic butane-1,4-diols is described in the U.S. Pat. No. 5,916,786.

The carbonyl reduction of α-chiral β-aminoketones using $LiAlH_4$ (lithium aluminum hydride) or with hydrogen in the presence of platinum catalysts results preferentially in the 1,3-amino alcohol dia-(B) whose hydroxy configuration is diastereomeric to formula (B) when the amino substituent is tertiary

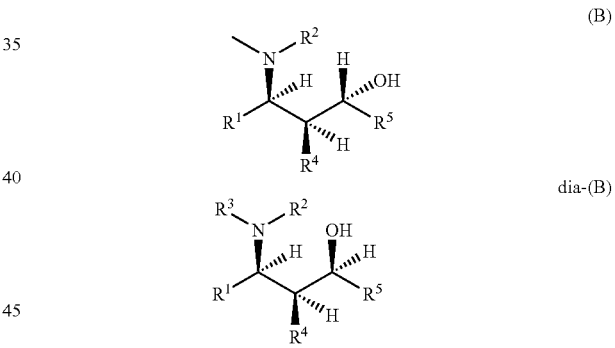

(B)

dia-(B)

and an approximately equimolar mixture of the diastereomers (B) and dia-(B) results when the amino substituent is secondary (M.-J. Brienne et al., Bull. Soc. Chim. France 1969, 2395; A. Andrisano & L. Angiolini Tetrahedron 1970, 26, 5247).

Chiral 1,3-amino alcohols of formula (B) could hitherto not be prepared with industrially usable diastereoselectivities from Mannich bases of formula (A).

The patent application EP 1117645 (published as WO 00/20392) describes optically active 1,3-amino alcohols of formula (B) wherein $R^1$ is o-aminophenyl, $R^2$ is H, $R^3$ is 2-pyridyl, $R^4$ is 2-pyridyl and $R^5$ is phenyl or 3,5-dimethylisoxazol-4-yl that had previously been prepared by a classical optical resolution, and are useful as intermediate in the synthesis of are bile acid re-absorption inhibitors for the treatment of obesity and disorders of lipid metabolism. The compound of the formula (B) can be used in the synthesis of the compounds as described in Table 1 of WO 00/20392, e.g., the compound of the formula

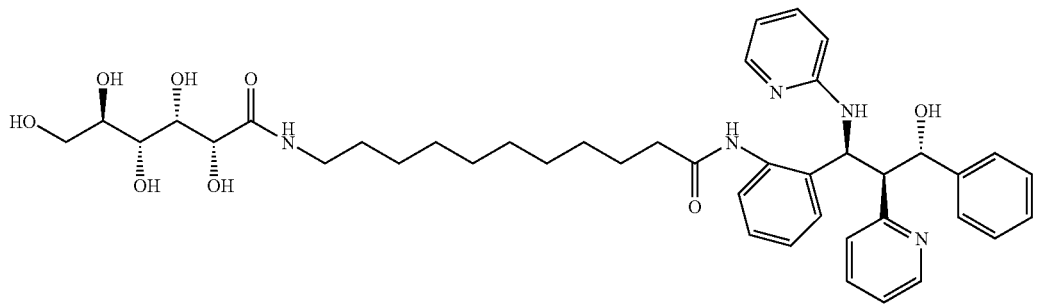

as described In Example 9.

SUMMARY OF THE INVENTION

The present invention relates to a compound of formula (I) or its enantiomer

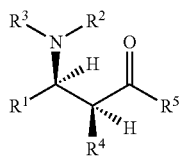
(I)

wherein
R¹ is hydrogen;
  tert-butyl; or
  aryl or heteroaryl;
R², R³ and R⁴ are each, independently,
  hydrogen;
  $(C_1-C_7)$alkyl, optionally substituted by aryl;
  $(C_3-C_7)$cycloalkyl; or
  aryl or heteroaryl;
and
R⁵ is aryl or heteroaryl;

provided that
  R¹ as o-nitrophenyl;
  R² as hydrogen;
  R³ as 2-pyridyl;
  R⁴ as 2-pyridyl; and
  R⁵ as phenyl or 3,5-dimethylisoxazol-4-yl,
are not currently present.

The invention also relates to a compound of formula (II),

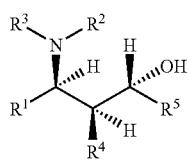
(II)

wherein
R¹ is hydrogen;
  tert-butyl; or
  aryl or heteroaryl;
R², R³ and R⁴ are each, independently,
  hydrogen;
  $(C_1-C_7)$alkyl, optionally substituted by aryl;
  $(C_3-C_7)$cycloalkyl; or
  aryl or heteroaryl;
and
R⁵ is aryl or heteroaryl;

or its enantiomer or a salt of the compound of formula (II) or a salt of the enantiomer.

The present invention also relates to a process for preparing a compound of formula (III) or its diastereoisomer (III A),

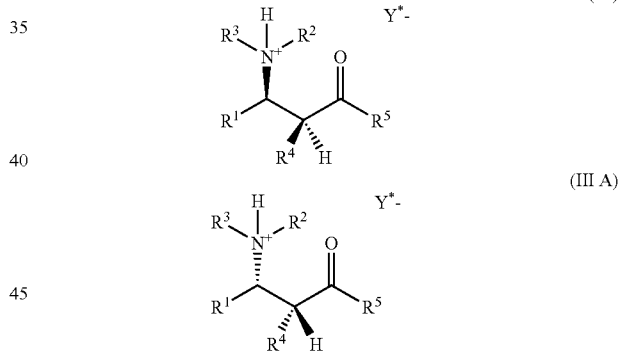

wherein
R¹ is hydrogen;
  tert-butyl; or
  aryl or heteroaryl;
R², R³ and R⁴ are each, independently,
  hydrogen;
  $(C_1-C_7)$alkyl, optionally substituted by aryl;
  $(C_3-C_7)$cycloalkyl; or
  aryl or heteroaryl;
R⁵ is aryl or heteroaryl;
and
Y*⁻ is the conjugate base of an optically active organic Brønsted acid, comprising reacting compounds of formulae (IV), (V), (VI) and (VII)

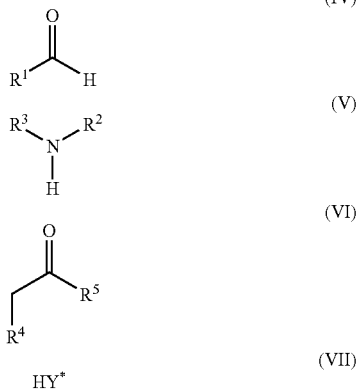

(IV), (V), (VI), (VII)

wherein $R^1$, $R^2$, $R^3$, $R^4$, $R^5$ and $Y^{*-}$ are as defined above, without a solvent or in one or more suitable solvents, by
(i) simultaneously in a direct Mannich reaction, or
(ii) sequentially wherein initially the compounds of formulae (IV) and (V) are reacted to give an imine of formula (X) or to an aminal of formula (XI) that is optionally isolated

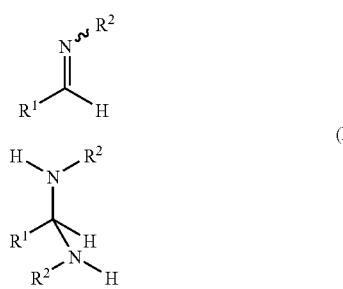

(X), (XI)

and then reacting the compound of formula (X) or (XI) with the compounds of formula (VI) and (VII).

The above-described reaction to give a compound of formula (III) is referred to hereinbelow as process step 1.

It was found that, surprisingly, a compound of formula (III) or its diastereoisomer (III A), or salt of the compound of formula (I), whose cation has very high enantiomeric excess and very high diastereomeric purity (syn/anti ratio), can be prepared in high yield in a simple manner by the above-described process step 1.

The cation of (III A) is the enantiomer of the cation (III). However, since the anion $Y^{*-}$ is homochiral, the compound (III A) is a diastereoisomer to the compound (III).

DETAILED DESCRIPTION OF THE INVENTION

Definition of Terms

As used above, and throughout the description of the invention, the following terms, unless otherwise indicated, shall be understood to have the following meanings.

Alkyl and alkoxy may be branched or unbranched.

Examples of $(C_1-C_7)$alkyl include methyl, ethyl, propyl, isopropyl, n-butyl, isobutyl, tert-butyl, pentyl, isopentyl, neopentyl, hexyl, and heptyl.

Examples of $(C_3-C_7)$cycloalkyl include cyclopropyl, cyclobutyl, cyclopentyl, cyclohexyl, cycloheptyl, 2-methylcyclopentyl, and 3-methylcyclohexyl.

Aryl is a carbocyclic aromatic having 5–14 carbon atoms, optionally substituted 1 to 5 times by substituents. A preferred aryl has 6–10 carbon atoms. More preferred aryl is phenyl, naphthyl, anthracenyl or phenanthrenyl. Particularly preferred aryl is phenyl or naphthyl.

Heteroaryl is a heterocyclic aromatic having 5–14 carbon atoms wherein 1 to 4 of the carbon atoms are replaced by N, O or S, optionally substituted 1 to 5 times by substituents. A preferred heteroaryl has 6–10 carbon atoms wherein 1 to 4 of the carbon atoms are replaced by N, O or S. More preferred heteroaryl is pyridyl, quinolinyl, isoquinolinyl, benzoquinolinyl, pyridazinyl, pyrimidinyl, pyrazinyl, triazinyl, tetrazinyl, benzopyridazinyl, benzopyrimidinyl, benzopyrazinyl (quinoxalinyl), benzotriazinyl, pyridopyridinyl, pyridoquinolinyl (phenanthrolinyl), benzoquinoxalinyl (phenazinyl), pyrrolyl, benzopyrrolyl (indolyl), benzoindolyl, pyrazolyl, benzopyrazolyl, imidazolyl, benzimidazolyl, triazolyl, benzotriazolyl, tetrazolyl, imidazopyrimidinyl (9H-purinyl), furanyl, benzofuranyl, dibenzofuranyl, thiophene, benzothiophene, dibenzothiophene, isoxazolyl, benzisoxazolyl, oxazolyl, benzoxazolyl, oxadiazolyl, benzoxadiazolyl, thiazolyl, benzothiazolyl, isothiazolyl, benzisothiazolyl, thiadiazolyl or benzothiadiazolyl. Particularly preferred heteroaryl is pyridyl, quinolinyl, isoquinolinyl or benzoquinolinyl.

Especially preferred heteroaryl is pyridyl or quinolinyl.

Substituents for aryl or heteroaryl are $(C_1-C_7)$alkyl, $(C_3-C_7)$cycloalkyl, alkanoyl $((C_1-C_7)$alkyl-CO—), aroyl (aryl-CO—), heteroaroyl (heteroaryl-CO—), fluoro, chloro, bromo, iodo, hydroxy, $(C_1-C_7)$alkoxy, $(C_3-C_7)$cycloalkoxy, aryloxy, heteroaryloxy, $(C_1-C_7)$alkanoyloxy, aroyloxy, heteroaroyloxy, NHR—CO—O—, NRR'—CO—O—, RO—CO—O—, RS—CO—O—, NHR—CS—O—, NRR'—CS—O—, RO—CS—O—, RS—CS—O—, $(C_1-C_7)$alkyl-SO$_2$—O—aryl-SO$_2$—O—, heteroaryl-SO$_2$—O—, nitro, R—CO—NH—, R—CO—NR'—, RO—CO—NH—, RO—CO—NR'—, NHR—CO—NH—, NHR—CO—NR'—, NRR''—CO—NR'—, di($C_1-C_7$)alkylamino, diarylamino, diheteroarylamino, amino-aryl-N—($C_1-C_7$)alkyl-N—, amino-heteroaryl-N—($C_1-C_7$)alkyl-N—, $(C_1-C_7)$alkylthio, arylthio, heteroarylthio, $(C_1-C_7)$alkylsulfonyl, arylsulfonyl, heteroarylsulfonyl, arylsulfoxidyl, heteroarylsulfoxidy, an unsubstituted aryl or heteroaryl, wherein R, R' and R'' are each, independently, (C1–C7)alkyl, (C3–C7)cycloalkyl, aryl or heteroaryl. Preferred substituents are $(C_1-C_7)$alkyl, $(C_3-C_7)$cycloalkyl, fluoro, chloro, bromo, $(C_1-C_7)$alkoxy, $(C_3-C_7)$cycloalkoxy, aryloxy, heteroaryloxy, $(C_1-C_7)$alkanoyloxy, aroyloxy, heteroaroyloxy, NHR—CO—O—, NRR'—CO—O—, RO—CO—O—, nitro, phenyl, naphthyl, pyridyl, quinolinyl, isoquinolinyl, benzoquinolinyl.

Especially preferred substituents are nitro, fluoro, chloro or bromo.

Brønsted acid is a protic acid, preferably an optically active, naturally occurring or industrially prepared carboxylic acid, an optically active sulfonic acid, an optically active phosphoric acid, phosphinic acid or phosphonic acid derivative, or an optically active phenol.

Examples of optically active, naturally occurring or industrially prepared carboxylic acid are (R)-(−)-mandelic acid, (S)-(+)-mandelic acid, D-(−)-tartaric acid, L-(+)-tartaric acid, (+)-di-O,O'-pivaloyl-D-tartaric acid [(+)-DPTA], (−)-di-O,O'-pivaloyl-L-tartaric acid, [(−)-DPTA], (+)-O,O'-dibenzoyl-D-tartaric acid, (−)—O,O'-dibenzoyl-L-tartaric acid, (−)-di-O,O'-benzoyl-L-tartaric mono(dimethylamide), (+)-O,O'-dianisoyl-D-tartaric acid [(+)-DATA], (−)-O,O'-dianisoyl-L-tartaric acid [(−)-DATA], (+)-di-O,O'-p-tolyl-D-tartaric acid, (−)-di-O,O'-p-tolyl-L-tartaric acid, D-(+)-malic acid, L-(−)-malic acid, L-(+)-lactic acid, D-(−)-lactic acid, (S)-(−)-2-(phenylaminocarbonyloxy)propionic acid, (R)-(+)-2-(phenylaminocarbonyloxy)propionic acid, D-(+)-gluconic acid, (−)-2,3,4,6-di-O-isopropylidene-2-keto-L-gulonic acid, (D)-(−)-quinic acid, (−)-3,4,5-trihydroxy-1-cyclohexene-1-carboxylic acid [shikimic acid], (S)-(+)-(2, 2-dimethyl-5-oxodioxolan-4-yl)acetic acid, (+)-camphoric acid, (−)-camphoric acid, (1R)-(+)-camphanic acid, (1S)-(−)-camphanic acid, (R)-(−)-O-acetylmandelic acid, (S)-(+)—O-acetylmandelic acid, (R)-2-phenoxypropionic acid, (S)-2-phenoxypropionic acid, (S)-(+)-α-methoxyphenylacetic acid, (R)-(−)-α-methoxyphenylacetic acid, (R)-(+)-α-methoxy-α-trifluoromethylphenylacetic acid, (S)-(−)-α-methoxy-α-trifluoromethylphenylacetic acid, (S)-(+)-2-phenylpropionic acid, (R)-(−)-2-phenylpropionic acid, (R)-(+)-2-chloropropionic acid, (S)-(−)-2-chloropropionic acid, (R)-(+)-N-(α-methylbenzyl)phthalic monoamide, (S)-(−)-N-(α-methylbenzyl)phthalic monoamide, (R)-(−)-5-oxotetrahydrofuran-2-carboxylic acid, (S)-(+)-5-oxotetrahydrofuran-2-carboxylic acid, D-(+)-3-phenyllactic acid, L-(−)-3-phenyllactic acid, L-(+)-α-hydroxyisovaleric acid, D-(−)-α-hydroxyisovaleric acid, (+)-menthyloxyacetic acid, (−)-menthyloxyacetic acid, (+)-mono-(1S)-menthyl phthalate, (−)-mono-(1R)-menthyl phthalate, (+)-trans-5-norbornene-2,3-dicarboxylic acid, (−)-trans-5-norbornene-2,3-dicarboxylic acid, (R)-(+)-methylsuccinic acid, (S)-(−)-methylsuccinic acid, (R)-(+)-6-hydroxy-2,5,7,8-tetramethylchroman-2-carboxylic acid [(R)-(+)-Trolox®], (S)-(−)-6-hydroxy-2,5,7,8-tetramethylchroman-2-carboxylic acid [(S)-(−)-Trolox®], (S)-(+)-2-(4-isobutylphenyl)propionic acid [(S)-ibuprofen], (R)-(−)-2-(4-isobutylphenyl) propionic acid [(R)-ibuprofen], (+)-2-(6-methoxy-2-naphthyl)propionic acid [(+)-naproxen], (−)-2-(6-methoxy-2-naphthyl)propionic acid [(−)-naproxen], and natural or unnatural α- or β-amino acids and their readily accessible derivatives, in particular N-acylated derivatives.

Examples of optically active sulfonic acids include (1S)-(+)-camphor-10-sulfonic acid, (1R)-(−)-camphor-10-sulfonic acid, (−)-3-bromocamphor-8-sulfonic acid and (+)-3-bromocamphor-10-sulfonic acid.

Examples of optically active phosphoric acids, phosphinic acids or phosphonic acid derivatives include (R)-(−)-1,1'-binaphthalene-2,2'-diyl hydrogen phosphate, (S)-(+)-1,1'-binaphthalene-2,2'-diyl hydrogenphosphate, (+)-phosphinothricin and (−)-phosphinothricin.

Examples of optically active phenols include (R)-(+)- and (S)-(−)-binaphthol. The R and S nomenclature follows Cahn, Ingold and Prelog priority rules. The priority of the chiral centers can however change when one or more substituents are modified. The term (SR,RS,SR) means that in said compound of the stereocentre in the middle has R-configuration when the two remaining centers have S-configuration (which is the configuration for the compound of formula (II) as shown above)—or that the middle center has S-configuration and the two remaining are R-configured (which is the "mirrored" enantiomer of the configuration as shown above). The configuration of the stereoisomer depends on the choice of the chiral anion Y*−. The term (SR,RS,SR) as used above refers to the exemplified compounds of the present invention, but may be changed for different compounds or substituents. The stereochemistry of the compound of formula (II) is unambiguously determined by the structural formula as shown above.

Particular or Preferred Embodiment

A particular embodiment of the compound of formula (I) is wherein:

$R^1$ as phenyl substituted by one nitro group;

$R^2$ as hydrogen;

$R^3$ as 2-pyridyl, optionally substituted once by methyl, fluorine or methyoxy;

$R^4$ as 2-pyridyl, optionally substituted once by hydroxy or methoxy; and $R^5$ as optionally substituted phenyl or heterocyclic aryl are not concurrently present.

Over the entire application text, any stereochemical formula given refers either to the absolute configuration expressed by the stereochemical formula or its enantiomer, where the compounds are always present in an enantiomeric purity of greater than or equal to 90% ee, preferably greater than or equal to 95% ee, more preferably greater than or equal to 98% ee. This applies in particular to the compounds of formulae (I), (II) and (III).

Over the entire application text, a "classical optical resolution" is the separation of the enantiomers of a racemic material by using a (substantially) enantiomerically pure auxiliary to form diastereomeric salts which, owing to differing physical properties, for example different solubilities, are separated from one another without resulting in a (significant) conversion of one enantiomer to the other under the conditions of the optical resolution. The maximum achievable yield of the enantiomerically pure material by means of a classical optical resolution is 50%. It differs fundamentally from the "dynamic optical cleavage" in which the enantiomers interconvert under the conditions of the optical resolution and thus enable yields of the enantiomerically pure material of up to 100% to be achieved. Dynamic optical resolutions may in principle be kinetically controlled or thermodynamically controlled. A group of reactions within the thermodynamically controlled dynamic optical resolutions are the crystallization-induced dynamic optical resolutions. The examples described in the present invention belong to this group of reactions.

In a preferred embodiment of the process step 1, the four components of formulae (IV), (V), (VI) and (VII) and optionally a suitable solvent are introduced into a reactor and stirred. The sequence of addition is uncritical. On a large scale, in particular when (IV)–(VII) are solids, it is most practicable to initially charge these reactants in the reactor and then to feed in the solvent, if necessary with cooling. The reaction mixture is then heated to the desired reaction temperature. In the normal embodiment, a solution is initially present. However, in particular when one or more of the four components is sparingly soluble, the process step may also be carried out in such a way that the sparingly soluble reactants only go into solution as the reaction advances. Owing to the crystallization of the salts (III) and (III A) that sets in after a certain time, the latter case may result in a suspension being present over the entire course of the reaction.

When the solution of the reactants (IV)–(VII) is initially clear and a sample is taken from the reaction mixture immediately after the crystallization of the salts (III)/(III A), and this sample is filtered, the analysis shows that there is a small to moderate, but significant excess of the salt (III) over the diastereomeric salt (III A) in the precipitate. In contrast, the salts (III) and (III A) are present in the filtrate in a ratio of 1:1. In the further course of the reaction, the amount of precipitate increases continuously and the ratio of (III) to (III A) rises continuously, while it remains in the filtrate at 1:1.

Finally, the reaction changes to a steady state in which neither the amount of precipitate nor the ratio of (III) to (III A) rises further. The amount of precipitate was generally 85–95% of theory and the enantiomeric excess of the Mannich base (I) in the (III)/(III A) precipitate was 90–99% ee.

Owing to the retro-Mannich tendency of (III) and (III A), it is generally not possible to determine the enantiomeric ratio by direct HPLC or DC analysis. Although determination by NMR is possible in principle, it is too inexact owing to signal overlapping. The best determination method is to derivative the samples with optically pure (+)- or (−)-camphanic chloride (VIII A) or achiral pivaloyl chloride (VIII B) by HPLC:

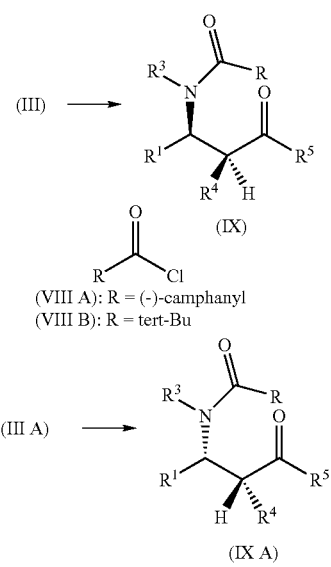

The N-acylated derivatives (IX) and (IX A) are stable and can no longer undergo a retro-Mannich reaction. The use of (−)-camphanic chloride has the advantage that the derivatives (IX) and (IX A) are diastereoisomers and can therefore be separated on conventional HPLC columns having an achiral stationary phase. However, the method has the disadvantage that a (usually small) distortion of the stereoisomeric ratios (undesired kinetic optical resolution) may occur during the derivatization, since the reaction rates of (III) and (III A) with this acid chloride are not identical. (III) and (III A) have to react with the achiral pivaloyl chloride (VIII B) at the same rate, so that distortion of the stereoisomeric ratios can be ruled out in this case. However, the derivatization products (IX) and (IX A) in this case are enantiomers, so that an HPLC column having a chiral stationary phase is required for their separation. The analyses of a large number of samples show that the enantiomeric excesses determined using (−)-camphanoyl chloride are distorted to give ee values which are worse by up to 4% compared to the more reliable determinations using pivaloyl chloride.

As an example of the increase with time of the proportion of the product (III) at the expense of (III A) in the precipitate of a four-component coupling reaction, a reaction was investigated wherein $R^1$ is o-nitrophenyl, $R^2$ is 2-pyridyl, $R^3$ is hydrogen, $R^4$ is 2-pyridyl, $R^5$ is phenyl and HY* is (+)-di-O,O'-pivaloyl-D-tartaric acid, and the solvent is ethanol, and the reaction temperature is 20–25° C.

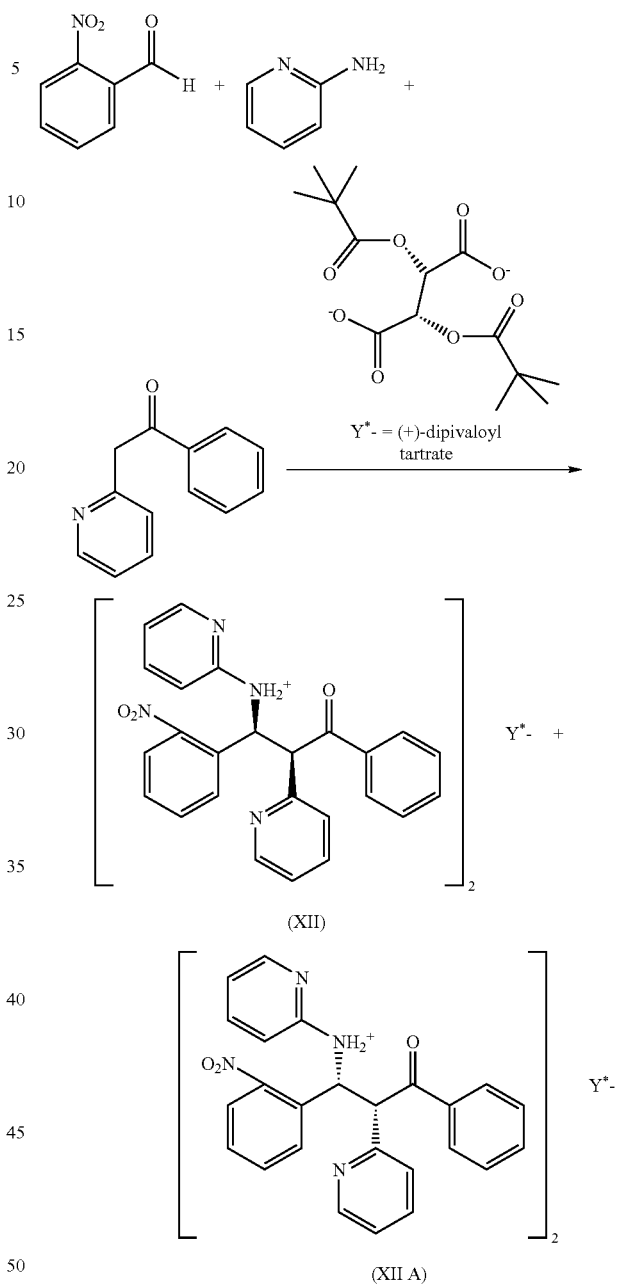

TABLE 1

Progress against time of the formation of an exemplary compound of formula (III) as a ratio to its enantiomer

| t [h] | Content of (XII) [%] | Content of (XII A) [%] |
|---|---|---|
| 21 | 62.68 | 37.32 |
| 46 | 67.27 | 32.73 |
| 62.5 | 69.67 | 30.33 |
| 130 | 78.40 | 21.60 |
| 154.5 | 83.68 | 16.32 |
| 177 | 86.74 | 13.26 |
| 202 | 89.99 | 10.01 |
| 225 | 94.89 | 5.11 |

TABLE 1-continued

Progress against time of the formation of an exemplary
compound of formula (III) as a ratio to its enantiomer

| t [h] | Content of (XII) [%] | Content of (XII A) [%] |
|---|---|---|
| 297 | 96.91 | 3.09 |
| 322 | 97.67 | 2.33 |

In the precipitate (XII)/(XII A) there are two cations for each (+)-DPTA anion. In this experiment, the reaction mixture was stirred using a Teflon-coated magnetic stirrer bar in a round-bottom flask. The first sample that is taken after 21 hours contained (III) and (III A) in a ratio 62.7:37.3. After 322 hours, the ratio was 97.7:2.3. This corresponds to an enantiomeric excess of the underlying free base of 95.4% ee. The higher the reaction temperature, the more rapid the rise in the (XII)/(XII A) ratio in the precipitate of the four-component coupling, which also exhibits a distinct dependence upon solvents and upon the nature of the chiral Brønsted acid (VII).

For optimum results, preference is given to carrying out the process step 1 according to the invention with the use of a stirrer that ensures particularly efficient mixing and comminution of solid particles in the reaction suspension.

The process step 1 may be carried out in water, with or without the addition of organic solvents and/or solubilizers, or, when one or more of the reactants (IV)–(VII) is liquid at the reaction temperature, can also be carried out in the absence of solvents ("neat").

A suitable solvent is water or an organic solvent, or a mixture of water with an organic solvent, optionally containing a solubility-enhancing additive, for example a phase transfer catalyst, where organic solvents may be present in 100% purity or technical quality, for example a $C_1$–$C_8$-alcohol, branched or unbranched, preferably methanol, ethanol, n-propanol, isopropanol or n-butanol, or a ketonic solvent, preferably acetone or methyl ethyl ketone (MEK), or an ester, preferably ethyl acetate or n-butyl acetate, or an ether, preferably tetrahydrofuran, methyl tert-butyl ether, diisopropyl ether, 1,2-dimethoxyethane or diethylene glycol dimethyl ether (diglyme), or a hydrocarbon, aliphatic or aromatic, preferably toluene, or a supercritical medium, preferably supercritical carbon dioxide or a halogenated hydrocarbon, preferably dichloromethane, or a polar, aprotic solvent, preferably DMF, DMSO or NMP.

The water present in the reaction is optionally removed, for example, by azeotropic distillation or by adding water-binding additives, for example magnesium sulfate or activated molecular sieves.

The reaction is carried out at a temperature of from −15° C. to +140° C., preferably at from +10° C. to +100° C., more preferably at from +30° C. to +70° C.

The process step 1 may be carried out at atmospheric pressure, under reduced pressure (vide supra, for example for the purpose of distilling off an azeotrope) or under pressure, the latter for the purpose of reaction acceleration, in an inert gas atmosphere or under air.

The process step 1 according to the invention is carried out using 0.80–2.00 molar equivalents of the reactants (IV) and (V), and also 0.80–4.00 molar equivalents of the chiral acid (VII), based in each case on reactant (VI). Preference is given to carrying out the process according to the invention using 0.95–1.30 molar equivalents of the reactants (IV) and (V), and also 1.00–2.00 molar equivalents of the chiral acid (VII), based in each case on 1.00 molar equivalents of the reactant (VI). Particular preference is given to carrying out the process according to the invention using 1.00–1.25 molar equivalents of the reactants (IV) and (V), and also 1.05–1.50 molar equivalents of the chiral acid (VII), based in each case on 1.00 molar equivalents of the reactant (VI).

Table 2 shows the results of four-component couplings to give a compound of formula (III) using (+)-dipivaloyl-D-tartaric acid [(+)-DPTA] as the chiral acid (VII)

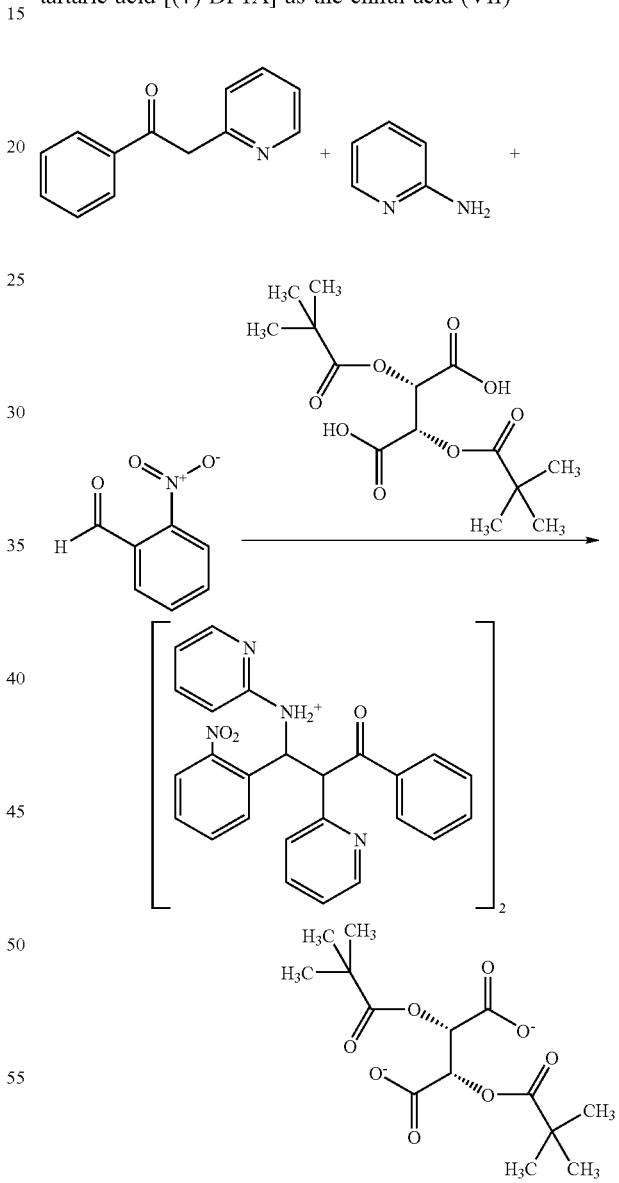

and using typical laboratory glass reaction vessels (up to 0.5 mol in multineck round-bottom flasks, above 0.5 mol in cylindrical jacketed reactors rounded at the bottom) equipped with motor-driven mechanical stirrers (up to 0.5 mol using a precision glass stirrer having Teflon paddles; above 0.5 mol using a steel turbine stirrer).

TABLE 2

| No. | (IV) (R¹ = 2-Nitro-Ph) mmol mol. Equiv. | (V) (R² = 2-Py, R³ = H) mmol mol. equiv. | (VI) (R⁴ = 2-Py, R⁵ = Ph) mmol mol. equiv. | (VII) (+)-Dipivaloyl-D-tartaric acid mmol mol. equiv. | Solvent [ml] | Reaction conditions | (III) isolated yield % of theory | (III) % ee (HPLC) Camph. derivative | (III) % ee (HPLC) Piv. derivative |
|---|---|---|---|---|---|---|---|---|---|
| 1 | 386.33 1.2 | 402.43 1.25 | 321.94 1.0 | 321.94 1.0 | MeOH 756, then EtOH 756 | MeOH 30° C./55 h then EtOH 40° C./ 60 h | 93.6 | 17 h 30° C. MeOH 80.5<br>30 h 30° C. MeOH 83.8<br>51 h 30° C. MeOH 86.1<br>10 h 40° C. EtOH 89.5<br>58 h 40° C. EtOH 92.2<br>isol. (60 h) EtOH 91.8 | — |
| 2 | 36 1.2 | 37.5 1.25 | 30 1.0 | 30 1.0 plus 0.3 mmol, 0.01 meq of 4-toluene-sulfonic acid monohydrate (p-TosOH) | ethanol 75 | RT/8 days; 4-toluene-sulfonic acid mono-hydrate (p-TosOH), 0.3 mmol, 0.01 meq | 85.3 | 42 h: 26.7<br>91 h: 42.8<br>isol. (190 h) 74.0 | — |
| 3 | 36 1.2 | 37.5 1.25 | 30 1.0 | 30 1.0 | ethanol 75 | RT/8 days | 83 | 42 h: 30.7<br>164 h: 65.1<br>isol. (190 h) 74.2 | — |
| 4 | 152.13 1.2 | 158.63 1.25 | 126.75 1.0 | 126.75 1.0 | ethanol 318 | RT/11 days | 98.2 | 1 day: 27.8<br>7 days: 71.9<br>isolated (11 d.) 95.1 | — |
| 5 | 28.2 1.2 | 29.4 1.25 | 23.5 1.0 | 23.5 1.0 | ethanol 59 | RT/14 days | 83.6 | 1 day: 25.4<br>6 days: 56.8<br>10 days: 89.8<br>13 days: 93.8<br>isol. (14 d.) 95.3 | — |
| 6 | 30.5293 1.19 | 31.759 1.24 | 25.654 1.0 | 25.375 1.0 | ethanol 70 | 40° C./1 day | 99.5 | 4.16 h: 55.7<br>20 h: 93.0<br>isolated 95.9 | — |
| 7 | 34.059 1.206 | 35.642 1.262 | 28.239 1.0 | 28.279 1.0 | ethanol 65 | 40° C./1 day | 94.4 | 5.7 h: 68.9 h: 95.3<br>25 h: 95.5<br>isolated 96.6 | 96.8 |
| 8 | 75.469 1.20 | 78.672 1.25 | 62.867 1.0 | 62.90 1.0 | acetone 170 | 40° C./17 h Sample of the product stirred at 40° C. in acetone | 90.9 | 1.5 h: 95.2<br>17 h: 93.0<br>isol. 92.5<br>1 h: 96.4 | 94.6<br>96.4 |

Four-component couplings corresponding to the above-described reactions were carried out to give compounds of formula (III) using S-(+)-mandelic acid.

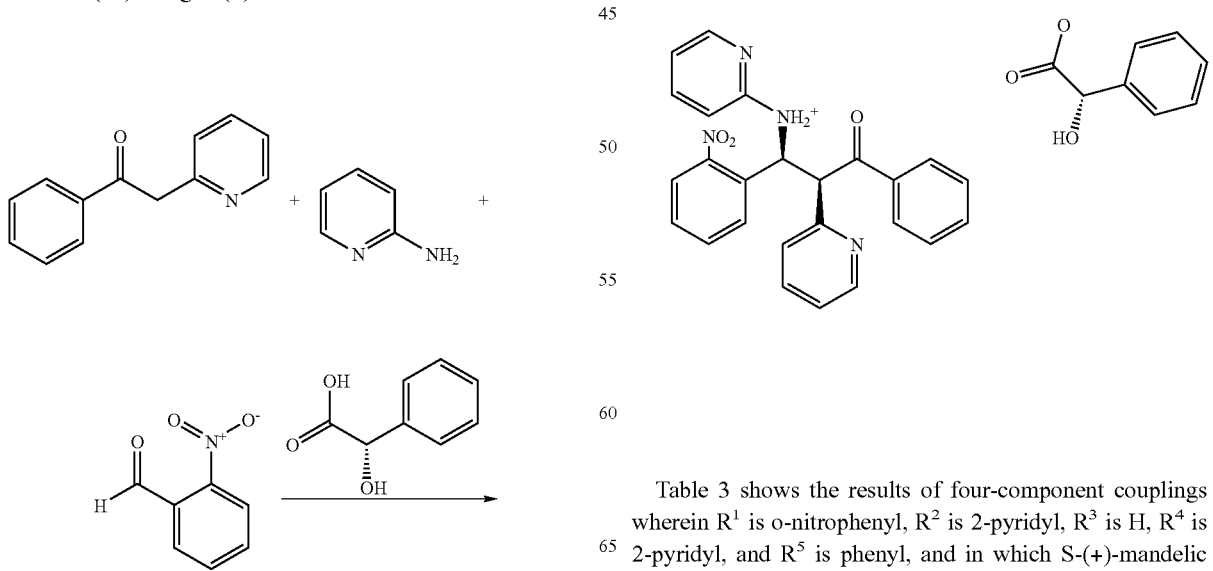

Table 3 shows the results of four-component couplings wherein R¹ is o-nitrophenyl, R² is 2-pyridyl, R³ is H, R⁴ is 2-pyridyl, and R⁵ is phenyl, and in which S-(+)-mandelic acid was used as a Brønsted acid (VII):

TABLE 3

| No. | (IV): $R^1$ is 2-Nitro-Ph; mmol mol. Equiv. | (V): $R^2$ is 2-Py, $R^3$ is H; mmol mol. equiv. | (VI): $R^4$ is 2-Py, $R^5$ is Ph; mmol mol. equiv. | (VII) is (S)-(+)-mandelic acid mmol mol. equiv. | Solvent [mL] | Reaction conditions | (III) isolated yield % of theory | (III) % ee (HPLC) Camph. derivative | (III) % ee (HPLC) Piv. derivative | (III) syn/anti ratio ($^1$H NMR) |
|---|---|---|---|---|---|---|---|---|---|---|
| 1 | 250.0 1.00 | 262.0 1.05 | 250.0 1.00 | 275.0 1.10 | MeOH 400 | 40° C./2 h, then 60° C./1 h | 83.3 | 95.0 | 97.3 | >99.0:<1.0 |
| 2 | 250.0 1.00 | 262.0 1.05 | 250.0 1.00 | 275.0 1.10 | MeOH 400 | 60° C./16 h | 78 | 1 h: 92.6 isolated: 95.6 | 97.1 | n.d. |
| 3 | 91.25 1.20 | 91.30 1.20 | 76.05 1.00 | 152.09 2.00 | MeOH 195 | 60° C./23 h | 67.4 | 95.7 | 95.6 | >99.0:<1.0 |
| 4 | 770.7 1.18 | 800.0 1.24 | 643.9 1.00 | 1287.8 2.00 | EtOH abs. 1512 | 40° C./53 h | 95.3 | 94.4 | n.d. | 99.0:1.0 |
| 5 | 755.5 1.17 | 792 1.23 | 643.9 1.00 | 1314.5 2.04 | EtOH (MEK) 1510 | 40° C./44 h | 93.8 | 3.5 h: 6.7 21 h: 79.0 25 h: 89.0 44 h: 94.8 isolated: 95.6 | 95.2 | 98.4:1.6 |
| 6 | 30.44 1.20 | 30.39 1.20 | 25.35 1.00 | 50.68 2.00 | EtOH (MEK) 65 | 60° C./4 h | 90.9 | 2 h: 94.0 isolated: 94.6 | 95.2 | 99.1:0.9 |
| 7 | 591.4 1.20 | 591.4 1.20 | 492.8 1.00 | 985.6 2.00 | EtOH (MEK) 1200 | 60° C./4.5 h | 92.4 | 2 h: 91.5 3.5 h: 93.0 isolated: 94.4 | 97.5 | 98.6:1.4 |
| 8 | 1200 1.20 | 1250 1.25 | 1000 1.00 | 2000 2.00 | EtOH (MEK) 2430 | 60° C./6 h | 92.6 | 2 h: 90.7 4 h: 92.4 5 h: 92.9 isolated: 95.8 | 94.6 | 99.0:1.0 |
| 9 | 840.0 1.20 | 840.0 1.20 | 700.0 1.00 | 1400.0 2.00 | EtOH (MEK) 852 | 60° C./20 h | 90.2 | 2 h: 80.7 19 h: 94.2 isolated: 94.1 | n.d. | 99.4:0.6 |
| 10 | 30.0 1.20 | 31.25 1.25 | 25.00 1.00 | 37.5 1.50 | EtOH (MEK) 60 | 60° C./7 h | 87.2 | 1.5 h: 56.4 3.5 h: 92.8 5.3 h: 92.9 isolated: 93.2 | 94 | 98.9:1.1 |
| 11 | 152.13 1.20 | 152.15 1.20 | 126.75 1.00 | 190.14 1.50 | EtOH (MEK) 162.5 | 60° C./7 h | 92.2 | 2 h: 61.3 4 h: 91.4 6 h: 92.6 isolated: 92.8 | 94.7 | 98.7:1.3 |
| 12 | 26.61 1.05 | 27.24 1.075 | 25.35 1.00 | 27.88 1.10 | EtOH (MEK) 65 | 60° C./5 h standing 15 h at RT 60° C./1.5 h | 77.2 | 2 h: 88.6 4 h: 94.6 standing RT: 86.2 6.5 h rct.: 95.3 isolated: 92.3 | 94 | n.d. |
| 13 | 1065 1.05 | 1090 1.075 | 1014 1.00 | 1115 1.10 | EtOH (MEK) 1300 | 60° C./7 h | 92.7 | 2 h: 70.9 4 h: 93.7 6 h: 94.4 7 h rct.: 94.2 isolated: 93.1 | 92.9 | 98.5:1.5 |
| 14 | 250.0 1.00 | 262.0 1.05 | 250.0 1.00 | 275.0 1.10 | EtOH (MEK) 400 | 60° C./16 h | 86.1 | 92.2 | 95.4 | >99.0:<1.0 |
| 15 | 125.0 1.00 | 131.0 1.05 | 125.0 1.00 | 131.0 1.05 | EtOH (MEK) 250 | 60° C./16 h | 88.1 | 95.2 | 95.4 | >99.0:<1.0 |
| 16 | 30.44 1.20 | 31.66 1.25 | 25.35 1.00 | 26.62 1.05 | EtOH (MEK) 65 | 60° C./5 h standing for 16 h at RT; 60° C./2 h | 79 | 4 h: 95.1 standing at RT: 87.9 7 h rct.: 96.4 isolated: 93.0 | 93.5 | 98.5:1.5 |
| 17 | 250.0 1.00 | 262.0 1.05 | 250.0 1.00 | 275.0 1.10 | i-PrOH 400 | 60° C./16 h | 90.7 | 92.8 | 96.3 | n.d. |
| 18 | 250.0 1.00 | 262.0 1.05 | 250.0 1.00 | 275.0 1.10 | n-BuOH 400 | 60° C./16 h | 86.2 | 92.2 | 95.6 | n.d. |
| 19 | 125.0 1.00 | 131.0 1.05 | 125.0 1.00 | 131.0 1.05 | n-BuOH 250 | 60° C./16 h | 87 | 93.4 | 93.3 | n.d. |
| 20 | 591.4 1.20 | 591.4 1.20 | 492.8 1.00 | 985.6 2.00 | acetone 1200 | 40° C./24 h | 88.2 | 95.7 | 97 | 98.6:1.4 |
| 21 | 24.31 1.18 | 25.40 1.24 | 20.53 1.00 | 40.75 1.98 | acetone 56 | 40° C./27 h | 85.3 | 97.2 | n.d. | 99.0:1.0 |
| 22 | 125.0 1.00 | 131.0 1.05 | 125.0 1.00 | 131.0 1.05 | MeCO2n-Bu | 60° C./16 h | 84.6 | 92.4 | 95.1 | n.d. |

TABLE 3-continued

| No. | (IV): R¹ is 2-Nitro-Ph; mmol mol. Equiv. | (V): R² is 2-Py, R³ is H; mmol mol. equiv. | (VI): R⁴ is 2-Py, R⁵ is Ph; mmol mol. equiv. | (VII) is (S)-(+)-mandelic acid mmol mol. equiv. | Solvent [mL] | Reaction conditions | (III) isolated yield % of theory | (III) % ee (HPLC) Camph. derivative | (III) % ee (HPLC) Piv. derivative | (III) syn/anti ratio (¹H NMR) |
|---|---|---|---|---|---|---|---|---|---|---|
| 23 | 125.0 1.00 | 131.0 1.05 | 125.0 1.00 | 131.0 1.05 | MeCO₂n-Bu | 60° C./ 16 h (Schiff base generated), 40° C.→60° C./ 20% excess of mandellic acid | 93.4 | 95.4 | 98 | >99.0:<1.0 |

Four-component couplings using (+)-DPTA, (S)-(+)-mandelic acid or (−)-malic acid were carried out in the ten reactors operated in parallel of an Argonaut Surveyor Reaction Screening System in accordance with the reaction conditions summarized in Tables 4 and 5 and in different solvents. In these reactors, mixing is effected by piston activated magnetic agitation. Mixing is distinctly more efficient than that of magnetic stirrer bars or of precision glass paddle stirrers and slightly more efficient than that of turbine stirrers.

Table 4 shows the results of four-component couplings using (+)-DPTA, (S)-(+)-mandelic acid or (−)-malic acid

TABLE 4

| Batch | Acid (VII) | Solvent | T [° C.] | t [h] | Content (IX) [%] | Content (IX A) [%] | Molar weight (I) [g/mol] | Ratio (I)/(VII) | Yield in weight [g], % of theory |
|---|---|---|---|---|---|---|---|---|---|
| 1 | (+)-DPTA | EtOH | 35 | 3 | 65.21 | 34.79 | 1167.25 | 2:1 | 2.35 |
|  |  |  |  | 6 | 67.19 | 32.81 |  |  | 80.5% |
|  |  |  |  | 9 | 67.31 | 32.69 |  |  |  |
|  |  |  |  | 15 | 73.22 | 26.78 |  |  |  |
| 10 |  | EtOH | 50 | 3 | 87.90 | 12.1 | 1167.25 | 1.75:1 (NMR) | 2.12 |
|  |  |  |  | 6 | 91.16 | 8.84 |  |  | 72.7% |
|  |  |  |  | 9 | 95.97 | 4.03 |  |  |  |
|  |  |  |  | 15 | 98.36 | 1.64 |  |  |  |
| 4 |  | MeOH | 30 | 3 | 90.12 | 9.88 | 1167.25 | 1.82:1 (NMR) | 2.19 |
|  |  |  |  | 6 | 93.85 | 6.15 |  |  | 75.1% |
|  |  |  |  | 9 | 96.94 | 3.06 |  |  |  |
|  |  |  |  | 15 | 98.50 | 1.5 |  |  |  |
| 7 |  | n-BuOH | 50 | 3 | 84.83 | 15.17 | 1167.25 | 1.91:1 (NMR) | 2.04 |
|  |  |  |  | 6 | 85.76 | 14.24 |  |  | 69.9% |
|  |  |  |  | 9 | 87.84 | 12.16 |  |  |  |
|  |  |  |  | 15 | 91.40 | 8.6 |  |  |  |
| 2 | (S)-(+)-mandelic acid | EtOH | 40 | 3 | 54.98 | 45.02 | 576.61 | 1:1 | 2.16 |
|  |  |  |  | 6 | 61.12 | 38.88 |  |  | 74.9% |
|  |  |  |  | 9 | 67.16 | 32.84 |  |  |  |
|  |  |  |  | 15 | 71.94 | 28.06 |  |  |  |
| 5 |  | MeOH | 30 | 3 | 67.37 | 32.63 | 576.61 | 1:1 (NMR) | 2.14 |
|  |  |  |  | 6 | 71.31 | 28.69 |  |  | 74.2% |
|  |  |  |  | 9 | 82.67 | 17.33 |  |  |  |
|  |  |  |  | 15 | 97.72 | 2.28 |  |  |  |
| 8 |  | n-BuOH | 50 | 3 | 60.01 | 39.99 | 576.61 | 1:1 (NMR) | 2.27 |
|  |  |  |  | 6 | 66.15 | 33.85 |  |  | 78.7% |
|  |  |  |  | 9 | 79.32 | 20.68 |  |  |  |
|  |  |  |  | 15 | 97.13 | 2.87 |  |  |  |
| 3 | (−)-malic acid | EtOH | 50 | 3 | — | — | 938.01 | 2:1 | 1.21 |
|  |  |  |  | 6 | 49.05 | 50.95 |  |  | 51.6% |
|  |  |  |  | 9 | 47.08 | 52.92 |  |  |  |
|  |  |  |  | 15 | 48.87 | 51.13 |  |  |  |
| 6 |  | MeOH | 50 | 3 | — | — | 938.01 | 2:1 | 0.58 |
|  |  |  |  | 6 | — | — |  |  | 24.7% |
|  |  |  |  | 9 | — | — |  |  |  |
|  |  |  |  | 15 | 49.08 | 50.92 |  |  |  |

TABLE 4-continued

| Batch | Acid (VII) | Solvent | T [° C.] | t [h] | Content (IX) [%] | Content (IX A) [%] | Molar weight (I) [g/mol] | Ratio (I)/(VII) | Yield in weight [g], % of theory |
|---|---|---|---|---|---|---|---|---|---|
| 9 | | n-BuOH | 50 | 3 | — | — | 938.01 | 2:1 (NMR) | 1.67 71.2% |
| | | | | 6 | — | — | | | |
| | | | | 9 | — | — | | | |
| | | | | 15 | 91.52 | 8.48 | | | |

Table 5 shows four-component couplings using (S)-(+)-mandelic acid in various solvents in the surveyor screening system:

TABLE 5

| mol. eq. mandelic acid | Mass [g] | Yield % of theory | Solvent | ee (HPLC) [%] | Ratio (I)/(VII) [¹H NMR] |
|---|---|---|---|---|---|
| 2.00 | 2.51 | 86.0 | EtOH, MEK | 95.2 | 1:1 |
| 2.00 | 2.52 | 86.3 | EtOH, toluene | 94.4 | 1:1 |
| 2.00 | 2.39 | 81.8 | EtOH, abs. | 94.8 | 1:1 |
| 2.00 | 2.52 | 86.3 | n-BuOH | 96 | 1:1 |
| 2.00 | 2.75 | 94.2 | i-PrOH | 94 | 1:1 |
| 2.00 | 2.24 | 76.7 | MeOH | 98.6 | 1:1 |
| 2.00 | 1.49 | 51.0 | MEK | 97.4 | 1:1 |
| 2.00 | 1.92 | 65.8 | Acetone | 97.8 | 1:1 |
| 2.00 | 2.55 | 87.3 | n-BuOAc | 96.0 | 1:1 |
| 2.00 | 2.40 | 82.2 | MeOH | 98.6 | 1:1 |
| 1.1 | 2.35 | 80.6 | MeOH | 95.0 | 1:1 |
| 1.2 | 2.44 | 83.5 | MeOH | 94.8 | 1:1 |
| 1.5 | 2.49 | 85.2 | MeOH | 95.2 | 1:1 |
| 2.0 | 2.57 | 88.0 | MeOH | 93.2 | 1:1 |
| 1.1 | 2.40 | 82.3 | EtOH, MEK | 91.2 | 1:1 |
| 1.2 | 2.48 | 85.0 | EtOH, MEK | 91.8 | 1:1 |
| 1.1 | 2.59 | 88.8 | i-PrOH | 92.0 | 1:1 |
| 1.2 | 2.69 | 92.2 | i-PrOH | 93.4 | 1:1 |
| 1.5 | 2.71 | 92.7 | i-PrOH | 93.0 | 1:1 |
| 2.0 | 2.40 | 82.2 | i-PrOH | 94.3 | 1:1 |
| 1.1 | 2.29 | 78.4 | n-BuOAc | 90.8 | n.d. |
| 1.2 | 2.53 | 86.6 | n-BuOAc | 94.0 | n.d. |
| 1.5 | 2.45 | 83.9 | n-BuOAc | 94.4 | n.d. |
| 2.0 | 2.57 | 88.0 | n-BuOAc | 96.0 | n.d. |
| 1.5 | 2.58 | 88.4 | EtOH, MEK | 93.6 | n.d. |
| 2.0 | 2.48 | 84.9 | EtOH, MEK | 93.0 | n.d. |
| 1.1 | 2.52 | 86.3 | n-BuOH | 92.4 | n.d. |
| 1.2 | 2.52 | 86.3 | n-BuOH | 95.4 | n.d. |
| 1.5 | 2.63 | 90.1 | n-BuOH | 96.4 | n.d. |
| 2.0 | 2.40 | 82.2 | n-BuOH | 95.0 | n.d. |
| 1.5 | 13.08 | 89.5 | MeOH | 91.2 | n.d. |
| 1.5 | 9.67 | 66.2 | Acetone | 94.6 | n.d. |

Unless otherwise stated in the tables, the product (III) was isolated by cooling the suspension to room temperature, followed by filtration and washing of the solid with a little cold solvent.

In methanol at 60° C., the combined four-component coupling/dynamic optical resolution proceeded very quickly. After only one hour, the underlying free Mannich base (I) of the precipitate (III)/(III A) had achieved an enantiomeric excess of 92.6% ee (Table 3, line 2) and, after a maximum of 3 hours, the reaction was completed at 97.3% ee (Table 3, line 1). Owing to the more efficient mixing, up to 98.6% ee was obtained in the Surveyor Screening System (Table 5).

Owing to the not inconsiderable solubility at room temperature of (III) in methanol, the yields were at least 10% below those in ethanol. Even at only 30° C., the reaction in methanol was completed within 15 hours (Table 4). In ethanol, the reaction at 40° C. required 44–53 hours (Table 3, lines 4 and 5). Yields (up to 95.3% of theory) and enantiomeric excesses (approx. 95% ee) were high. At 60° C., the reaction in ethanol was completed after only approx. 4 hours when two equivalents of mandelic acid were used. Yields (up to 92.6% of theory) and enantiomeric excesses (up to 97.5% ee) remained high (Table 3, lines 6–8). When the reaction was carried out at very high concentration, the reaction rate fell somewhat, while yield and ee fell marginally (Table 3, line 9). Using 1.5 equiv. of mandelic acid, the reaction at 60° C. in ethanol required approx. 7 hours and led to only slightly lower yields and ee values (Table 3, lines 10 and 11). Using 1.10 equiv. of mandelic acid (Table 3, lines 12 to 14) and using only 1.05 equiv. of mandelic acid (Table 3, lines 15 to 16), the phenomenon was again observed that an ee obtained at 60° C. in ethanol distinctly worsened on cooling the suspension to RT (before filtering off the product with suction). Standing overnight may result in an ee reduction of 8% (line 16). However, when the cooling of the suspension and the filtering off with suction of (III) were effected rapidly, an 88% yield and 95.4% ee were obtained even when only 1.05 equiv. of mandelic acid were used (line 15). In the case of reactions using 2.0 equiv. of mandelic acid, such ee deteriorations on cooling did not occur. An aliquot of the reacted reaction suspension (60° C., ethanol) was withdrawn and stirred at room temperature for 72 hours. The enantiomeric excess and the syn/anti ratio afterwards were unchanged. The reaction may be carried out with similar success in relatively long-chain branched or unbranched alcohols, for example isopropanol (Table 3, line 17, Table 5) or n-butanol (Table 3, lines 18 and 19; Tables 4 and 5). It also succeeds in ketonic solvents, for example acetone (Table 3, lines 20 and 21; Table 5) or methyl ethyl ketone (MEK, Table 5), in esters, for example ethyl acetate or n-butyl acetate (Table 3, lines 22 and 23; Table 5) and in halogenated hydrocarbons, for example dichloromethane.

The reaction can in principle be carried out in ethers, for example tetrahydrofuran, methyl tert-butyl ether, diisopropyl ether, 1,2-dimethoxyethane, or diethylene glycol dimethyl ether (diglyme), in hydrocarbons, for example toluene, and also in supercritical media, for example supercritical carbon dioxide. The use of solubility-enhancing additives, for example phase transfer catalysts or cosolvents may be advantageous. The reaction can be carried out in polar, aprotic solvents, for example dimethylformamide (DMF), dimethylacetamide (DMA), dimethyl sulfoxide (DMSO) or N-methylpyrrolidinone (NMP). The yields isolated in these solvents are competitive when the solubility of (III) in them is not too high.

The reaction tolerates a content of moisture. Comparison of Table 3, line 4 with line 5 and of Table 5, lines 1–3 shows that absolute ethanol offers no advantages over technical, or MEK- or toluene-denatured ethanol. In some examples, the observation was made that when solvents were used which form low-boiling azeotropes with water (for example ethanol), continuous azeotropic distilling off of the water of reaction formed in the Mannich reaction at atmospheric pressure or under a reduced pressure leads to significant to moderate reaction acceleration. This may be utilized to optimize the space-time yield and, owing to the relatively short thermal stress, occasionally be used to improve the chemical purity and isolated yield of the product.

Similar results can also be obtained by water-binding additives, for example dried magnesium sulfate or activated molecular sieves. However, the exclusion of water and/or the removal of the water of reaction formed are necessary neither for the practical quantitative progress of the four-component Mannich coupling, nor for the progress of the dynamic optical resolution. Tables 1–5 confirm that when the necessary reaction times are accepted, the product (III) may also be obtained in very high yield, chemical purity and with high enantiomeric excess when undried apparatus and undried solvents are used and the resulting water of reaction is not removed.

In accordance with Tables 2–5, the relative molar amounts of the four reactants (IV)–(VI) can be varied within considerable intervals without any resulting negative effects on yield, chemical purity or enantiomeric excess of the product (III). Using 1.00 equivalents of the CH-acidic components (VI) as the basis in each case, the amounts of the remaining reactants used in the specific examples (Tables 1–5) were varied within the following intervals: aldehyde (IV): 1.00–1.20 equivalents; amine (V): 1.05–1.25 equivalents, chiral acid (VII): 1.05–2.00 equivalents.

The most important factor for the efficiency of the dynamic optical resolution in process step 1 is a good choice of the chiral acid HY* of formula (VII). In all fields of stereochemistry, there is now a consensus that there is no optimum chiral auxiliary per se or an optimum chiral ligand per se, nor can there be one. The extent of asymmetry of reactions rather depends upon the specific reactant/auxiliary and product/auxiliary interactions ("chiral recognition"). Which chiral acid (VII) delivers an optimum result within the process according to the invention thus depends on the specific nature of the substituents $R^1$ to $R^5$ and has to be determined, generally experimentally, in each case independently for each combination of the reactants (IV) to (VI). This may be achieved in the following way:

a) The racemic free Mannich base rac.-(I) is prepared. This may be effected particularly simply by one of the two following alternative routes:
   a1) The four-component Mannich coupling is carried out in a similar manner to process step 1, except that the reactants (IV), (V) and (VI) are used with only catalytic amounts of an achiral acid in a solvent in which the Mannich base rac.-(I) has only moderate solubility. In many cases, the use of approx. 1 mol % of p-toluene-sulfonic acid hydrate in the solvent ethanol has proven useful. The free Mannich base rac.-(I) then crystallizes out of the reaction mixture sometimes in very high yields and may be isolated by filtration. Example 3 describes a corresponding procedure.
   a2) The four-component Mannich coupling is carried out in a similar manner to process step 1, except that the reactants (IV), (V) and (VI) are carried out using stoichiometric or greater than stoichiometric amounts of an achiral acid in one of the abovementioned solvents suitable for process step 1. In this case, a salt similar to formula (III) is obtained in which the cation is racemic and the anion $Y^-$ is achiral. This salt rac.-(III) is the converted to the free racemic Mannich base rac.-(I) in a similar manner to process step 2.

b) A solvent is found in which rac.-(I) is averagely to moderately soluble (preferred solubility approx. 1–5% by weight) and in which its retro-Mannich reaction proceeds as slowly as possible. To select this solvent, various alternative physical or chemical methods are available:
   b1) Rac.-(I) is dissolved in appropriate perdeuterated solvents and the retro-Mannich rates in each case are monitored by repeatedly analyzing the solutions by $^1$H or $^{13}$C NMR at short time intervals;
   b2) Rac.-(I) is dissolved in solvents to obtain real time monitoring of the retro-Mannich reaction with the aid of a ReactIR probe, or by analyzing the solution in a cuvette in a conventional two-beam IR instrument at regular time intervals, using in each case an identical cuvette filled with the pure solvent in the reference beam.
   b3) Rac.-(I) is dissolved or suspended in aprotic solvents which are compatible with an amidation reaction using acid chlorides. Immediately after they are prepared, the solutions or suspensions are reacted with pivaloyl chloride (VIII B) to give the racemic pivaloyl derivative (IX)/(IX A). The slower the retro-Mannich reaction in the particular solvent, the higher the yield and purity of the amide (IX)/(IX A) achieved. Example 4 describes a corresponding procedure.

In the examples investigated hitherto, it has been found that the retro-Mannich tendency of the salts of structurally analogous Mannich bases with Brønsted acids (formula II) under identical conditions (same solvent, same temperature, same Brønsted acid) is supported by electron-donating substituents in the aldehyde component of formula (IV). Electron-withdrawing substituents in the aldehyde component of formula (IV) reduced the retro-Mannich tendency. The 1H NMR monitoring of the syn/anti-isomerization of a syn-Mannich salt of formula (III) via retro-Mannich reaction at 300 K in DMSO-d6 solution can be seen in Example 28. As can be seen from Example 27, good choice of the reaction parameters in the four-component coupling results in Mannich salts in excellent yield with very high diastereomeric and enantiomeric purity of the underlying Mannich base even when the aldehyde component contains electron-donating substituents and the retro-Mannich tendency is high.

In the above-described examples, it has been found that the retro-Mannich reaction of free Mannich bases rac.-(I) frequently proceeds very slowly in acetone.

c) A screening of all available optically active Brønsted acids HY* (VII) with regard to efficiency of a classical optical resolution is carried out with the solution or suspension of rac.-(I) in the solvent obtained according to b). To this end, when the substituents $R^1$ to $R^5$ contain no basic centers, the freshly prepared suspension of rac.-(I) is reacted with 1.0 molar equivalent of the acid (VII) when (VII) is a monobasic acid, or with 0.5 molar equivalent of the acid (VII) when (VII) is a dibasic acid. When the substituents $R^1$ to $R^5$ contain basic centers, more molar equivalents of the acid (VII) are correspondingly added. The mixture is stirred for approx. 20 h at room temperature, the precipitated salt (III) is isolated by filtration and the enantiomeric ratio present in the underlying free base (I) is determined by derivatizing to (IX)/(IX A), followed by HPLC analysis (vide supra). The chiral Brønsted acids (VII) selected are those which deliver the highest (IX):(IX A) ratios, preferably (IX):(IX A)≧95:≦5 in the screening. Example 6 describes a representative experimental procedure for such a screening.

d) Further selection may be effected among the optically active Brønsted acids (VII) selected according to c) in order to very substantially fulfill the following criteria for particularly preferred acids (VII):

Y*⁻ has a stable configuration under the reaction conditions;

it leads to a maximum difference in solubility between its two diastereomeric salts (III) and (III A)

it effects a very low solubility of the desired diastereomer of formula (III) and a very high solubility of the undesired diastereomer of formula (III A)

the racemate of the salt of formula (III) (1:1 mixture of salt (III) and its mirror image) crystallizes as a conglomerate. A conglomerate consists of a mixture of two mirror image crystal structures of which one crystal structure corresponds to the crystal structure of the optically active salt (III). In the conglomerate, not only the enantiomeric molecules, but also the two crystal structures as supramolecular constructions are mirror images of one another. The two crystal structures in the conglomerate differ not only in the chirality of the molecules. The crystal packings, i.e., the three-dimensional periodic arrangements/stackings of the molecules in the two crystal structures are also mirror images.

it catalyzes the four-component Mannich reaction which leads to the formation of (III) and (III A), it catalyzes the retro-Mannich reaction of the more soluble diastereomeric salt (III A), i.e., the cleavage of the salt (III A) to the enolizable ketone (VI) and the iminium salt $R^1CH=N^+R^2R^3Y^{*-}$ or its dissociation products, the aldehyde (IV) and the salt of the amine (V) with HY*.

When the free Mannich base of formula (I) crystallizes as a conglomerate, the present invention also encompasses a special embodiment in which the three-component coupling and the dynamic optical resolution may be carried out in the absence of a chiral auxiliary acid HY*. In this embodiment, the solution of the three components (IV), (V) and (VI), optionally in the presence of catalytic amounts (approx. 1–10 mol %) of an achiral acid, for example p-toluenesulfonic acid, is seeded with crystals of optically pure free Mannich base. Owing to the conglomerate effect (preferential crystallization), only this antipode of the free Mannich base can crystallize out of the reaction solution and is continuously formed from the mirror image remaining in the solution. When this continued formation is rapid compared to the crystallization rate of the desired antipode, the boundary concentration of the wrong antipode at which it would also start to crystallize is never reached in the course of the reaction. For this reason, the precipitate at the end of the reaction consists exclusively of the desired antipode and the chemical yield may approach 100%. This asymmetric transformation of the 2nd kind without the necessity of a chiral auxiliary is referred to by the term "total spontaneous resolution" (E. H. Eliel, S. H. Wilen "Stereochemistry of Organic Compounds", John Wiley, New York, 1994, page 316; Y. Okada et al, J. Chem. Soc., Chem. Commun. 1983, 784–785).

In a further variant of the process step 1 according to the invention, the imine (X) is initially formed from the reactants (IV) and (V), and only then is the CH-acidic ketone (VI) added, which leads in the presence of a suitable optically active acid (VII) to the formation of the Mannich salt (III) with dynamic optical resolution. It will be appreciated that it is also possible to form the imine (X) from the aldehyde (IV) and the amine (V) in a known manner, catalyzed by an acid that may be achiral, for example approx. 1 mol % of p-toluenesulfonic acid hydrate, and to isolate the imine. Such a procedure is described in Example 9. The imine (X) may then be reacted afterwards with the ketone (VI) and the optically active acid (VII) to give the Mannich salt (III).

Some of the disadvantages of the indirect Mannich reaction are avoided when a solution of the imine (X) is initially formed by heating the aldehyde (IV) and an at least equimolar amount of the amine (V) in one of the abovementioned suitable solvents, more preferably n-butyl acetate, and azeotropically distilling off the resulting water of reaction, preferably under reduced pressure. Particular preference is given to carrying out this reaction step in an apparatus/a reactor that has the function of a water separator, i.e., after condensation of the azeotropic vapor and subsequent phase separation, the organic solvent having a lower specific gravity flows automatically back into the reactor, while the water is retained in the separator. Once the theoretical amount of water has separated, 0.80–2.00 equivalents of the CH-acidic ketone (VI) and 0.80–4.00 equivalents of the chiral acid (VII) (based in each case on the aldehyde (IV)), preferably 0.95–1.30 equivalents of (VI) and 1.00–2.00 equivalents of (VII), more preferably 1.00–1.25 equivalents of (VI) and 1.05–1.25 equivalents of (VII), are added to the reaction solution, and it is optionally further heated until the enantiomeric purity in the precipitate (III)/(III A) that appears after a short time has reached its maximum owing to the proceeding dynamic optical resolution.

As can be seen from Table 3 (No. 22, 23), when $R^1$ is o-nitrophenyl, $R^2$ is 2-pyridyl, $R^3$ is hydrogen, $R^4$ is 2-pyridyl, $R^5$ is phenyl, HY* is (S)-(+)-mandelic acid and the solvent was n-butyl acetate, the normal four-component coupling at 60° C. resulted in the Mannich salt III in an isolated yield of 84.6% of theory and in 95.1% ee. In contrast, when the n-butyl acetate solution of the imine (X) was initially formed in the manner described, the Mannich salt (III) was obtained in a yield of 93.1% of theory in 96.7% ee when heating to 60° C. was effected immediately after adding (VI) and (VII). A particularly high yield of 93.4% of theory and 98% ee was achieved when heating was initially effected only to 40° C. (commencing precipitation) after addition of (VI) and (VII), and the temperature was raised to 60° C. only after 4 h. In contrast, the normal four-component coupling resulted in parallel formation and reaction of the imine (X). In the present example, an investigation in a Mettler reaction calorimeter RC1 with real time monitoring of the progress of the reaction by ReactIR probe showed that in no phase of the four-component coupling was there any accumulation of more than 40% of the theoretical amount of the imine (X) in the reaction mixture. Furthermore, the duration of the thermal stress there on significant amounts of the imine (X) is substantially shorter.

In a further procedure variant of the process step 1 according to the invention, the aminal of formula (XI) may also be initially formed (Example 10) and then, either after intermediate isolation or in the original reaction solution, be reacted with the ketone (VI) and the acid (VII), optionally with the addition of an additional equivalent of the aldehyde (IV), to give the Mannich salt (III). In this procedure variant also, (III) is isolated in optical yields which approach those of the four-component coupling (Tables 2 to 5).

In all of the procedure variants of the process step 1 according to the invention mentioned here, the high optical activity of the Mannich salt (III) is based on the occurrence of a dynamic optical resolution. The process step according to the invention thus differs fundamentally from the four-component Mannich reaction described by B. List (J. Am. Chem. Soc. 2000, 122, 9336–9337). The latter concerns a catalytic asymmetric Mannich reaction, i.e., the addition step of an enamine resulting from the condensation reaction of the CH-acidic ketone (VI) with the catalyst (L)-proline, to the imine (X) which results from the condensation reaction of the aldehyde (IV) with the amine (V) with direct formation of the free Mannich base (I) is asymmetric. For this reason, only approx. 35 mol % of (L)-proline are used in the List reaction. The reaction product present in solution is already optically active and, according to the present level of understanding, the optical purity of the product does not fundamentally change during the progress of the reaction. In contrast, the process step 1 according to the invention is not carried out with "catalytic" amounts of the chiral acid (VII): when less than 0.8 molar equivalent of a monobasic acid (VII) or less than 0.4 molar equivalent of a dibasic acid (VII) is used, the isolated yields of the Mannich salt (III) inevitably fall to less than 70% of theory and are then no longer industrially acceptable. Since the addition of the ketone (VI) to the imine (X) of the chiral acids (VII) that is formed in situ in the reaction mixture is not significantly asymmetrically induced, the ratio of the Mannich salts (III):(III A) in the solution is about 1:1. The optical purity in the Mannich salt (III) that has crystallized out also rises continuously over the entire course of the reaction.

The chiral acids of the process step 1 according to the invention may be obtained virtually quantitatively in a simple manner and in unchanged optical purity, and be reused in the next batch. Multiple reuse of the chiral auxiliary (VII) on repeated batchwise performance of the process step 1 means that the Mannich salt (III) can be prepared with substantially less than 0.35 mol % of (VII) gross. B. List (J. Am. Chem. Soc. 2000, 122, 9336–9337) also reports that the reaction only succeeds with proline and fails with even very closely related analogs of proline.

In contrast, owing to its different type of mechanism, the process step 1 according to the invention succeeds with a very wide variety of sometimes very structurally different acids (VII). For example, Tables 2 to 5 show that the same Mannich base could be prepared in high optical purity using (S)-(+)-mandelic acid, (+)-dipivaloyltartaric acid or (L)-(−)-malic acid. It is also of industrial interest that (S)-(+)-mandelic acid and (L)-(−)-malic acid have a price comparable to that of (L)-proline, but the enantiomeric compounds (R)-(−)-mandelic acid and (D)-(+)-malic acid are substantially cheaper than (D)-proline. Significant advantages of the present process step 1 over the List reaction are the very wide variety of usable solvents, the isolation of the optically active Mannich salt (III) without workup (by simple filtration), and the high isolated chemical yields (85–95% of theory). These properties are all confirmed by the examples in Tables 2 to 5.

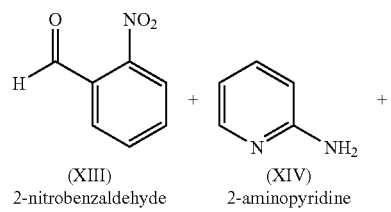

(XIII)
2-nitrobenzaldehyde (XIV)
2-aminopyridine

-continued

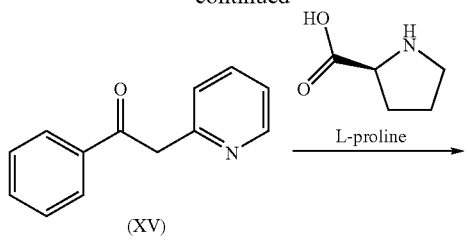

(XV)

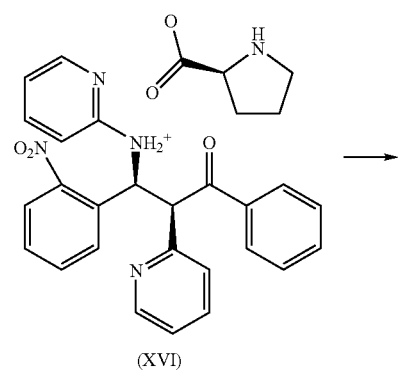

(XVI)

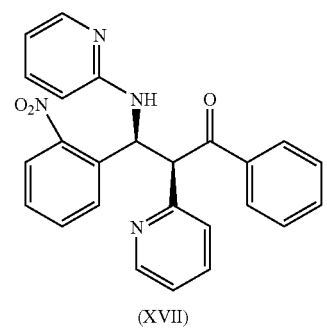

(XVII)

An asymmetric Mannich reaction experiment to give a compound of formula (III) wherein $R^1$ is o-nitrophenyl, $R^2$ is 2-pyridyl, $R^3$ is H, $R^4$ is 2-pyridyl and $R^5$ is phenyl, and where L-proline was used as the transferor of the chiral information, was carried out by weighing 493 mg (1.00 equiv.) of the ketone of formula (XV), 294 mg (1.25 equiv.) of 2-aminopyridine (XIV) and 453 mg (1.20 equiv.) of 2-nitrobenzaldehyde (XIII) into each of the 8 glass reactors of a Surveyor Reaction Screening System. Also, 101 mg (0.35 equiv.) of L-proline were weighed into each of reactors 1–5 and 7, and 576 mg (2.00 equiv.) of L-proline were each weighed into reactors 6 and 8. 10 mL of the solvent specified in the table were then added in each case. Reactors 1–6 were stirred at room temperature (22° C.), and reactors 7–8 at 40° C. internal temperature. After the specified reaction times, withdrawn samples were derivatized with camphanoyl chloride (VIII A), and the resulting isomeric amides (XVII), (XVII A), the anti-isomer of (XVII), and the anti-isomer of (XVII A) were quantified by HPLC.

Table 6 shows the results of an attempted asymmetric Mannich reaction using L-proline.

TABLE 6

| (XVII) | ent-(XVII) | trans-(XVII) | ent-trans-(XVII) | t [h] | T [° C.] | No. | Solvent | Molar equiv. of L-proline |
|---|---|---|---|---|---|---|---|---|
| — | — | — | — | 19 | 22 | 1 | Aceton | 0.35 |
| — | — | — | — | 40.5 | | | | |
| — | — | — | — | 53 | | | | |
| — | — | — | — | 131 | | | | |
| 49.7 | 47.8 | 1.2 | 1.2 | 19 | 22 | 2 | Methanol | 0.35 |
| 51.1 | 47.6 | 0.6 | 0.7 | 40.5 | | | | |
| 51.9 | 47.4 | 0.3 | 0.5 | 53 | | | | |
| 56.0 | 43.7 | 0.1 | 0.2 | 155 | | | | |
| — | — | — | — | 19 | 22 | 3 | DMSO | 0.35 |
| — | — | — | — | 40.5 | | | | |
| — | — | — | — | 53 | | | | |
| — | — | — | — | 131 | | | | |
| — | — | — | — | 19 | 22 | 4 | Dichloromethane | 0.35 |
| 19.1 | 19.1 | 24.3 | 37.6 | 40.5 | | | | |
| 23.3 | 21.6 | 24.1 | 31.0 | 53 | | | | |
| 24.9 | 22.6 | 23.1 | 29.4 | 131 | | | | |
| 50.5 | 49.5 | — | — | 19 | 22 | 5 | Ethanol | 0.35 |
| 48.9 | 47.1 | 1.7 | 2.3 | 40.5 | | | | |
| 49.5 | 47.9 | 1.1 | 1.6 | 53 | | | | |
| 55.3 | 43.8 | 0.4 | 0.5 | 155 | | | | |
| 48.9 | 45.9 | 2.4 | 3.4 | 19 | 22 | 6 | Ethanol | 2.00 |
| 48.4 | 47.4 | 1.6 | 2.5 | 40.5 | | | | |
| 49.5 | 46.7 | 1.6 | 2.2 | 53 | | | | |
| 54.1 | 45.4 | 0.3 | 0.1 | 155 | | | | |
| 50.4 | 48.0 | 0.7 | 0.8 | 18 | 40 | 7 | Ethanol | 0.35 |
| 54.9 | 45.1 | — | — | 131 | | | | |
| 49.8 | 48.7 | 0.6 | 0.8 | 18 | 40 | 8 | Ethanol | 2.00 |
| 52.6 | 44.7 | 2.4 | 0.3 | 131 | | | | |

Under the conditions explicitly described in J. Am. Chem. Soc. 2000, 122, 9336–9337 and under closely related variants of these conditions, no preparatively usable results are achieved. Under the preferred conditions (35 mol % of (L)-proline in acetone or DMSO solvent at room temperature), neither the Mannich base nor its enantiomer had been formed in significant amounts after reaction times of from 19 hours to 131 hours (Table 6, No. 1 and 3). In the methanol and ethanol solvents not specified by List, the use of 35 mol % of (L)-proline at room temperature leads to the formation of the virtually racemic Mannich base within 19 hours (Table 6, No. 2 and 5). Only on continued stirring of the reaction mixture over 155 hours does the Mannich base formed attain a low, but significant enantiomeric excess (approx. 12% ee) with the simultaneous disappearance of the small amounts of the trans-isomer originally present (Table 6, No. 2 and 5). An increase in the reaction temperature (ethanol, 40° C.) does not increase the enantiomeric excess of the Mannich base achieved after 131 hours (Table 6, No. 7). Even using 200 mol % of (L)-proline in ethanol both at room temperature and at 40° C. results in only a small optical purity of the Mannich base obtained (8–9% ee, Table 6, No. 6 and 8). When 35 mol % of (L)-proline are used in a dichloromethane solvent at room temperature, there is approximately twice as much trans-isomer as the desired cis-isomer of the Mannich base up to a reaction time of 40 hours. Only after 131 h have the amounts of trans- and cis-isomer become equal. No significant enantiomeric excesses are achieved by either diastereomer over the entire period (Table 6, No. 4).

Conditions have also been found under which a β-aminoketone of formula (I) can be obtained from the compound of formula (III) without significant loss of the stereochemical purity.

The invention further relates to a process for preparing an optically active β-aminoketone (Mannich base) of formula (I) or its enantiomer

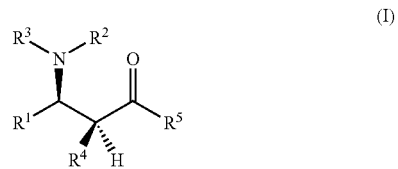

(I)

wherein $R^1$ is hydrogen;
  tert-butyl; or
  aryl or heteroaryl;

$R^2$, $R^3$ and $R^4$ are each, independently,
  hydrogen;
  $(C_1-C_7)$alkyl, optionally substituted by aryl;
  $(C_3-C_7)$cycloalkyl; or
  aryl or heteroaryl;

and $R^5$ is aryl or heteroaryl;

comprising
reacting a compound of formula (III)

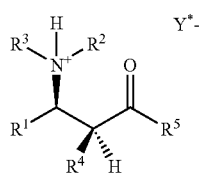

(III)

wherein $R^1$, $R^2$, $R^3$, $R^4$ and $R^5$ are as defined above, and $Y^{*-}$ is the conjugate base of an optically active organic Brønsted acid, with a base in a solvent.

The conversion of a compound of formula (III) to a compound of formula (I) is referred to hereinbelow as process step 2.

Suitable bases are organic amines, preferably ($C_1$–$C_{10}$) trialkylamines, preferably ($C_1$–$C_3$)trialkylamines, for example triethylamine or diisopropylethylamine, and also alkali metal or alkaline earth metal hydrocarbonates, carbonates or hydroxides.

Suitable solvents are water or organic solvents, or a mixture of water with an organic solvent, optionally a solubility-enhancing additive, for example comprising a phase transfer catalyst, where organic solvents may be present in 100% purity or in technical quality, and may be, for example, a $C_1$–$C_8$-alcohol, branched or unbranched, for example methanol, ethanol, n-propanol, isopropanol or n-butanol, or a ketonic solvent, for example acetone or methyl ethyl ketone (MEK), or an ester, for example ethyl acetate or n-butyl acetate, or an ether, for example tetrahydrofuran, methyl tert-butyl ether, diisopropyl ether, 1,2-dimethoxyethane or diethylene glycol dimethyl ether (diglyme), or a hydrocarbon, aliphatic or aromatic, for example toluene, or a supercritical medium, for example supercritical carbon dioxide or a halogenated hydrocarbon, for example dichloromethane, or a polar, aprotic solvent, for example DMF, DMSO or NMP.

(I) may be liberated from (III) within the temperature range from the melting point to the boiling point of the solvent (or solvent mixture), for example from −30 to 100° C., preferably from 0 to 40° C., more preferably from 0 to 25° C.

The liberation of the Mannich base (I) from the optically active Mannich salt (III) under complete retention of configuration is a nontrivial process step, since it has to be carried out under conditions under which 1. there is no deprotonation of the C—H acidic α-position to the keto function in (III) or (I), since this would lead to the formation of the undesired anti-diastereomer of (III) or (I), and 2. there is no retro-Mannich cleavage of (III) or (I), since this would lead to yield loss, the formation of chemical impurities, the formation of the undesired anti-diastereomer and also partial loss of the optical purity of the Mannich base (I).

The liberation may in principle be carried out in those organic solvents, preferably in acetone, in which the retro-Mannich cleavage proceeds very slowly (vide supra), with the use of bases, preferably triethylamine, diisopropylethylamine, alkali metal or alkaline earth metal hydrocarbonates or carbonates which can deprotonate the N—H acidic ammonium group, but not the C—H acidic α-position of (III) or (I).

The liberation may further be carried out in an aqueous medium, and using as bases, for example, alkali metal or alkaline earth metal hydrocarbonates, carbonates or hydroxides, preferably under pH-stat conditions at a pH of approx. 8–9. Preference is given to sodium hydrocarbonate or sodium hydroxide under pH-stat conditions at a pH of approx. 8–9, and particular preference is given to sodium hydroxide.

Since the solubility both of the Mannich salts (III) and of the free Mannich bases (I) is usually very low in weakly basic water, the liberation reaction leads to conversion of a suspension of the salt (III) to a suspension of free Mannich base (I). After the end of the reaction, the product (I) may therefore be isolated by simple centrifugation or filtration. Owing to the low solubility, only a very small proportion of the reactant (III) is ever present in solution, and only for a short time, since the free base (I) formed precipitates out again immediately. For this reason, the retro-Mannich reaction plays virtually no role in aqueous media. The isolated yield of free base (I) in the cases investigated was 95–100% of theory, the content of the anti-diastereomer under the optimized conditions at 0.7–1.5% was unchanged within the margin of error compared to that of the Mannich salt (III) used, and the enantiomeric excess of (I) in the optimized procedure fell by less than or equal to 2%, preferably 1%, ee compared to the salt (III) (Table 7).

In the case of salts of formula (III) that are insufficiently soluble in pure water to be deprotonated by bases such as $NaOH$ or $NaHCO_3$ or $Na_2CO_3$ at a usable rate to give (I), one or more organic, water-miscible solvents may be added in amounts of <25% by volume, preferably 1–10% by volume, more preferably 5–10% by volume (for example methanol, ethanol, isopropanol, n-propanol, acetone, tetrahydrofuran). Preference is given to adding 1–10% by volume of the cosolvent to the solvent in which the preceding four-component coupling (process step 1) has been carried out, as long as this solvent is water-miscible. Particular preference is given to use methanol, ethanol, n-propanol or isopropanol both as the solvent for the four-component coupling and as the cosolvent for the liberation of (I) in the aqueous medium. Very particular preference is given to use the Mannich salt (III) dampened with alcohol, as obtained in the centrifugation, without preceding drying, for the liberation in the aqueous medium. Whether, and to what extent an organic cosolvent has to be added to the aqueous suspension of (III) depends upon the solubility and aqueous wettability of (III), and also upon the nature of its substituents $R^1$ to $R^5$ and its anion $Y^{*-}$. Preference is given to minimize the cosolvent addition to such an extent as can be reconciled with an acceptable liberation rate under pH-stat conditions. An unnecessarily high cosolvent addition to the aqueous medium may reduce the isolated yields of free Mannich base (I) or make a more complicated isolation of (I) necessary (distilling the cosolvent out of the reaction suspension before centrifuging off the solid for the purposes of complete precipitation of (I) in the suspension). Also, an unnecessarily high cosolvent addition may promote the retro-Mannich reaction during the liberation under pH-stat conditions and thus worsen yields, chemical purity, diastereomeric purity and enantiomeric purity of the product (I).

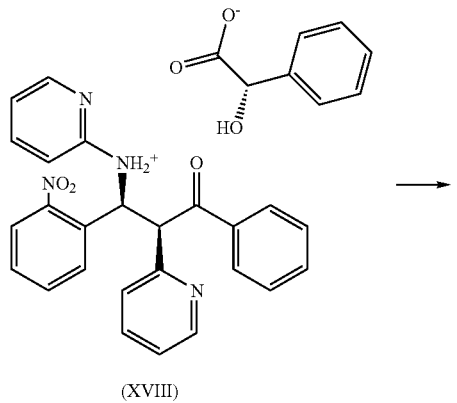

(XVIII)

-continued

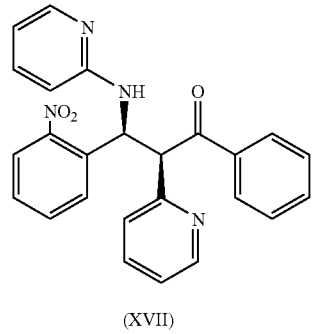

(XVII)

The liberation of a Mannich base of formula (I) is illustrated hereinbelow using the example of a reaction of a compound of formula (I) wherein $R^1$ is o-nitrophenyl, $R^2$ is 2-pyridyl, $R^3$ is H, $R^4$ is 2-pyridyl and $R^5$ is phenyl (compound of formula (XVII)), in which (XVII) has been liberated from the corresponding mandelate salt of formula (XVIII) under various conditions.

Table 7 shows the results of the conversion of the compound (XVIII) to compound (XVII):

TABLE 7

| No | Reactant (XVIII) mmol | Reactant (XVIII) trans content (NMR) ee (piv derivative) ee (camph derivative) | Base (mmol) equiv. | Solvent [mL] | Solvent addition [mL] | Experimental description | Degree of liberation (NMR) [%] | Product (XVII) isolated yield [% of theory] | Product (XVII) ee [%] (camph. derivative) | Product (XVII) ee [%] (piv derivative) | trans-isomer content (NMR) [%] | H2O content (Karl-Fischer titration) [%] |
|---|---|---|---|---|---|---|---|---|---|---|---|---|
| 1 | 1.7 | 1.4% trans ee (camph.): 96.2% ee (piv.): not determined | NaOH 2N (1.9) 1.1 | H2O 5 | none | Mandelate salt (XVIII) susp. in H2O, 2N NaOH added all at once at RT, stirred for 14 h -> beige-yellow susp., filtered off with suction, washed with H2O, dried | 100 | 96.5 | 96.0 | 98.2 | approx. 10 | |
| 2 | 35 | 1.4% trans ee (camph.): 96.2% ee (piv.): n.d. | NaOH 2N (38) 1.1 | H2O 100 | none | Mandelate salt (XVIII) susp. in H2O, 2N NaOH added all at once at RT, stirred for 14 h -> beige-yellow susp., filtered off with suction, washed with H2O, dried | 100 | 98.8 | 91.4 | 94.8 | 9.1 | 0.4 |
| 3 | 1.7 | 1.4% trans ee (camph.): 96.2% ee (piv.): n.d. | NaOH 2N (1.64) 0.95 | H2O 5 | none | Mandelate salt (XVIII) susp. in H2O, 2N NaOH added all at once at 0° C., stirred and heated for 14 h -> beige-yellow susp., filtered off with suction, washed with H2O, dried | 100 | 99.4 | 79.5 | | 5.3 | |
| 4 | 1.7 | 1.4% trans ee (camph.): 96.2% ee (piv.): n.d. | NaOH 2N (1.73) 1.0 | H2O 5 | none | Mandelate salt (XVIII) susp. in H2O, 2N NaOH added all at once at 0° C., stirred and heated for 14 h -> beige-yellow susp., filtered off with suction, washed with H2O, dried | 100 | 100 | 91.8 | | 6.2 | |
| 5 | 1.7 | 1.4% trans ee (camph.): 96.2% ee (piv.): n.d. | NaOH 2N (1.81) 1.1 | H2O 5 | none | Mandelate salt (XVIII) susp. in H2O, 2N NaOH added all at once at 0° C., stirred and heated for 14 h -> beige-yellow susp., filtered off with suction, washed with H2O, dried | 100 | 96.5 | 93.0 | | 7.0 | |

TABLE 7-continued

| No | Reactant (XVIII) mmol | Reactant (XVIII) trans content (NMR) ee (piv derivative) ee (camph derivative) | Base (mmol) equiv. | Solvent | Solvent [mL] | Solvent addition [mL] | Experimental description | Degree of liberation (NMR) [%] | Product (XVII) isolated yield [% of theory] | Product (XVII) ee [%] (camph. derivative) | Product (XVII) ee [%] (piv derivative) | trans-isomer content (NMR) [%] | H$_2$O content (Karl-Fischer titration) [%] |
|---|---|---|---|---|---|---|---|---|---|---|---|---|---|
| 6 | 8.7 | 1.4% trans ee (camph.): 96.2% ee (piv.): n.d. | NaOH 2N (9.54) 1.1 | H$_2$O | 25 | none | Mandelate salt (XVIII) susp. in H$_2$O, 2N NaOH added all at once at RT, stirred at RT for 1 h -> beige-yellow susp., filtered off with suction, washed with H$_2$O, dried | 20 | 96.9 taking into account the remaining amount of (XVIII) | 89.0 | | 3.7 | 0.2 |
| 7 | 8.7 | 1.4% trans ee (camph.): 96.2% ee (piv.): n.d. | NaOH 2N (9.54) 1.1 | H$_2$O | 25 | none | Mandelate salt (XVIII) susp. in H$_2$O, 2N NaOH added all at once at RT, stirred at RT for 1 h -> beige-yellow susp., filtered off with suction, washed with H$_2$O/EtOH, dried | 19 | 94.3 taking into account the remaining amount of (XVIII) | 96.2 | | 1.3 | 0.3 |
| 8 | 8.7 | 1.4% trans ee (camph.): 96.2% ee (piv.): n.d. | NaOH 2N (9.54) 1.1 | H$_2$O | 25 | none | Mandelate salt (XVIII) susp. in H$_2$O, 2N NaOH added all at once at RT, stirred at RT for 3 h -> beige-yellow susp., pH 11, filtered off with suction, washed with H$_2$O, dried | 78 | 97.5 taking into account the remaining amount of (XVIII) | 82.2 | | 9.1 | 0.7 |
| 9 | 8.7 | 1.4% trans ee (camph.): 96.2% ee (piv.): n.d. | NaOH 2N (9.54) 1.1 | H$_2$O | 25 | none | Mandelate salt (XVIII) susp. in H$_2$O, 2N NaOH added all at once at RT, stirred at RT for 5.5 h -> beige-yellow susp., pH 7.5, filtered off with suction, washed with H$_2$O, dried | 100 | 94.0 | 91.8 | 95.5 | 8.9 | 0.7 |
| 10 | 8.7 | 1.4% trans ee (camph.): 96.2% ee (piv.): n.d. | NaOH 2N (9.54) 1.1 | H$_2$O | 25 | none | Mandelate salt (XVIII) susp. in H$_2$O, 2N NaOH added all at once at RT, stirred at RT for 21.5 h -> beige-yellow susp., pH 7.5, filtered off with suction, washed with H$_2$O, dried | 100 | 95.6 | 93.5 | 96.6 | 8.9 | 1.5 |
| 11 | 8.7 | 1.4% trans ee (camph.): 96.2% ee (piv.): n.d. | NaOH 2N (9.54) 1.1 | H$_2$O | 25 | none | Mandelate salt (XVIII) susp. in H$_2$O, 2N NaOH added all at once at RT, stirred at RT for 21.5 h -> beige-yellow susp., pH 7.5, filtered off with suction, washed with H$_2$O/EtOH, dried | 100 | 95.4 | 92.3 | 96.2 | 8.2 | 0.9 |
| 12 | 8.7 | 1.4% trans ee (camph.): 96.2% ee (piv.): n.d. | NaHCO$_3$ (17.34) 2.0 | H$_2$O | 25 | none | Mandelate salt (XVIII) susp. in H$_2$O, NaHCO$_3$ added all at once at 0° C., stirred at 0° C. for 14 h -> yellow susp., pH 8.5, filtered off with suction, washed with H$_2$O, dried | 2.4 | 100.2 taking into account the remaining amount of (XVIII) | | 97.4 | 1.5 | |
| 13 | 8.7 | 1.4% trans ee (camph.): 96.2% ee (piv.): n.d. | NaOH 2N (9.1) 1.05 | H$_2$O | 25 | none | Mandelate salt (XVIII) susp. in H$_2$O, 2N NaOH metered in within 5 h at 0° C., stirred at 0° C. for 19 h -> beige-yellow susp., pH 11, filtered off with suction, washed with H$_2$O, dried | 13 | 98.6 taking into account the remaining amount of (XVIII) | | | | 2.5 |
| 14 | 8.7 | 1.4% trans ee (camph.): 96.2% ee (piv.): n.d. | NaHCO$_3$ (17.34) 2.0 | H$_2$O | 25 | Acetone 1.25 | Mandelate salt (XVIII) susp. in H$_2$O, NaHCO$_3$ then acetone added at 0° C., stirred at 0° C. for 23 h -> yellow susp., pH 9.5, filtered off with suction, washed with H$_2$O, dried | 100 | 95.6 | 96.4 | 97.0 | Sample 4 h 1.4 1.9 | 0.5 |

TABLE 7-continued

| No | Reactant (XVIII) mmol | Reactant (XVIII) trans content (NMR) ee (piv derivative) ee (camph derivative) | Base (mmol) equiv. | Solvent [mL] | Solvent addition [mL] | Experimental description | Degree of liberation (NMR) [%] | Product (XVII) isolated yield [% of theory] | Product (XVII) ee [%] (camph. derivative) | Product (XVII) ee [%] (piv derivative) | trans-isomer content (NMR) [%] | $H_2O$ content (Karl-Fischer titration) [%] |
|---|---|---|---|---|---|---|---|---|---|---|---|---|
| 15 | 8.7 | 1.4% trans ee (camph.): 96.2% ee (piv.): n.d. | NaOH 2N (9.1) 1.0 | $H_2O$ 25 | none | Mandelate salt (XVIII) susp. in $H_2O$, 2N NaOH metered in within 5 h at 0° C., stirred at 0° C. for 15 h –> beige-yellow susp., pH 12, filtered off with suction, washed with $H_2O$, dried | 10.7 | 98.4 taking into account the remaining amount of (XVIII) | | | 1.4 | 0.3 |
| 16 | 104 | 1.4% trans ee (camph.): 96.2% ee (piv.): n.d. | NaHCO$_3$ (208.1) 2.0 | $H_2O$ 300 | Acetone 15 | Mandelate salt (XVIII) susp. in $H_2O$, NaHCO$_3$ then acetone added at 0° C., stirred at 0° C. for 19 h –> yellow susp., pH 8.5, filtered off with suction, washed with $H_2O$, dried | Sample after 1 h 26.5 3 h 39.8 20 h 90.4 | 98.5 | | 94.0 | Sample 1 h 1.5 3 h 1.7 20 h 2.0 | 0.5 |
| 17 | 8.7 | 1.6% trans ee (camph.): 96.3% ee (piv.): 96.3% | NaHCO$_3$ (17.34) 2.0 | $H_2O$ 25 | Acetone 2.5 | Mandelate salt (XVIII) susp. in $H_2O$, NaHCO$_3$ then acetone added at 0° C., stirred at 0° C. for 20 h –> yellow susp., pH 8.5, filtered off with suction, washed with $H_2O$, dried | 97.5 | 98.6 | | 95.9 | 1.4 | 0.1 |
| 18 | 8.7 | 1.6% trans ee (camph.): 96.3% ee (piv.): 96.3% | NaHCO$_3$ (17.34) 2.0 | $H_2O$ 25 | Acetone 2.5 | Mandelate salt (XVIII) susp. in $H_2O$, NaHCO$_3$ then acetone added at RT, stirred at RT for 19 h –>yellow susp., pH 8.5, filtered off with suction, washed with $H_2O$, dried | 100 | 98.6 | | 96.0 | 1.4 | 0.2 |
| 19 | 8.7 | 1.6% trans ee (camph.): 96.3% ee (piv.): 96.3% | NaHCO$_3$ (17.34) 2.0 | $H_2O$ 25 | Ethanol 2.5 | Mandelate salt (XVIII) susp. in $H_2O$, NaHCO$_3$ then EtOH added at RT, stirred at RT for 21 h –> yellow susp., pH 9.5, filtered off with suction, washed with $H_2O$, dried | 100 | 105 | | 97.0 | 0.7 | 0.3 |
| 20 | 43 | 1.6% trans ee (camph.): 96.3% ee (piv.): 96.3% | NaOH 2N (21.48) 0.99 | $H_2O$ 125 | Ethanol 12.5 | Mandelate salt (XVIII) susp. in $H_2O$/EtOH, 2N NaOH metered in at pH-stat 8.5, stirred at RT for 4 h –> yellow susp., pH 9.5, filtered off with suction, washed with $H_2O$, dried | 100 | 98.4 | | 96.7 | 1.0 | 0.6 |
| 21 | 2274 | ? % trans ee (camph.): 93.4% ee (piv.) is n.d. | NaOH 2N (2.280) 1.002 | $H_2O$ 5686 | Ethanol 569 | Mandelate salt (XVIII) susp. in $H_2O$/EtOH, 2N NaOH metered in at pH-stat 8.5, stirred at RT for 21 h –> yellow susp., pH 8.7, filtered off with suction, washed with $H_2O$, dried | 100 | 99.5 | | 95.6 | 1.2 | 0.6 |
| 22 | 520 | 1.6% trans ee (camph.): 96.3% ee (piv.): 96.3% | NaHCO$_3$ (1040.4) 2.0 | $H_2O$ 1500 | Acetone 150 | Mandelate salt (XVIII) susp. in $H_2O$, NaHCO$_3$ then 5% of acetone added at 0° C., stirred for 18 h, 5% of acetone added, stirred at 0° C. for 20 h, at RT for 5 h –> yellow susp., filtered off with suction, washed with $H_2O$, dried | Sample after 18 h 50 23 h 94.75 25 h 99.13 100 | 101.4 | | 95.2 | <1 | 0.5 |
| 23 | 397 | ? % trans ee (camph.): 95.7% ee (piv.): | NaHCO$_3$ (793.24) 2.0 | $H_2O$ 1143 | Acetone 114 | Mandelate salt (XVIII) susp. in $H_2O$, NaHCO$_3$ and acetone added at 10° C., stirred at 10° C. for | Sample after 4.5 h 84.6 | 99.9 | 96.8 | 96.2 | <1 | 0.3 |

TABLE 7-continued

| No | Reactant (XVIII) mmol | Reactant (XVIII) trans content (NMR) ee (piv derivative) ee (camph derivative) | Base (mmol) equiv. | Solvent Solvent [mL] | Solvent addition [mL] | Experimental description | Degree of liberation (NMR) [%] | Product (XVII) isolated yield [% of theory] | Product (XVII) ee [%] (camph. derivative) | Product (XVII) ee [%] (piv derivative) | trans-isomer content (NMR) [%] | H₂O content (Karl-Fischer titration [%] |
|---|---|---|---|---|---|---|---|---|---|---|---|---|
| | | 95.6% | | | | 19 h -> yellow susp., filtered off with suction, washed with H₂O, dried | 7.5 h 90.9 approx. 22 h 100 100 | | | | | |
| 24 | 17 | 0.9% trans ee (camph.): 94.6% ee (piv.): 95.2% | NaHCO₃ (34.75) 2.0 | H₂O 50 | Acetone 5 | Mandelate salt (XVIII) susp. in H₂O, NaHCO₃ and acetone added at RT, stirred at 40° C. for 2 h -> yellow susp., filtered off with suction, washed with H₂O, dried | 100 | 96.7 | 94.8 | 94.8 | 1.2 | |
| 25 | 33 | 1.4% trans ee (camph.): 95.7% ee (piv.) is 95.6% | NaOH 2N (31.25) 0.95 | H₂O 95 | Ethanol 9.5 | Mandelate salt (XVIII) susp. in H₂O, EtOH added at 40° C., then 2N NaOH metered in at pH-stat 8.5 (80 min at 40° C.) -> yellow susp., pH 8.7, filtered off with suction, washed with H₂O, dried | Sample after 0.5 h 68.5 1 h 96.6 1.33 h 100 | 99.6 | 94.9 | 94.1 | 1.4 | |
| 26 | 445 | ? % trans ee (camph.): 94.3% ee (piv.): 97.5% | NaOH 2N (443.83) 0.997 | H₂O 1280 | Ethanol 128 | Mandelate salt (XVIII) susp. in H₂O, EtOH added at RT, then 2N NaOH metered in at pH-stat 8.5 (3.5 h at RT, 4.5 h at 40° C.), stirred at RT for 9.5 h -> yellow susp., pH 9.2, filtered off with suction, washed with H₂O, dried | Sample after 1 h 39.3 2.5 h 70.7 6 h 91.9 8 h 96.8 10 h 100 | 99.3 | 92.8 | 92.5 | 1.5 | 0.43% |

In the reactions described in Table 7, 0.95–1.10 equiv. of 2N sodium hydroxide solution were added all at once at 0° C. or room temperature to a suspension of (XVIII) in pure water, which resulted in the quantitative liberation of (XVII), which was, however, accompanied by the formation of from 5 to 10% of the anti-diastereomer of (XVII) (No. 1–5 and 8–11). Depending on the specific reaction conditions, the reduction in the enantiomeric excess of (XVII) was either only minimal (No. 1), slight (No. 2, 4, 5, 9–11) or distinct (No. 3 and 8). Immediately after the entire amount of sodium hydroxide solution had been added in one portion, the hydroxide ion concentration was therefore so high that not only did the desired deprotonation of the ammonium function of the Mannich salt (XVIII) occur, but the undesired deprotonation of its C—H-acidic α-position to the carbonyl group also occurred to a considerable extent.

Since the resulting enolate ion of (XVII) is not reprotonated stereospecifically, but to a similar extent on both sides of the enolate plane, both (XVII) and its anti-isomer are formed. When the stirring time after the sodium hydroxide solution addition was limited to 1 hour at room temperature, only 1.3–3.7% of the anti-isomer was formed (No. 6 and 7), but the degree of liberation in this time was only approx. 20%, and in one of the experiments, the enantiomeric excess of the salt (XVIII) (96.2% ee) also fell by 7% to only 89.0% in the free base (XVII) (No. 6).

When 2 equivalents of sodium hydrocarbonate were added at 0° C. instead of sodium hydroxide solution to the aqueous suspension of the mandelate (XVIII), only 2.4% of liberation occurred within 14 hours (No. 12), but the product filtered off with the suction as the (XVIII)/(XVII) mixture contained no increased amount of anti-isomer. Equally, only 11–13% of liberation occurred when 1 equivalent of 2N sodium hydroxide solution was metered very slowly into the purely aqueous suspension of (XVIII) over 5 hours at 0° C. (No. 13 and 15).

However, the addition of 5 or 10% by volume of acetone to the liberation using 2 equivalents of NaHCO₃ effected quantitative formation of the free base (XVII) with complete retention of the enantiomeric purity and without significant increase of the anti-isomer, not only at 0° C. (No. 14, 16, 17, 22), but also at 10° C. (No. 23), at room temperature (No. 18), and at 40° C. (No. 24). Marginally even better results were achieved using sodium hydrocarbonate in water/ethanol (10:1) at room temperature (No. 19).

Equally good results were achieved when 0.95–1.00 equivalent of 2N sodium hydroxide solution was metered at pH 8.5 (using an autoburette under pH-stat conditions) into the suspension of (XVIII) in water/ethanol (10:1) (No. 20, 21, 25, 26). Retention of the enantiomeric and diastereomeric purity appeared to be slightly better at room temperature (No. 20 and 21) than at 40° C. (No. 25 and 26).

The process step 2 according to the invention offers the possibility of substantially recovering in unchanged enantiomeric purity the optically active acid HY* of formula (VII) used during the four-component coupling from the weakly basic, aqueous mother liquor of the liberation reaction. The preferred method for this purpose depends upon the solubility, and also on the chemical and optical stability of the chiral acid in aqueous acidic media. In the case of acids (VII) that are very insoluble in water at approx. pH 3, it is generally sufficient to acidify the mother liquor and centrifuge off or filter off the precipitated solid (VII). When an α-amino acid has been used as the chiral acid (VII), it is generally sufficient to acidify the aqueous mother liquor of the liberation step to the isoelectric point of the α-amino acid and then to centrifuge off or filter off the solid. When the chiral acid (VII) has a not inconsiderable water solubility, as in the case, for example, of tartaric acid, malic acid or mandelic acid, or there is a risk of partial racemization under too strongly acidic conditions, the preferred recovery method is frequently extraction from the weakly acidified aqueous mother liquor. For example, the recovery of (S)-(+)-mandelic acid by ethyl acetate extraction succeeds in 88% yield, >99.5% chemical purity and 100% ee.

In the event of very high water solubility, mineral acid sensitivity or a high cost of the chiral auxiliary, other recovery methods, for example freeze drying of the neutralized aqueous mother liquor of the liberation reaction, also come into consideration.

Furthermore, a simple reduction method has been found by which β-aminoketones of formula (I) or their salts of formula (III) can be reduced with very high diastereoselectivity to 1,3-amino alcohols without losing the stereochemical purity already present in the compounds of formula (I) or (III) or having to use any chiral auxiliaries.

The present invention further relates to a process for preparing an optically active 1,3-amino alcohol of formula (II) or its enantiomer

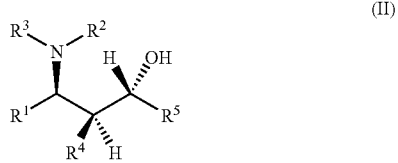
(II)

wherein
$R^1$ is hydrogen;
    tert-butyl; or
    aryl or heteroaryl;
$R^2$, $R^3$ and $R^4$ are each, independently,
    hydrogen;
    ($C_1$–$C_7$)alkyl, optionally substituted by aryl;
    ($C_3$–$C_7$)cycloalkyl; or
    aryl or heteroaryl;
and
$R^5$ is aryl or heteroaryl;

comprising
reacting a compound of formula (I)

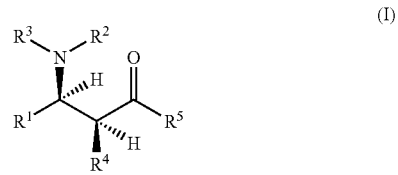
(I)

wherein $R^1$, $R^2$, $R^3$, $R^4$ and $R^5$ are as defined above or a compound of formula (III)

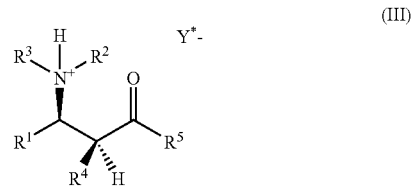
(III)

wherein $R^1$, $R^2$, $R^3$, $R^4$ and $R^5$ are as defined above, and $Y^{*-}$ is the conjugate base of an optically active organic Brønsted acid, with a reducing agent.

The compound of formula (II) may then be worked up by methods known per se.

The conversion of a compound of formula (I) to a compound of formula (II) is referred to hereinbelow as process step 3.

The conversion of a compound of formula (III) to a compound of formula (II) is referred to hereinbelow as process step 4.

Suitable reducing agents are borane or borohydride reagents, optionally in the presence of a chiral catalyst.

The process step 3 according to the invention achieves a distinct diastereoselection in the reduction of the keto group of optically active α-aminoketones (I) in favor of 1,3-amino alcohols of formula (II) when using borane or borohydride reagents.

The diastereoselective reduction of (I) to (II) may be achieved using achiral reducing agents (principle of simple diastereoselection) or in the presence of optically active catalysts, and in the latter case, the enantioselectivity of the catalytically active reagent overlaps the simple diastereoselection and usually dominates. In the case of reduction in the presence of optically active catalysts, high diastereomeric excesses are achieved when the enantioselectivity of the chiral catalyst coincides with the simple diastereoselectivity of the reduction (matched case). Lower diastereomeric excesses are obtained when the catalyst has the opposite absolute configuration and its enantioselectivity therefore counteracts the simple diastereoselectivity (mismatched case).

Examples of achiral reducing agents (principle of simple diastereoselection) include:
1. a borane-sulfide complex, for example borane-dimethyl sulfide or borane-1,4-thioxane complex;
2. a borane etherate, for example boron-tetrahydrofuran complex;
3. catecholborane;
4. a borane-sulfide complex or a borane etherate or catecholborane in the presence of a Lewis acid, for example titanium chloride triisopropoxide ($iPrO)_3TiCl$;
5. a borane-amine complex, for example borane-ammonia, borane-tert-butylamine, borane-N,N-diethylaniline, borane-N-ethyldiisopropylamine, borane-N-ethylmorpholine, borane-N-methylmorpholine, borane-morpholine, borane-piperidine, borane-pyridine, borane-triethylamine or borane-trimethylamine complexes;
6. a borane-amine complex in the presence of a Lewis acid, for example titanium chloride triisopropoxide ($iPrO)_3TiCl$;
7. a borane-phosphine complex, for example borane-tributylphosphine or borane-triphenylphosphine complexes;

8. a combination of a borohydride, preferably sodium borohydride or tetraalkylammonium borohydride, with a reagent which leads to in situ generation of borane. Examples of such combinations include sodium borohydride/iodine, sodium borohydride/boron trifluoride diethyletherate, sodium borohydride/chlorotrimethylsilane; tetraalkylammonium borohydride/alkyl halide (for example methyl iodide) in dichloromethane or the biphasic mixture of an alkyl bromide (for example n-butyl bromide) and a saturated aqueous solution of sodium borohydride and catalytic amounts (approx. 10 mol %) of a quaternary onium salt as a phase transfer catalyst (B. Jiang, Y. Feng, J. Zheng Tetrahedron Lett. 2000, 41, 10281);
9. a borohydride of a mono- or bivalent metal cation, for example sodium borohydride, lithium borohydride or zinc borohydride, or a tetraalkylammonium borohydride, in the presence or absence of a cerium (III) salt, for example $CeCl_3$, as an additive;
10. diborane ($B_2H_6$).

The following reductions, for example, may be used in the presence of one or more optically active catalysts:
1. a borohydride of a mono- or bivalent metal cation, preferably sodium borohydride, in the presence of catalytic amounts of an optically active aldiminato cobalt (II) complex, for example (1S,2S)-N,N'-bis[3-oxo-2-(2,4,6-trimethylbenzoyl)butylidene]-1,2-diphenylethylenediaminato cobalt (II) (S)-MPAC, in the presence or absence of tetrahydrofurfuryl alcohol as a coligand. This reagent combination was described by T. Makaiyama et al., Synlett 1996, 1076. It leads to a catalytic enantioselective borohydride reduction of carbonyl groups. In the case of the present novel application for reducing Mannich bases (I), the natural diastereoselectivity of sodium borohydride may be enhanced by the coinciding enantioselectivity of the reagent.
2. a borohydride of a mono- or bivalent metal cation, preferably sodium borohydride, catalyzed by a rhodium complex that results from the coordination of two molecules of optically pure 1,3-amino alcohol (II) per molecule of [($\mu^5$)-pentamethylcyclopentadienyl]rhodium dichloride dimer. It is possible and advantageous in this case to choose the substituents $R^1$ to $R^5$ in the chiral ligand (II) in such a way that they are identical with those of the resulting reduction product (II), so that the sodium borohydride reduction proceeds autocatalytically. Such catalysts differ from the CATHy™ catalysts from AVECIA (WO 98/42643), in the following points:

CATHy™ catalysts are prepared from the cyclopentadienylrhodium chloride dimer and chiral 1,2-amino alcohols, for example cis-1-amino-2-indanol. In the present application, chiral 1,3-amino alcohols are used.

CATHy™ catalysts were used for enantioselective transfer hydrogenations in which secondary alcohols, preferably isopropanol, or triethylamine/formic acid mixtures functioned as hydrogen donors. In contrast, a borohydride, preferably sodium borohydride, functions as the reducing agent in the present application.

CATHy™ catalysts were used for enantioselective transfer hydrogenations of different prochiral ketones, but not for the redution of the keto group in racemic or optically active Mannich bases (for example (I)) or their salts (for example (III)).

Preferred reducing agents are a borane-sulfide complex, a borane etherate, sodium borohydride or a sodium borohydride complex comprising an in situ catalyst that is obtained by the coordination of the [($\mu^5$)-pentamethylcyclopentadienyl]rhodium dichloride dimer to the optically active 1,3-amino alcohol (II).

Particularly preferred reducing agents are a borane-dimethyl sulfide complex or borane-tetrahydrofuran complex.

Owing to its titer stability on storage at room temperature and also to its industrial availability in high concentration (94–95% liquid), very particular preference is given to the borane-dimethyl sulfide complex.

The reaction is carried out using 0.3–10.0 molar equivalents of one of the reducing agents specified, preferably using 0.5–4.0 molar equivalents, more preferably using 1.0–2.5 molar equivalents., Process steps 3 and 4 may be effected, for example, in an aromatic hydrocarbon (for example toluene, cumene, xylene, tetralin, pyridine), a saturated hydrocarbon (for example cyclohexane, heptane, pentane), an ether (for example anisole, tetrahydrofuran, tert-butyl methyl ether, diisopropyl ether, 1,2-dimethoxyethane, 1,4-dioxane), a chlorinated hydrocarbon (for example dichloromethane, chloroform, chlorobenzene), an amide (for example N-methylpyrrolidone, N,N-dimethylacetamide), an ester (for example isobutyl acetate, butyl acetate, isopropyl acetate, propyl acetate, ethyl acetate) or a sulfoxide or sulfone (for example dimethyl sulfoxide or sulfolane) as the solvent. The last three classes of solvent are not inert toward the borane.

Preference is given to carrying out the reaction in toluene, cumene, tetrahydrofuran or anisole. Particular preference is given to toluene, cumene, or THF.

The reduction reaction is carried out in the temperature range from −70° C. to the boiling point of the solvent used, preferably 120° C., preferably at from −10° C. to +40° C., more preferably at from 0° C. to +25° C.

There exist the options of
a) adding the solution of the borane complex to the suspension or solution of the Mannich base (I) (normal addition), or
b) adding the suspension or solution of the Mannich base (I) to the initially charged solution of the borane complex (inverse addition).

The duration of the reduction reaction depends upon the specific reactant (nature of the substituents $R^1$ to $R^5$), upon the reaction temperature selected and the solubility of the reactant in the solvent. It is from approx. 30 minutes to 3 days, preferably from 1 to 5 hours, more preferably 1–2 hours.

When the particularly preferred reducing agents, borane-dimethyl sulfide or borane-THF complex are used, the primary product of the reaction is a diastereoisomer mixture of oxazaborinanes that, if desired, can be easily isolated. Formula (C) is attributed to its strongly dominating component on the basis of its HPLC behavior, its molar mass determined by HPLC/MS (M+H$^+$: m/z is 437.3) and its smooth conversion to the 1,3-amino alcohol (II) under the action of methanol/methanesulfonic acid.

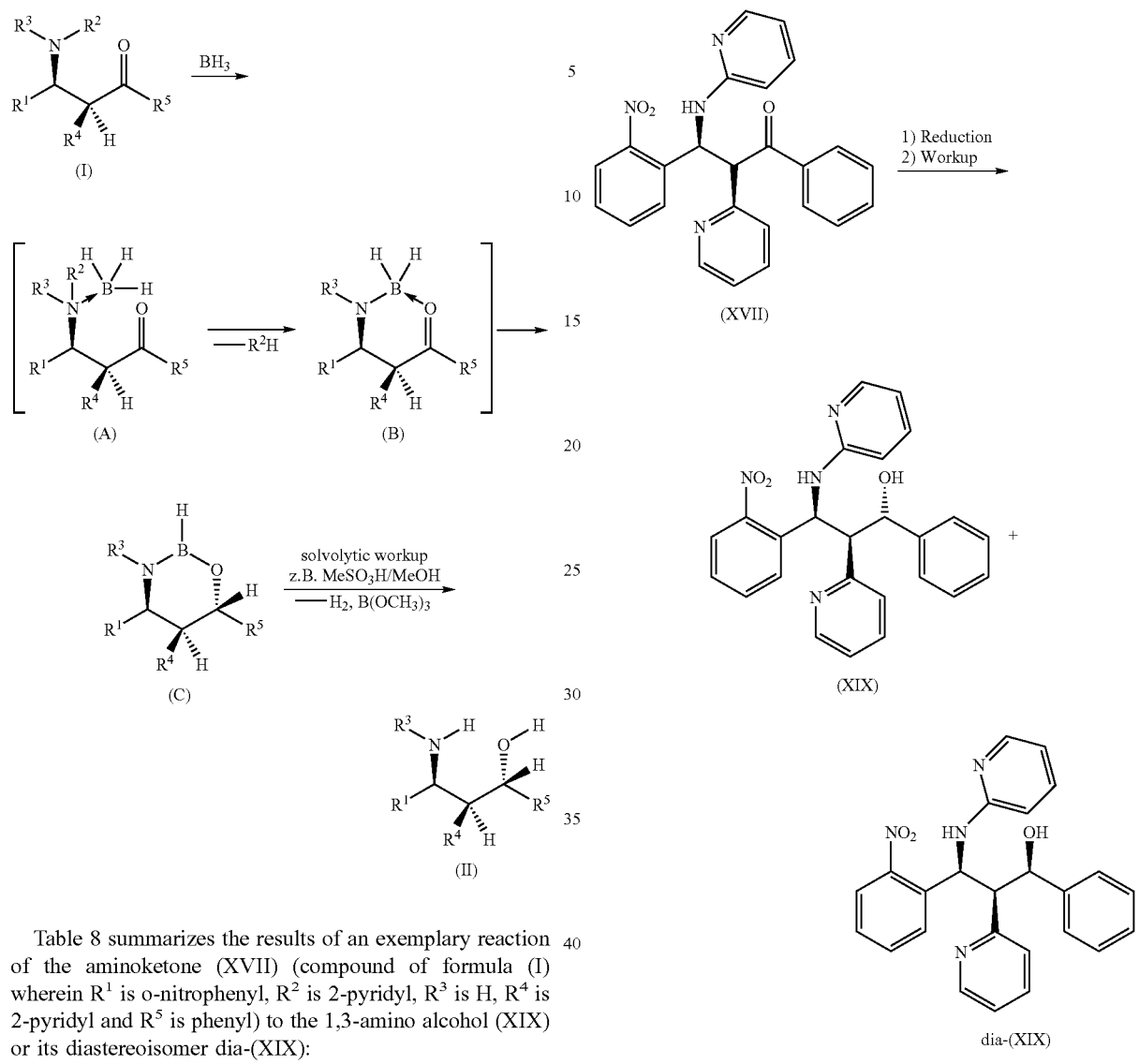

Table 8 summarizes the results of an exemplary reaction of the aminoketone (XVII) (compound of formula (I) wherein $R^1$ is o-nitrophenyl, $R^2$ is 2-pyridyl, $R^3$ is H, $R^4$ is 2-pyridyl and $R^5$ is phenyl) to the 1,3-amino alcohol (XIX) or its diastereoisomer dia-(XIX):

TABLE 8

| No. | Reactant (XVII) | BH$_3$—Me$_2$S or alternative; equivalents; addition time | Solvent (volume) | Stirring temperature and time | Workup | Ratio (XIX)/dia-(XIX), (a) | Sum of impurities, (a) | Yield % of isolated pure product (crude product) |
|---|---|---|---|---|---|---|---|---|
| 1 | racemic, 10 mmol addition as a solid in 5 × 848 mg portions, each at an interval of 1.5 h | NaBH$_4$ 1.34 initially charged | EtOH (25 mL) | RT Addition: 8 h Continued stirring: 15 h | (XVII) quant. converted. Not worked up | 69:31 | 8.0% | n.d. |
| 2 | racemic, 2 mmol of (XVII) and CeCl$_3$·7H$_2$O (2 mmol) initially charged | NaBH$_4$ 1.1 1 min | EtOH (10 mL) | 0° C. to RT 4 h | Approx. 50% of (XVII) converted. Not worked up | 83:17 | approx. 7% | n.d. |
| 3 | racemic, 2 mmol of (XVII) | BH$_3$-tert-butylamine 3.0 | MeOH (20 mL) | RT 24 h | Not worked up | 61.3:38.6 | 9.2% | n.d. |
| 4 | racemic, 2 mmol of (XVII) and (iPrO)$_3$TiCl | BH$_3$-tert-butylamine 2.2, 10 s | MeOH (20 mL) | 0° C./3 h, then RT/12 h | <50% conversion of (XVII). Not | 70:30 | | n.d. |

TABLE 8-continued

| No. | Reactant (XVII) | BH₃—Me₂S or alternative; equivalents; addition time | Solvent (volume) | Stirring temperature and time | Workup | Ratio (XIX)/dia-(XIX), (a) | Sum of impurities, (a) | Yield % of isolated pure product (crude product) |
|---|---|---|---|---|---|---|---|---|
| | (2 mmol) initially charged | | | | worked up | | | |
| 5 | racemic, 5 mmol | BH₃—THF (1:0 M) 3.0 (b) 15 min | THF (45 mL) | +1° C. 1 h overnight at RT | 2 N HCl (16 equiv.) | 87.8:12.2 | 7.7% | (103%) |
| 6 | racemic, 5 mmol | 3.0, (b) (95%) 2 min | Toluene (25 mL) | 0° C. to RT 2 h at RT | MeSO₃H (3.0 equiv.) in MeOH | 96.7:3.2 | 7.2% | (83.4%) |
| 7 | racemic, 5 mmol | 3.0, (b) (95%) 2 min | MTB Ether (25 mL) | 0° C. to RT 2.5 h at RT | MeSO₃H (3.0 equiv.) in MeOH | 94.4:5.5 | 11.7% | (105%) |
| 8 | racemic, 15 mmol | 3.0, (b) (95%) 2 min | Toluene (75 mL) | 0° C. to RT 1.75 h at RT | 2 N HCl (9 equiv.) | Slight cleavage of the oxazaborinane | | n.d. |
| 9 | racemic, 15 mmol | 3.0, (b) (95%) 5 min | Toluene (75 mL) | 0° C. to RT 2.5 h at RT | MeSO₃H (3.0 equiv.) in MeOH | 97.0:3.0 | 4.7% | (85.8%) |
| 10 | racemic, 15 mmol | 2.0, (b) (95%) 3 min | Toluene (150 mL) | 0° C. to RT 2.5 h at RT | MeSO₃H (3.0 equiv.) in MeOH | 95.9:4.0 | 7.1% | (87.5%) |
| 11 | 30 mmol, of which approx. 10% is mandelate (XVIII), 94.0% ee | 3.0, (b) (95%) 3 min | Toluene (150 mL) | 0° C. to RT 2.25 h at RT | MeSO₃H (3.0 equiv.) in MeOH | 97.1:2.8 | 2.8% | (95.8%) |
| 12 | 30 mmol, of which approx. 10% is mandelate (XVIII), 94.0% ee | 3.0, (b) (95%) 2 min | Toluene (150 mL) | 0° C. to RT 2.5 h at RT | MeSO₃H (3.0 equiv.) in MeOH | 96.9:3.1 | 6.0% | n.d. |
| 13 | 150 mmol, 100% (XVII) 95.2% ee 0.50% H₂O | 3.0, (c) (95%) 2 min | Toluene (750 mL) | 0° C. to RT 2 h at RT | MeSO₃H (3.0 equiv.) in MeOH | 96.5:3.4 | 4.2% | (106.2%) (d) (84.2%) (e) |
| 14 | 30 mmol, 100% (XVII) 95.2% ee 0.50% H₂O | 3.0, (c) (95%) 1 min | Toluene (150 mL) | +1° C. 2.25 h | MeSO₃H (3.0 equiv.) in MeOH | 96.7:3.2 | 5.3% | (97.3%) |
| 15 | 30 mmol, 100% (XVII) 95.2% ee 0.50% H₂O | 2.0, (c) (95%) 1 min | Toluene (150 mL) | +1° C. 4 h | MeSO₃H (2.0 equiv.) in MeOH | 96.4:3.5 | 11.5% | (97.0%) |
| 16 | 30 mmol, 100% (XVII) 95.2% ee 0.50% H₂O | 2.0, (c) (95%) 0.5–1 min | Toluene (150 mL) | 0° C. to RT 2.25 h at RT | MeSO₃H (2.0 equiv.) in MeOH | 95.9:4.0 | 8.6% | (96.4%) |
| 17 | 30 mmol, 100% (XVII) 95.2% ee 0.50% H₂O | 2.5, (c) (95%) 0.5–1 min | Toluene (150 mL) | 0° C. to RT 2.5 h at RT | MeSO₃H (2.5 equiv.) in MeOH | 96.8:3.1 | 3.1% | (98.2%) |
| 18 | 30 mmol, 100% (XVII) 95.2% ee 0.50% H₂O | 2.5, (c) (95%) 0.5–1 min | Toluene (150 mL) | 0° C. to RT 2.5 h at RT | MeSO₃H (2.5 equiv.) in MeOH | 96.6:3.3 | 4.1% | >65% |
| 19 | 388 mmol, 100% (XVII) 96.2% ee 0.32% H₂O | 2.5, (c) (95%) 0.5–1 min | Toluene (1270 mL) THF (86 mL) | 0° C. to RT | MeSO₃H (2.5 equiv.) in MeOH at +20° C. | 95.8:4.1 | 4.9% | 78% (f) >99.8% pure 100% ee |
| 20 | 50 mmol, 100% (XVII) 92.5% ee 0.43% H₂O | 2.2, (c) (95%) 0.5 min | Toluene (160 mL) | 0° C. to RT 2.25 h at RT | MeSO₃H (2.2 equiv.) in MeOH at +20° C. | 93.9:6.0 | 4.7% | 82.0% (f) 99.7% pure 100% ee 1.5% H₂O |
| 21 | 50 mmol, 100% (XVII) 92.5% ee 0.43% H₂O | 2.2, (c) (95%) 0.5 min | Toluene (250 mL) | 0° C. to RT 2 h at RT | MeSO₃H (2.2 equiv.) in MeOH at +20° C. | 94.0:5.9 | 6.8% | 81.4% (f) 99.4% pure 97.6% ee 2.0% H₂O |
| 22 | 350 mmol, 100% (XVII) 95.6% ee 0.62% H₂O | 2.2, (c) (94%) 5 min | Toluene (1120 mL) | 0° C. to RT 2 h at RT | MeSO₃H (2.2 equiv.) in MeOH at +20° C. | 93.5:6.4 | 9.2% | 81.7% (f) 99.8% pure 100% ee 1.5% H₂O |
| 23 | 50 mmol, 100% (XVII) 95.6% ee, 0.36% H₂O | 2.5, (c) (94%) initially charged in toluene | Toluene (160 mL) | 0° C. to RT 1 h at RT | MeSO₃H (2.5 equiv.) in MeOH at +20° C. | 94.1:5.8 | 4.7% | 80.3% (f) 99.5% pure 100% ee 3.4% H₂O |

TABLE 8-continued

| No. | Reactant (XVII) | BH$_3$—Me$_2$S or alternative; equivalents; addition time | Solvent (volume) | Stirring temperature and time | Workup | Ratio (XIX)/dia-(XIX), (a) | Sum of impurities, (a) | Yield % of isolated pure product (crude product) |
|---|---|---|---|---|---|---|---|---|
|  | inverse addition as a solid within 7 min |  |  |  |  |  |  |  |
| 24 | 50 mmol, 100% (XVII) 95.6% ee, 0.36% H$_2$O inverse addition as a solid within 30 min | 2.5, (c) (94%) initially charged in toluene | Toluene (160 mL) | 0° C. to RT 1 h at RT | MeSO$_3$H (2.5 equiv.) in MeOH at +20° C. | 94.3:5.6 | 4.8% | 78.9% (f) 99.4% pure 100% ee 1.2% H$_2$O |
| 25 | 150 mmol, 100% (XVII) 95.6% ee, 0.36% H$_2$O inverse addition as a solid within 50 min | 2.5, (c) (94%) initially charged in toluene | Toluene (480 mL) | 0° C. to RT 1 h at RT | MeSO$_3$H (2.5 equiv.) in MeOH at +20° C. | 93.9:6.0 | 7.0% | 80.1% (f) 99.8% pure 100% ee 3.4% H$_2$O |
| 26 | 49 mmol, 100% (XVII) 95.6% ee, 0.36% H$_2$O inverse addition as a solid within 20 min | 2.5, (c) (94%) initially charged in toluene | Toluene (160 mL) | 0° C. to RT 1.25 h at RT | MeSO$_3$H (1.5 equiv.) in MeOH at 20° C. to 40° C. | 94.4:5.5 | 4.4% | 81.4% (f) 99.8% pure 100% ee 3.63% H$_2$O |
| 27 | 50 mmol, 100% (XVII) 95.6% ee, 0.36% H$_2$O inverse addition as a solid within 17 min | 2.5, (c) (94%) initially charged in toluene | Toluene (160 mL) | 0° C. to RT 1.25 h at RT | MeSO$_3$H (1.5 equiv.) in MeOH at 20° C. to 40° C. | 94.2:5.8 | 7.6% | 74.5% (f) 99.8% pure 100% ee 3.5% H$_2$O |
| 28 | 50 mmol, 100% (XVII) 95.6% ee, 0.36% H$_2$O | 2.5, (c) (94%) 25 min | Toluene (160 mL) | 0° C. to RT 1.25 h at RT | MeSO$_3$H (1.5 equiv.) in MeOH at 20° C. to 40° C. | 94.3:5.6 | 6.4% | 75.9% (f) 99.9% pure 100% ee 1.2% H$_2$O |
| 29 | 50.39 mmol, 100% (XVII) 95.6% ee, 0.36% H$_2$O | 2.5, (c) (94%) 25 min | Toluene (160 mL) | 0° C. to RT 1.5 h at RT | MeSO$_3$H (2.0 equiv.) in MeOH at 20° C. to 40° C. | 94.3:5.6 | 6.1% | 80.3% (f) 99.8% pure 100% ee 3.6% H$_2$O |
| 30 | 200 mmol, >99% (XVII) 93.4% ee, 0.02% H$_2$O Conducted in RC1 calorimeter | 2.5, (c) (94%) 25 min | Toluene (640 mL) | 0° C. to RT 1 h at RT | (g) MeSO$_3$H (2.0 equiv.) in MeOH at 20° C. to 40° C. | 92.7:7.2 | 18.0% | 60.1% (f) 99.1% pure 100% ee 3.6% H$_2$O |
| 31 | 198.2 mmol, >99% (XVII) 93.4% ee, 0.02% H$_2$O | 2.5, (c) (94%) 22 min | Toluene (640 mL) | 0° C. to RT 1.25 h at RT | (h) MeSO$_3$H (2.5 equiv.) in MeOH at 20° C. to 40° C. | 93.5:6.4 | 11.4% | 74.2% (f) 99.2% pure 100% ee 1.3% H$_2$O |
| 32 | 200.0 mmol, >99.5% (XVII) 90.5% ee | 2.5, (c) (94%) 15 min | Toluene (640 mL) | 0° C. to RT 2.5 h at RT | (h) MeSO$_3$H (2.5 equiv.) in MeOH at 15° C. to 22° C. | 94.1:5.9 | 11.0% | 76.8% (f) 99.7% pure 99.4% ee 4.3% H$_2$O |
| 33 | 150.0 mmol, >99% (XVII) 93.4% ee, 0.02% H$_2$O | 2.6, (c) (94%) 15 min | Toluene (400 mL) | 1° to 20° C. 4 h at 20° C. | (i) MeSO$_3$H (3.2 equiv.) in MeOH at 15° C. to 22° C. | 94.4:5.6 | 11.6% | 83.7% (f) 99.7% pure 100% ee 1.3% H$_2$O |
| 34 | 15.0 mmol, >99% (XVII) 93.4% ee, 0.02% H$_2$O | Me$_3$SiCl 3.00 NaBH$_4$ 3.00 | THF (215 mL) | React Me$_3$SiCl with NaBH$_4$ at 50°/45 min; add (XVII) at 2° C.; heat to 20° within 15 min and stir at 20° for 2 h | MeSO$_3$H (3.4 equiv.) in MeOH | 94.1:5.9 | 8.5% of unconverted (XVII) and retro-Mannich product, 5.4% of dia-(XIX); sum of 14.9% of impurities | 74.8% (f) 99.6% pure 100% ee |

TABLE 8-continued

| No. | Reactant (XVII) | BH$_3$—Me$_2$S or alternative; equivalents; addition time | Solvent (volume) | Stirring temperature and time | Workup | Ratio (XIX)/dia-(XIX), (a) | Sum of impurities, (a) | Yield % of isolated pure product (crude product) |
|---|---|---|---|---|---|---|---|---|
| 35 | 150.0 mmol, >99% (XVII) 93.4% ee, 0.02% H$_2$O | 2.6, (c) (94%), 0.1 equiv. (XIX) | Toluene (400 mL) | React BMS with cat. (XIX) in tol. (40 mL) at 0–20° C./1 h. Add susp. of (XVII) in tol. (360 mL) at 2° C./15 min. Stir at 20° for 3 h. | MeSO$_3$H (3.2 equiv.) in MeOH | 94.3:5.7 | 2.4% | 75.9% 99.5% pure 100% ee 3.1% H$_2$O |
| 36 | 75.0 mmol, >99% (XVII) 93.4% ee, 0.02% H$_2$O | 2.6, (c) (94%) 0.1 equiv. (XIX) | THF (180 mL) Toluene (20 mL) | React BMS with cat. (XIX) in tol. (20 mL) at 20° C./1 h. Add THF (180 mL). At 45° C., add (XVII) within 30 min, then stir at 45° C. for 12 h | MeSO$_3$H (3.2 equiv.) in MeOH | 94.3:5.7 | 11.8% | 67.7% 99.2% pure 99.3% ee 3.9% H$_2$O |

Comments:
(a) In react. No. 5–36: HPLC analysis of the reaction mixture after completed reaction and acid solvolysis of the intermediate oxazaborinane. In react. No. 1–4: HPLC analysis of the hydroboration mixture.
(b) The amount of borane complex added was determined volumetrically (addition by graduated syringe).
(c) The amount of borane complex used was determined by weighing.
(d) Yield after precipitation out of 2 N NaOH, filtration and drying.
(e) Yield after repeated washing in DM-water, filtration and drying.
(f) After precipitation in 2 N NaOH, (XIX) was directly dissolved in n-butanol at 45–50° C., and its dihydrochloride was precipitated using 2.2 equiv. of 30% hydrochloric acid.
(g) The extraction of (XIX) with 2 N HCl was replaced by an additional addition of 1.4 equiv. of MeSO$_3$H and extraction with water.
(h) The extraction of (XIX) with 2 N HCl was replaced by an additional addition of 0.7 equiv. of MeSO$_3$H and extraction with water.
(i) Owing to the immediate use of 3.2 equiv. instead of 2.5 equiv. of MeSO$_3$H, the addition of 2 N HCl or of additional MeSO$_3$H to extract (XIX) from the toluene phase into the aqueous phase became unnecessary.

The results show that this method allows the carbonyl group to be reduced with high stereoselectivity (up to >97:<3; see No. 9 and 11) and the retro-Mannich reaction of the reactant (I) is very substantially suppressed under the reaction conditions, so that the stereochemical information already present in the reactant is virtually entirely retained.

An example of a workup method known per se for reductions with borane or borohydride reagents is the solvolytic cleavage and/or a crystallization.

The solvolytic cleavage of the oxazaborinane (C) initially formed in the reduction of (I) to the 1,3-amino alcohol (II), and its isolation from the reaction mixture leads to the greatest possible extent of removal of stereoisomers: the enantiomer ent-(II), the diastereomer dia-(II)

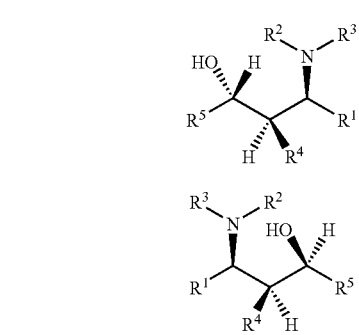

and the enantiomer of the diastereomer ent-dia-(II)

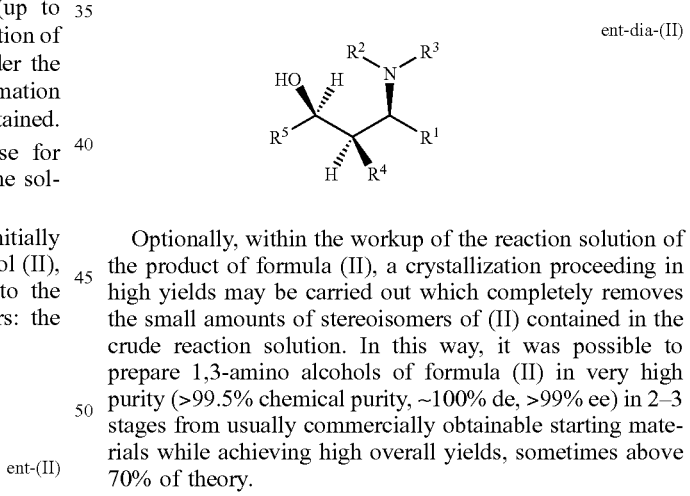

Optionally, within the workup of the reaction solution of the product of formula (II), a crystallization proceeding in high yields may be carried out which completely removes the small amounts of stereoisomers of (II) contained in the crude reaction solution. In this way, it was possible to prepare 1,3-amino alcohols of formula (II) in very high purity (>99.5% chemical purity, ~100% de, >99% ee) in 2–3 stages from usually commercially obtainable starting materials while achieving high overall yields, sometimes above 70% of theory.

The solvolytic cleavage may be achieved by a variety of different procedures:

a) Preference is given to carrying out the cleavage using 1–4 equivalents of a strong acid, more preferably methanesulfonic acid or sulfuric acid, in an excess of a low molecular weight alcohol, more preferably methanol, at 0–60° C., more preferably 15–40° C. (Table 8, No. 6–36). Under these conditions, the boron from (C) is converted to a volatile trialkyl borate ester, in the particularly preferred case to the volatile trimethyl borate B(OCH$_3$)$_3$ with forms an MeOH—B(OMe)$_3$ azeotrope with methanol of boiling point 59° C. which contains approx. 70% of B(OMe)$_3$ in the azeotropic mixture (M. Couturier et al., Tetrahedron Lett. 2001, 42, 2285). Particularly when the borane reduction has been carried out in the particularly preferred solvents such as toluene or cumene, the boric ester solvate and excess methanol can be easily distilled off quantitatively after completed solvolysis by applying a vacuum. The 1,3-amino alcohol of the general formula (II) is present in protonated form and therefore generally has good water solubility. Therefore, when water is added to the toluenic or cumenic distillation residue, the salt of (II) is in most cases virtually quantitatively extracted into the aqueous phase. The toluenic or cumenic phase then removes most reaction by-products, for example retro-Mannich products and their reduction products. When the product-containing, aqueous acidic solution is then rendered strongly basic, for example with aqueous sodium hydroxide solution, the free 1,3-amino alcohol (II) precipitates out and can easily be isolated. However, particular preference is given to isolating (II) by crystallizing one its salts while the small amounts of stereoisomers contained in the crude product remain in the mother liquor. The optimum anion and solvent for such crystallization depend upon the nature of the substituents $R^1$ to $R^5$ in (II) and therefore have to be determined independently for each 1,3-amino alcohol of formula (II). When $R^1$ is o-nitrophenyl, $R^2$ is 2-pyridyl, $R^3$ is H, $R^4$ is 2-pyridyl, and $R^5$ is phenyl, for example, the optimum crystallization of the dihydrochloride of (II) proved to be from 1-butanol. The dihydrochloride was obtained in 99.3–100% ee and a chemical purity of 99.1–99.9% in a yield of 74–84% of theory, based on the Mannich base (I) used (Table 7, No. 19–29, 31–35). This crystallization can even compensate for an untypical low enantiomeric purity of the Mannich base (I) used. In the experiment of Tab. 7, No. 32, (I) of only 90.5% ee was used. Despite this, (II) dihydrochloride was isolated in 76.8% yield with 99.4% ee and 99.7% chemical purity.

b) Alternatively, the solvolysis of (C) may be carried out using an excess of a strong aqueous acid, preferably 2-normal to concentrated hydrochloric acid or aqueous methanesulfonic acid, at 0–100° C., preferably 0–40° C., after distilling off the organic solvent of the borane reduction beforehand. This workup was applied in Table 9 (No. 4–7, 9–14 and 16–18) and in Table 10 (No. 5–8). Under these conditions, the boron from (C) is converted to boric acid $B(OH)_3$ which is only sparingly soluble in aqueous acidic reaction mixtures, in particular when cooled to 0–10° C., and very substantially crystallizes out and can therefore be easily removed. In contrast, the 1,3-amino alcohol is present in protonated form and therefore generally has good water solubility. When the product-containing, aqueous acidic solution is rendered strongly basic, for example with aqueous sodium hydroxide solution, after removing the boric acid, the free 1,3-amino alcohol (II) precipitates out and can be easily removed. Appropriate typical procedures are described in Examples 23 (corresponding to Tab. 9, No. 18) and 24 (corresponding to Tab. 10, No. 5). However, preference is given, as is the case in a), to isolating (II) by crystallizing one of its salts. This is achieved by rendering the aqueous acidic product-containing solution basic in the presence of a suitable organic water-immiscible solvent, for example n-butanol. The free 1,3-amino alcohol (II) is virtually quantitatively extracted into this organic phase which is then heated and, by adding a suitable aqueous acid, for example concentrated hydrochloric acid, a salt of (II) is formed which crystallizes out on gradual cooling of the butanolic solution.

c) A further alternative solvolysis method for (C) is the addition of an excess of the solution of an alkali metal hydroxide or alkaline earth metal hydroxide, followed by heating to 30–100° C., preferably to 50–70° C. The free 1,3-amino alcohol (II) may then be extracted with an inert organic solvent, while the alkali metal borate or alkaline earth metal borate formed remains in the aqueous phase. An appropriate typical procedure is described in Example 25 (corresponding to Table 10, No. 3).

d) A further alternative solvolysis method for (C) is the addition of an organic complexing agent (for example diethylenetriamine) which forms a strong chelate complex with the boron. Preference is given to applying this method in the following form:
Methanol is initially charged in the solvolysis reactor at 20–60° C., preferably at 40–50° C., under an inert gas atmosphere. The preferably toluenic reduction mixture (comprising substantially (C) and excess borane) at 20–60° C., preferably 40–50° C., is gradually metered into the initially charged methanol. On completion of metered addition, the complexing agent, for example diethylenetriamine, is metered in and the solvolysis mixture is stirred until the solvolysis of (C) to form (II) is quantitative. Water is then fed to the reaction mixture, preferably at 60–70° C. The organic (toluenic) phase is then separated from the aqueous phase, and washed with water, preferably at 60–70° C. The boron-amine chelate and excess methanol are removed with the aqueous phase. The amino alcohol of formula (II) can be isolated from the toluenic phase by known processes. Depending on the specific nature of the substituents $R^1$ to $R^5$, direct crystallization by gradual cooling of the warm, concentrated toluene solution may also be advantageous. However, it may also be advantageous to transfer (II), as described under a), into another more polar solvent, for example n-butanol, followed by the crystallization of a suitable salt of (II), for example a hydrochloride.

e) A further alternative cleavage method for (C) to form the 1,3-amino alcohol (II) is the solvolytic cleavage by adding hydrogen peroxide solution. This method is only advantageous for those products (II) that are not easily oxidized by hydrogen peroxide. Also, since the reaction of boranes and some oxazaborinanes of formula (II) with hydrogen peroxide may be extremely exothermic, the workup methods a) and d) are frequently preferred over e).

Process step 4 is carried out with the same reducing agents and under the same reaction conditions (molar equivalents of reducing agents, solvents which can be used, reaction temperature and duration, method of adding) and workup methods as have already been described for process step 3.

The following special features apply to process step 4:
Mannich salts of formula (III) are generally distinctly more polar than the free Mannich bases of formula (I). The solubility of the Mannich salts (III) in nonpolar solvents (toluene or less polar) is in most cases no longer sufficient for a viable reaction rate with the reducing agent. Preferred solvents for the reduction of the Mannich salts (III) are therefore relatively polar solvents in which (III) has better solubility, and particular preference is given to tetrahydrofuran.

Particularly preferred counterions $Y^{*-}$ in the Mannich salts (III) are chiral carboxylates or dicarboxylates. These counterions $Y^{*-}$ are generally not completely inert toward boranes, borane complexes or activated borohydrides and are themselves gradually reduced by the reducing agents used. This consumption has to be taken into account by an appropriate increase in the equivalents of reducing agents.

As is described for process step 3, an oxazaborinane (C) is formed as the primary reaction product and is then converted by one of the above-described solvolysis/workup procedures to the desired 1,3-amino alcohol of formula (II).

In Table 9, the results of diastereoselective carbonyl reductions of the (S)-(+)-mandelate salt (XVIII) (compound of formula (III) wherein $R^1$ is o-nitrophenyl, $R^2$ is 2-pyridyl, $R^3$ is H, $R^4$ is 2-pyridyl and $R^5$ is Ph) to the 1,3-amino alcohol (XIX) are compiled by way of example:

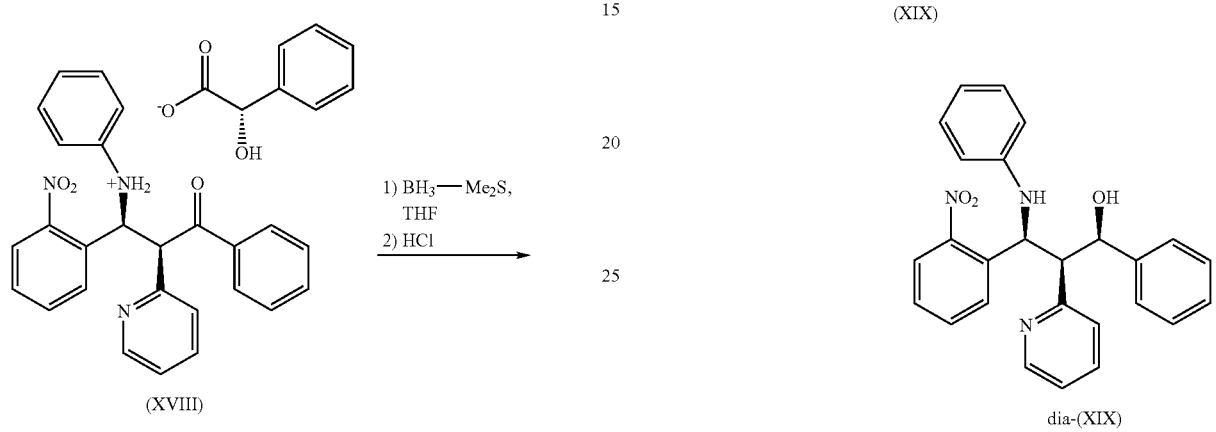

(XVIII)

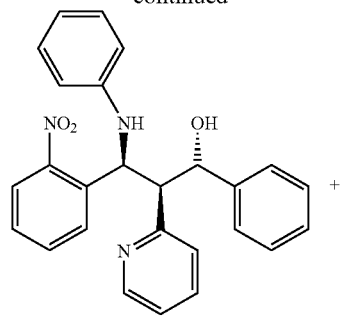

(XIX)

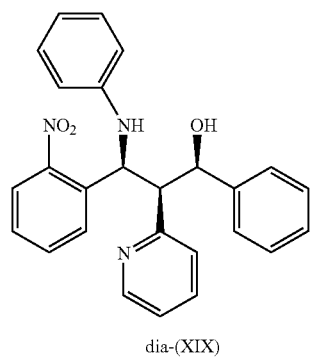

dia-(XIX)

TABLE 9

| No. | Reactant mmol optical purity | BH$_3$—Me$_2$S (equiv.) addition time | Solvent | Stirring temperature and time | Workup | Ratio of (XIX)/dia-(XIX) (HPLC of reaction mixture) | Sum of impurities (HPLC of reaction mixture) | Yield % of theory (isolated crude product) isolated pure product |
|---|---|---|---|---|---|---|---|---|
| 1 | 2 mmol 95.1% ee | 5.0 (a) 5 min | Toluene (20 mL) | +1° C. 4 h | 2 N HCl (40 equiv.) | | Unclean reaction, a lot of unconverted reactant | Batch discarded |
| 2 | 2 mmol 95.1% ee | 4.0 (a) 15 min | THF (20 mL) | +1° C. 1.25 h | 2 N HCl (40 equiv.) | 95.4:4.5 | 2.9% | n.d. |
| 3 | 2 mmol 95.1% ee | 4.0 (a) 5 min | THF (20 mL) | 0° C. to RT 1 h at RT | 2 N HCl (40 equiv.) | 95.8:4.1 | 1.9% | n.d. |
| 4 | 2 mmol 95.1% ee | 5.0 (a) 0.5 min | THF (20 mL) | 0° C. to RT 0.5 h at RT | conc. HCl (10 mL) | 96.7:3.2 | 2.7% | (>100%) |
| 5 | 15.4 mmol 95.1% ee | 5.0 (a) 30 min | THF (90 mL) | +1° C. 1 h | semiconc. HCl (60 mL) | 93.7:6.2 | 11.3% | (>100%) |
| 6 | 15.7 mmol 96.5% ee | 5.0 (a) 10 min | THF (95 mL) | 0° C. to RT 3.5 h at RT | semiconc. HCl (60 mL) | 95.8:4.1 | 4.4% | (>100%) |
| 7 | 13.9 mmol 96.5% ee | 3.0 (a) 10 min at RT (exothermic) | THF (85 mL) | RT 2.5 h | dil. HCl (70 mL) | 95:5 | >20% of decomposition products of the reactant! | Batch discarded |
| 8 | 13.9 mmol 96.5% ee | 3.0 (a) 15 min | THF (85 mL) | 0° C. to RT 1.25 h at RT | MeSO$_3$H (3.0 equiv.) in MeOH | 95.5:4.4 | 2.6% | (79.8%) |
| 9 | 13.9 mmol 96.5% ee | 3.0 (a) 10 min | THF (85 mL) | 0° C. to RT 1.75 h at RT | 30% HCl (50 mL) | 95.5:4.3 | 5.6% | 83.2% (4% dia-(XIX) and 5% by-product) |
| 10 | 13.9 mmol 96.5% ee | 3.0 (a) 10 min | THF (85 mL) | 0° C. to RT 2.5 h at RT | 30% HCl (50 mL) | 95.6:4.4 | 5.1% | (97%) |
| 11 | 13.9 mmol 96.5% ee | 3.0 (a) 7 min | THF (85 mL) | 0° C. to RT 2 h at RT | 2 N HCl (63 mL) | 96:4 | 4.1% | n.d. tacky solid |
| 12 | 24 mmol 96.5% ee | 4.0 (a) 10 min | THF (60 mL) | 0° C. to RT 3 h at RT | semiconc. HCl (22.5 mL) | 96.1:3.9 | 3.8% | (100%) |

TABLE 9-continued

| No. | Reactant mmol optical purity | BH₃—Me₂S (equiv.) addition time | Solvent | Stirring temperature and time | Workup | Ratio of (XIX)/dia-(XIX) (HPLC of reaction mixture) | Sum of impurities (HPLC of reaction mixture) | Yield % of theory (isolated crude product) isolated pure product |
|---|---|---|---|---|---|---|---|---|
| 13 | 24 mmol 96.5% ee | 4.0 (a) 10 min | THF (60 mL) | 0° C. to RT 2 h at RT | conc. HCl (30 mL) | 96.4:3.6 | 3.1% | (100.8%) |
| 14 | 74.8 mmol 96.5% ee | 4.0 (a) 10 min | THF (750 mL) | 0° C. to RT 2 h at RT | conc. HCl (375 mL) | 96.1:3.9 | 6.0% | (> 100%) |
| 15 | 11 mmol 96.5% ee | 4.0 (a) 10 min | THF (85 mL) | 0° C. to RT 2 h at RT | MeSO₃H (4.0 equiv.) in MeOH | 96.5:3.5 | 4.1% | (> 100%) |
| 16 | 15 mmol 96.5% ee | 3.0 (a) 10 min | THF (85 mL) | 0° C. to RT 1.5 h at RT | conc. HCl (55 mL) | 96.2:3.8 | 3.8% | n.d. tacky solid |
| 17 | 11 mmol 96.5% ee | 4.0 (a) 10 min | THF (85 mL) | 0° C. to RT 1.5 h at RT | conc. HCl (50 mL) | 96.3:3.7 | 4.7% | (>100%) |
| 18 | 52 mmol 96.5% ee | 3.0 (a) 10 min | THF (400 mL) | 0° C. to RT 1.5 h at RT | conc. HCl (200 mL), slurry in (i-Pr.)O | 96.8:3.2 | 3.5% | (93.4); 78.7% (b) (3.1% dia-(XIX) containing to 1.8% of by-products) |

Comments:
(a) The amount of borane-dimethyl sulfide complex used was determined from the volume of the reagent used.
(b) Isolated product of formula (XIX) after slurrying in diisopropyl ether.

Quantitative conversions of the Mannich base to components of the salt (XVIII) were achieved down to 3.0 equivalents of reducing agent (Table 9, No. 8–11, 16 and 18). While hardly any conversion to (XIX) was achieved in toluene (Table 9, No. 1), there was substantial to complete conversion in THF (Tab. 9, No. 2–18). In the case of the carbonyl reduction, diastereoselectivities (ratio of (XIX)/dia-(XIX)) of up to 96.8:3.2 were achieved (Table 9, No. 4 and 18). The isolated yields of (XIX) were 78–83% of theory, and these products also contained 3–4% of the diastereomer dia-(XIX) and almost 2% of the enantiomer of (XIX) (Table 9, No. 9 and 18), since there was in this case no crystallization step of the dihydrochloride of (XIX) similar to process step 3, section a). Including the crystallization of the dihydrochloride, the enantiomerically and diastereomerically pure amino alcohol (XIX) (>99% ee, >99% de, >99% chemical purity) was obtained in a yield of 70–75% of theory, based on the mandelate (XVIII) used.

In Table 10, the results of diastereoselective carbonyl reductions of (+)-dipivaloyl-tartaric acid salt (XII) (compound of formula (III) wherein $R^1$ is o-nitrophenyl, $R^2$ is 2-pyridyl, $R^3$ is H, $R^4$ is 2-pyridyl, $R^5$ is Ph and HY* is (+)-dipivaloyltartaric acid) to the 1,3-amino alcohol (XIX) are summarized by way of example:

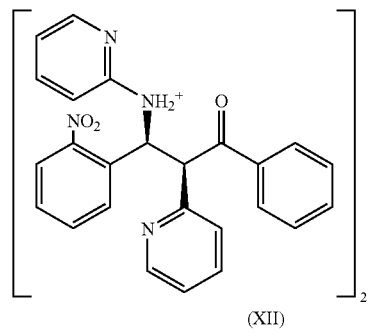

(XII)

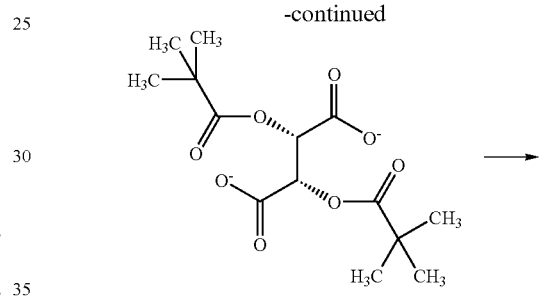

-continued

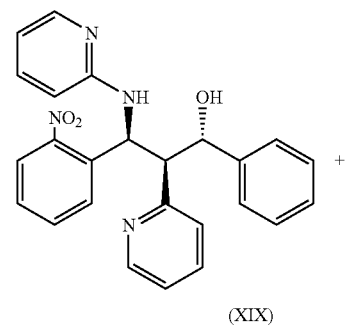

(XIX)

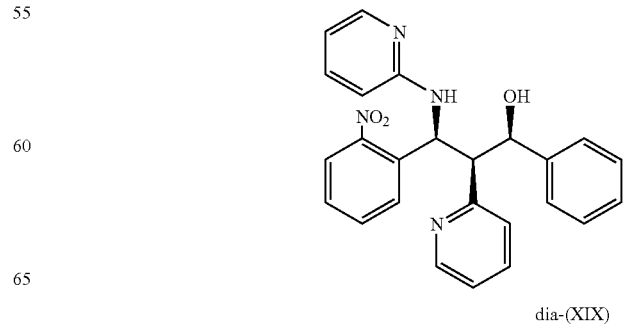

dia-(XIX)

TABLE 10

| No. | Reactant (XII); mmol of free Mannich base contained therein; optical purity | Reducing agent; reagents; (molar equiv., based on free Mannich base) | Solvent | Temperature, Time | Workup | Ratio of (XIX)/dia-(XIX) (HPLC); (reaction mixture) isolated product | HPLC or HPLC/MS of (reaction mixture) isolated product | Weight (content according to HPLC assay based on standard) | Yield % of theory assay-corrected |
|---|---|---|---|---|---|---|---|---|---|
| 1 | 15.0 g of (XII) 21.58 mmol of free Mannich base 74.0% ee | NaBH$_4$ (4.0 equiv.) | 200 mL Butanol/ water 82:18 (v/v) | 30–35° C. 20 h | 50 mL acetone; batch discarded | | [<5% of (XIX); mainly by-product of mass 350] | | |
| 2 | 5.0 g of (XII) 7.92 mmol of free Mannich base 74.0% ee | NaBH$_4$ (3.0 equiv.) BzEt$_3$N$^+$Cl$^-$ (0.1 equiv.) | 25 mL Ethanol | Room temp. 3 h | 4.5 mL acetone | (65/35) 58/42 | 53% of (XIX), 38% of dia-(XIX), 5% of by-product of mass 436 and 3% of mass 426 | 1.48 g | (44.0%) |
| 3 | 10.0 g of (XII) 16.08 mmol of free Mannich base 95.1% ee | BH$_3$—Me$_2$S (5 equiv.) | 100 mL THF | Addition: 3° C./15 min Reaction: 0° C. up to RT/ 30 min | 20% aqueous KOH, then 60° C./20 h | 97.6/2.4 | 93.0% (XIX) (95.2% ee), 1.5% dia-(XIX), 5.5% Oxazaborinane (C) | 7.05 g (77.2%) | 79.3% |
| 4 | 5.0 g of (XII) 8.0 mmol of free Mannich base 95.1% ee | BH$_3$—Me$_2$S (5 equiv.) | 50 mL MtBE | Addition: 0–5° C.; 5 min Reaction: RT; 2.5 h | No reaction batch discarded | | | | |
| 5 | 10.0 g of (XII) 16.08 mmol of free Mannich base 95.1% ee | BH$_3$—Me$_2$S (5 equiv.) | 100 mL THF | Addition: 0–5° C.; 15 min Reaction: 0° C. up to RT/ 20 min | 45 mL of H$_2$O and 10 mL of HCl (37%), then 60° C./15 min; to pH 13 using 30 mL of NaOH (33%), CH$_2$Cl$_2$-extraction, concentration | 97.8/2.2 | 94.8% (XIX) (96.8% ee) | 8.11 g (75.1%) | 88.8% |
| 6 | 15.0 g of (XII) 24.12 mmol of free Mannich base 95.1% ee | BH$_3$—Me$_2$S (5 equiv.) | 150 mL THF | Addition: 0–5° C.; 15 min Reaction: 0° C. up to RT/ 20 min | 50 mL of H$_2$O and 15 mL of HCl (37%), then 60° C./15 min; to pH 13–14 using 35 mL of NaOH (33%), CH$_2$Cl$_2$ extraction, concentration | 97.5/2.5 | 96.2% (XIX) (96.6% ee) | 10.43 g (82.9%) | 84.0% |
| 7 | 15.0 g of (XII) 25.29 mmol of free Mannich base 92.5% ee | BH$_3$—Me$_2$S (4 equiv.) | 150 mL THF | Addition: 0–5° C.; 15 min Reaction: 0° C. up to RT/ 20 min | 50 mL of H$_2$O and 15 mL of HCl (37%), then 60° C./30 min; 15 g of oxone added at RT and 30 min at RT; to pH 13–14 using 35 mL of NaOH (33%), CH$_2$Cl$_2$ extr., concentration | >97.2/<2.8 | 92.1% (XIX) (93.1% ee) | 12.18 g (77.4%) | 87.3% |
| 8 | 4.4 g of (XII) 7.43 mmol of free Mannich base 92.5% ee | BH$_3$13 Me$_2$S (3.18 equiv.) | 44 mL THF | Addition: 0–5° C.; 5 min Reaction: 0° C. up to RT/ 1.5 h | 15 mL of H$_2$O and 4 mL of HCl (37%), then 40° C./ 3 h; to pH 11 using 5 mL of NaOH (30%), | 97.8/2.2 | 92.8% (XIX) (91.8% ee), 2.1% dia-(XIX), 1.6% Oxazaborinane (C), 3.5% by- | 2.9 g | (89.8%) |

TABLE 10-continued

| No. | Reactant (XII); mmol of free Mannich base contained therein; optical purity | Reducing agent; reagents; (molar equiv., based on free Mannich base) | Solvent | Temperature, Time | Workup | Ratio of (XIX)/dia-(XIX) (HPLC); (reaction mixture) isolated product | HPLC or HPLC/MS of (reaction mixture) isolated product | Weight (content according to HPLC assay based on standard) | Yield % of theory assay-corrected |
|---|---|---|---|---|---|---|---|---|---|
| 9 | 15.3 g of (XII) 25.3 mmol of free Mannich base 93.2% ee | BH$_3$—Me$_2$S (2.5 equiv.) | 125 mL THF | Addition: 0–5° C.; 5 min Reaction: 0° C. up to 25° C./2 h | CH$_2$Cl$_2$ extr., concentration; crystallized at 0° C. using 50 mL iPr$_2$O; dried under high vacuum 20.9 g of MeOH at 5° C. followed by 4.92 g of MeSO$_3$H, 35° C./ 6 h; THF/MeOH distilled off under reduced pressure; plus 75 mL of H$_2$O and 10 mL 25% NH$_4$OH, 1 h at 25° C.; solid filtered off with suction; digested in 66 mL of iPr$_2$O, filtered off with suction, dried under high vacuum | (98.1/1.9) 99.2/0.8 | products 99.2% (XIX) (95.2% ee), 0.8% dia-(XIX) | 9.46 g (97.9%) | 86.2% |

The use of sodium borohydride in butanol/water resulted in only a little of the desired product (XIX) (Table 10, No. 1). Although the conversion was better using sodium borohydride in ethanol in the presence of catalytic amounts of a quaternary ammonium salt, the diastereoselectivity was only very low (Table 10, No. 2). When the borane-dimethyl sulfide complex was used as the reducing agent, excellent conversions and diastereoselectivities were achieved in THF (Tab. 9, No. 5–9), while there was no reaction in methyl tert-butyl ether (Tab. 9, No. 4). The ratio of (XIX) to dia-(XIX) (diastereoselectivity of the carbonyl reduction) in the crude reaction mixture after solvolysis of the intermediate (C) was up to 98:2 (Table 10, No. 9). In the isolated products (XIX) (yield 84–89% of theory, based on the salt (XII) used), the diastereomeric ratio was up to 99.2:0.8 and the enantiomeric purity 95.2% ee, although the charge of Mannich salt (XII) used had an optical purity of only 93.2% ee that was moderate for the four-component coupling, and although the workup procedure included no crystallization step of the dihydrochloride of (XIX) from butanol (Table 10, No. 9). With regard to the chemical purity, no UV-active impurities apart from dia-(XIX) could be detected by HPLC, and the (XIX) content of the isolated product according to an HPLC assay (based on a purified reference standard of (XIX)) was 97.9%.

The present invention allows compounds of formulae (I), (II) and (III) to be prepared in high yields with high stereoselectivity starting from achiral, commercially obtainable reactants (IV), (V) and (VI) that are inexpensive or very easy to prepare by a short route using inexpensive, readily available auxiliaries (VII) and mild reaction conditions that are easy to realize from a technical point of view. The process described in the present invention is therefore particularly suitable for the industrial production of optically active compounds of formulae (I) and (II).

The following scheme provides an overview of the process according to the invention:

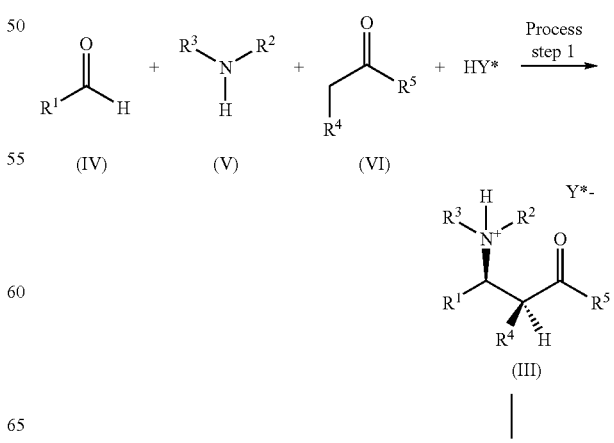

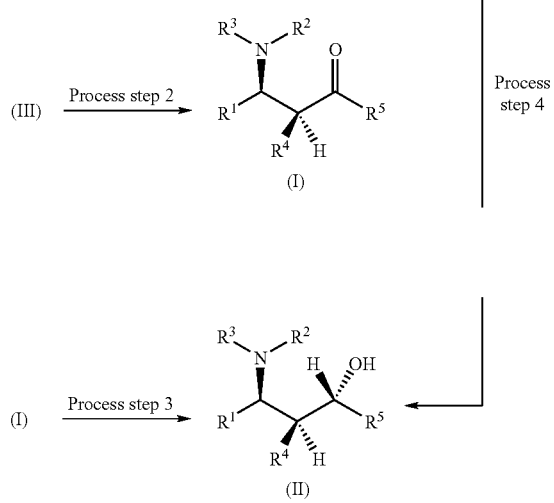

The abovementioned tables and exemplary reactions contain a total of 162 examples that illustrate the wide variety of possible variations of reaction parameters within the process according to the invention. Of these 162 examples recorded in the tables, the particularly representative procedures have been described in detail. These procedures are preferred embodiments of the process according to the invention. However, they do not in any way limit the subject matter of the invention.

The invention also encompasses all combinations of particular and preferred aspects of the invention noted herein.

EXAMPLES

The following examples are described to illustrate the methods of reproducing or verifying the subject matter of the invention without problems and are intended to illustrate the process steps according to the invention without limiting the subject matter of the invention.

Example 1

Determination of the enantiomeric excess of Mannich bases of the general formula (I) or of Mannich salts of the general formula (III) wherein $R^1$ is o-nitrophenyl, $R^2$ is 2-pyridyl, $R^3$ is H, $R^4$ is 2-pyridyl, $R^5$ is phenyl and HY* is (S)-(+)-mandelic acid, by derivatizing with (−)-camphanoyl chloride.

10 mg of the Mannich base (I) specified in the title or its salt (III) are weighed into a 10 mL volumetric flask and admixed with 200 mg of (−)-camphanoyl chloride. 1 mL of triethylamine is added and the mixture is made up to exactly 10 mL using approx. 9 mL of acetonitrile (HPLC grade). The mixture is dissolved within 30 seconds in an ultrasound bath. 1 mL of the initially light yellow solution is transferred to an HPLC vial and, after a 10 min delay time, 8.0 µL thereof are injected to a Machery-Nagel CC 250 mm×4 mm Nucleosil 100-5 C18/5 µm HD HPLC column. The elution is effected at a flow rate of 1.00 mL/min with a linear gradient composed of the two following eluents:

Eluent 1: Water/acetonitrile/trifluoroacetic acid is 900/100/1.00

Eluent 2: Water/acetonitrile/trifluoroacetic acid is 100/900/0.75 at the following gradient variation:

|  | Time (in min) | | | | |
| --- | --- | --- | --- | --- | --- |
|  | 0 | 2 | 22 | 26 | 27 |
| Eluent 1 (in % by volume) | 75 | 75 | 35 | 35 | 75 |
| Eluent 2 (in % by volume) | 25 | 25 | 65 | 65 | 25 |

The detection is effected at 254 nm. The derivatization products are eluted at the following retention times:

Corresponding amide of the general formula (IX A) (resulting from the undesired enantiomer of (I)): 19.59 min.
Amide of formula (IX) (resulting from the desired enantiomer of (I)): 20.50 min.
Amide resulting from the anti-diastereomer of (I): 23.12 min.
Amide resulting from the anti-diastereomer of (I)-enantiomer: 24.09 min.
A peak at retention time 20.01 min. is also visible which results from a derivatization component.

The enantiomeric excess (I) is determined with the aid of the chromatogram as follows: the sum of peak areas of (IX) and (IX A) is set to 100%. The proportions of (IX) and (IX A) are calculated (for example (IX) is 97.0%, (IX A) is 3.0%). The proportion of (IX A) is deducted from the proportion of (IX).

In the example specified, the free Mannich base (I), or the underlying Mannich base (I) of the Mannich salt (III) had an enantiomeric purity of 94.0% ee.

Example 2

Determination of the enantiomeric excess of Mannich bases of the general formula (I) or of Mannich salts of the general formula (III) wherein $R^1$ is o-nitrophenyl, $R^2$ is 2-pyridyl, $R^3$ is H, $R^4$ is 2-pyridyl, $R^5$ is phenyl and HY* is (S)-(+)-mandelic acid, by derivatizing with pivaloyl chloride.

In a 2 mL HPLC vial, 1 mg of the Mannich base (I) specified in the title or its salt (III) is dissolved in 20 µL of pivaloyl chloride, 100 µL of triethylamine and 500 µL of acetonitrile (HPLC grade). After exactly 5 minutes, the reaction is stopped by adding 500 µL of water. The vial is immediately sealed with the septum cap, placed in the autosampler of the HPLC instrument and, after a 10 min delay time, 5 µL thereof are injected onto a Merck Darmstadt 250 mm×4 mm 5 µm CHIRADEX column (β-Cyclodextrin) (Order No. 1.51333.0001, Cartridge No. 971324). The elution is effected isocratically at a flow rate of 1.00 mL/min using the following eluent mixture:
Eluent 1: 1% of triethylamine in acetic acid (pH 4.1)
Eluent 2: 100% of acetonitrile
Eluent 1: Eluent 2 is 82.5:17.5.
Detection is effected at 254 nm.

Example 3

Preparation of the free racemic Mannich base rac.-(I) [$R^1$ is o-nitrophenyl, $R^2$ is 2-pyridyl, $R^3$ is H, $R^4$ is 2-pyridyl and $R^5$ is phenyl] by catalysis of the three-component coupling with 1 mol % of p-toluenesulfonic acid 70 mL of abs. ethanol, 5.91 g (30 mmol) of 1-phenyl-2-(pyridin-2-yl)ethanone, 3.53 g (37.5 mmol) of 2-aminopyridine, 5.44 g (36.0 mmol) of 2-nitrobenzaldehyde and 57 mg (0.30 mmol) of 4-toluenesulfonic acid monohydrate are introduced in succession under nitrogen into a 250 mL four-neck flask equipped with a precision glass stirrer. The solution is stirred at 25° C. under nitrogen. After approx. 18 hours, the crystallization of the product rac.-(I) commences. At this juncture, TLC (n-Heptane/EtOAc) shows a conversion of approx. 40%. After a total of 96 hours, a thin layer chromatogram (TLC) shows virtually quantitative conversion. The precipitate is filtered off with suction, washed with mother liquor and then with 10 mL of ethanol, and dried at 30° C. under reduced pressure. 11.9 g (28.0 mmol; 93.2% of theory) of yellow crystals are obtained.

The integral of the $^1$H NMR spectrum (CDCl$_3$, measured immediately after dissolution) shows a ratio of the desired compound to the anti-diastereomer of 97:3.

Example 4

Reaction of Rac.-(I) with pivaloyl chloride in acetone to give the amide rac.-(IX) [R$^1$ is o-nitrophenyl, R$^2$ is 2-pyridyl, R$^3$ is H, R$^4$ is 2-pyridyl, R$^5$ is phenyl and R is tert-Bu]

In a 500 mL four-neck flask, 15.02 g (35.4 mmol) of the racemic Mannich base rac.-(I) from Example 3 are initially charged at 0° C. under nitrogen. 90 mL of acetone are then fed in with cooling to 0° C. internal temperature, and then 6.44 g (53.3 mmol) of pivaloyl chloride and 13.82 g (106.9 mmol) of diisopropylethylamine are metered in parallel from two dropping funnels. After stirring at 0° C. for three hours, HPLC analysis shows 95.9% of the desired rac.-(IX), 1.1% of the corresponding trans-diastereomer and 1.9% of unconverted rac.-(I). 40 mL of acetone are distilled off under reduced pressure (bath temperature <35° C.). 200 mL of water are fed in to the residue and then stirred at 0° C. internal temperature for a further 2 hours. The precipitate is filtered off with suction, washed on the filter with 20 mL of ice-cold ethyl acetate and then dried at 40° C. under reduced pressure. 16.4 g (32.2 mmol, 91% of theory) of a light yellow crystalline solid is obtained, m.p. 162° C. The HPLC purity is 99.4%.

Example 5

Classical optical resolution of rac.-(I) [R$^1$ is o-nitrophenyl, R$^2$ is 2-pyridyl, R$^3$ is H, R$^4$ is 2-pyridyl and R$^5$ is phenyl] using (S)-(+)-mandelic acid in acetone 6 mL of acetone were added to 503.9 mg (1.19 mmol) of rac.-(I) from Example 3 and 359.0 mg (2.36 mmol, 1.98 equiv.) of (S)-(+)-mandelic acid. The reaction mixture was magnetically stirred in a tightly sealed flask at 25° C. for 20 hours, and the precipitate was filtered off with suction and dried under reduced pressure. 446 mg (0.773 mmol) of the corresponding mandelate salt (III) were obtained that, according to $^1$H NMR, consisted of Mannich base (I) and mandelic acid in a ratio of 1:1.00. Derivatization of a sample with (−)-camphanoyl chloride and subsequent HPLC analysis according to Example 1 delivered a ratio of the amide (IX A) to the amide (IX) of 5.0 to 95.0. The enantiomeric excess of the Mannich base (I) in the mandelate salt (III) was therefore 90% ee.

Example 6

Classical optical resolution of rac.-(I) [R$^1$ is o-nitrophenyl, R$^2$ is 2-pyridyl, R$^3$ is H, R$^4$ is 2-pyridyl and R$^5$ is phenyl] using L-(−)-malic acid in acetone 6 mL of acetone were added to 504.2 mg (1.19 mmol) of rac.-(I) from Example 3 and 161.5 mg (1.20 mmol, 1.01 equiv.) of L-(−)-malic acid. The reaction mixture was magnetically stirred in a tightly sealed flask at 25° C. for 20 hours, and the precipitate was filtered off with suction and dried under reduced pressure. 400 mg (0.716 mmol) of the corresponding malate salt (III) were obtained that, according to $^1$H NMR, consisted of Mannich base (I) and malic acid in a ratio of 1:1.04. Derivatization of a sample with (−)-camphanoyl chloride and subsequent HPLC analysis according to Example 1 delivered a ratio of the amide (IX A) to the amide (IX) of 2.4 to 97.6. The enantiomeric excess of the Mannich base (I) in the malate salt (III) was therefore 95.2% ee.

Example 7

Classical optical resolution of rac.-(I) [R$^1$ is o-nitrophenyl, R$^2$ is 2-pyridyl, R$^3$ is H, R$^4$ is 2-pyridyl and R$^5$ is phenyl] using (−)-di,O,O'-pivaloyl-D-tartaric acid [(−)-DPTA] in acetone 6 mL of acetone were added to 506.2 mg (1.19 mmol) of rac.-(I) from Example 3 and 379.2 mg (1.19 mmol, 1.00 equiv.) of (−)-DPTA. The reaction mixture was magnetically stirred in a tightly sealed flask at 25° C. for 20 hours, and the precipitate was filtered off with suction and dried under reduced pressure. 557 mg of the corresponding DPTA salt (III) were obtained that, according to $^1$H NMR, consisted of Mannich base (I) and DPTA in a ratio of 1:0.57. Derivatization of a sample with (−)-camphanoyl chloride and subsequent HPLC analysis according to Example 1 delivered a ratio of the amide (IX A) to the amide (IX) of 97.6 to 2.4. The enantiomeric excess of the corresponding Mannich base (I) in the DPTA salt (III) was therefore 95.2% ee.

Example 8

Attempted classical optical resolution of rac.-(I) [R$^1$ is o-nitrophenyl, R$^2$ is 2-pyridyl, R$^3$ is H, R$^4$ is 2-pyridyl and R$^5$ is phenyl] using (S)-(+)-mandelic acid in ethanol 6 mL of ethanol were added to 500 mg (1.18 mmol) of rac.-(I) from Example 3 and 358.5 mg (2.36 mmol, 2.00 equiv.) of (S)-(+)-mandelic acid. The reaction mixture was magnetically stirred in a tightly sealed flask at 20–25° C. for 18 hours, and the precipitate was filtered off with suction, washed with a little ethanol and dried under reduced pressure. 590 mg (1.02 mmol) of the corresponding mandelate salt (III) were obtained. HPLC analysis according to Example 1 delivered a ratio of the amide (IX A) to the amide (IX) of 47.9 to 52.1. The enantiomeric excess of the Mannich base (I) in the mandelate salt (III) was therefore only 4% ee.

Example 9

Synthesis of the imine (X) from the aldehyde (IV) and the amine (V) [R$^1$ is o-nitrophenyl and R$^2$ is 2-pyridyl]

50 mL of toluene are added to 9.97 g (106 mmol) of 2-aminopyridine, 15.12 g (100 mmol) of 2-nitrobenzaldehyde and 190.3 mg (1 mmol) of 4-toluenesulfonic acid monohydrate, and the reaction mixture is heated to reflux for 1 h under nitrogen while azeotropically distilling off the toluene/water azeotrope on a water separator. The mixture is then cooled to room temperature and the corresponding imine (X) where R$^1$ is o-nitrophenyl and R$^2$ is 2-pyridyl crystallizes out. The product is filtered off with suction and dried under reduced pressure. 18.2 g (80 mmol, 80% of theory) of yellow crystals are obtained. According to $^1$H NMR (300 MHz, CDCl$_3$; measured immediately after dissolution), 80% of the product is the imine (X) [δ is 7.24 (m, 1H), 7.38 (d, 1H), 7.63 (td, 1H), 7.70–7.83 (m, 2H), 8.06 (dd, 1H), 8.36 (dd, 1H), 8.53 (dm, 1H), 10.28 (s, 1H)] and 10% each are the reactants 2-aminopyridine and 2-nitrobenzaldehyde. IR (KBr): ν is 1513 (s), 1435 (m), 1352 (m), 1339 (s), 788 (m) cm$^{-1}$. MS (DCI): C$_{12}$H$_9$N$_3$O$_2$ (M is 227), m/z is 228 (100%, M+H$^+$).

Example 10

Synthesis of the aminal (XI) from the aldehyde (IV) and the amine (V) [R$^1$ is o-nitrophenyl and R$^2$ is 2-pyridyl]

9.97 g (106 mmol) of 2-aminopyridine and 15.12 g (100 mmol) of 2-nitrobenzaldehyde are dissolved under nitrogen in 53 mL of dichloromethane in a 250 mL four-neck round-bottom flask equipped with a precision glass stirrer, thermometer, water separator and reflux condenser, and the internal temperature falls to 12° C. 1.5 g of strongly acidic ion exchanger (Amberlite IR 120, Merck) are introduced and the reaction mixture is then heated to reflux at a bath temperature of 75° C. In the water separator, approx. 1.5 mL of water collect (theory: 1.8 mL from the reaction plus 0.8 mL from the ion exchanger). After 5.5 hours, no more water separation can be discerned. When the stirrer is switched off, a clear solution that is hardly any darker than the original reactant solution can be seen above the settled ion exchange resin.

After standing at room temperature overnight, a considerable amount of yellow crystals have precipitated. The suspension is heated to reflux and sufficient dichloromethane is added (approx. 100 mL) to just completely dissolve the crystals in the heat of boiling. The batch is hot-filtered through a fluted filter in order to remove the ion exchanger. The filtrate is admixed with 250 mL of toluene and the dichloromethane is evaporated off under reduced pressure (beginning: 400 mbar, end: 100 mbar) at a bath temperature of 40° C. Toward the end of the concentration, a pale yellow solid precipitates out. Improvement of the vacuum to 15 mbar then removes ⅔ of the toluene. The suspension is stored tightly sealed in a refrigerator at approx. 0° C. overnight, which completes the crystallization of the product. The solid is filtered off with suction, washed with 20 mL of cold toluene and dried under reduced pressure at 40° C. 14.50 g (45.1 mmol, 45.1% of theory) of pale yellow solid are obtained, melting point 134–135° C., after a further recrystallization from toluene, melting point 140–142° C.

$^1$H NMR (300 MHz, DMSO-d$_6$): δ is 6.53 (tm, 2H), 6.58 (d, 2H), 7.20 (d, 2H), 7.30–7.44 (m, 3H), 7.53 (td, 1H), 7.67 (td, 1H), 7.78 (dt, 1H), 7.88 (d, 1H), 7.94 (m, 2H). IR (KBr): ν is 3227 (m), 3074 (m) and 3020 (m), 1599 (s), 1576 (m), 1532 (s), 1459 (m), 1435 (s), 1320 (m), 1149 (m), 771 (m) cm$^{-1}$. MS (DCI): C$_{17}$H$_{15}$N$_5$O$_2$ (M is 321), m/z is 228.1 (100%, M+H$^+$-aminopyridine), 94.8 (aminopyridine).

Example 11

Recovery of (S)-(+)-mandelic acid from the aqueous mother liquor of the liberation of Mannich base (I) from a Mannich salt of formula (III) [R$^1$ is o-nitrophenyl, R$^2$ is 2-pyridyl, R$^3$ is H, R$^4$ is 2-pyridyl, R$^5$ is phenyl and HY* is (S)-(+)-mandelic acid]

The Mannich base (I) having the substituents specified in the title was liberated from 256.5 g (445.0 mmol) of the corresponding Mannich salt (III) in 1280 mL of water and 128 mL of ethanol using 222.0 mL of 2 N sodium hydroxide solution (444.0 mmol) at pH-stat 8.5, filtered off with suction, washed with 3×150 mL of water and dried under reduced pressure to obtain 188.52 g of (I) (444.1 mmol, 99.8% of theory). The yellow aqueous mother liquor (pH 7.62) that had previously stood at room temperature for 5 days was washed initially with 2×250 mL of methyl tert-butyl ether, then with 250 mL of ethyl acetate. The washing phases mentioned were all distinctly yellow, and after concentrating to dryness under reduced pressure, contained 0.21 g, 0.06 g and 0.04 g of residue, and were all discarded. The aqueous mother liquor (pH 7.83) that was now only very pale yellow was adjusted to the pKa value of mandelic acid (pH 3.85) (calibrated glass electrode) using 12 mL of 37% hydrochloric acid. The solution became cloudy, but no mandelic acid precipitated out. Extraction was effected using 500 mL of ethyl acetate. After concentrating to dryness under reduced pressure, this "extract 1" comprised 14.10 g (92.67 mmol, 20.8% of theory) of residue. A further 19 mL of 37% hydrochloric acid were then added dropwise to the aqueous phase with stirring that resulted in the pH falling from 4.2 to 2.44 and cloudiness occurring again. Extraction was effected using 500 mL of ethyl acetate. After concentrating to dryness under reduced pressure, this "extract 2" comprised 29.57 g (194.35 mmol, 43.7% of theory) of residue. 18.5 mL of 37% hydrochloric acid were added dropwise to the aqueous phase with stirring, which resulted in the pH falling from 2.99 to 1.08. Extraction was effected using 500 mL of ethyl acetate. After concentrating to dryness under reduced pressure, this "extract 3" comprised 12.62 g (82.94 mmol, 18.6% of theory) of residue. The aqueous phase (pH 1.4) was extracted once more with 500 mL of ethyl acetate. After concentrating to dryness under reduced pressure, this "extract 4" comprised 3.71 g (24.38 mmol, 5.5% of theory) of residue. The melting points (DSC measurements) of all four residues (extracts 1 to 4) were from 133.2° C. to 133.5° C. According to $^1$H NMR spectra (400 MHz, DMSO-d$_6$), all four residues consisted of mandelic acid of high purity. A sample of each residue was derivatized to the methyl ester with a solution of diazomethane in diethyl ether, and analyzed by GC to find the enantiomeric excess using a capillary column with a chiral phase [50 m×0.25 mm ID fused silica capillary column coated with 0.25 µm of Lipodex-E (Ser. No. 723369, column No. 20174-32). Oven temperature: 115° C. isothermal, injector: 200° C., detector: 220° C., flow rate: 2.0 mL of He/min. Split: 1:100. The retention time of the (S)-(+)-mandelic acid (as the methyl ester) was 24.73 min. A racemic comparative sample was used to determine that the retention time of (R)-(−)-mandelic acid (as the methyl ester) was 25.90 min]. In none of the residues (extracts 1 to 4) could (R)-(−)-mandelic acid be detected. A total of 60.0 g (394.35 mmol, 88.6% of theory) of (S)-(+)-mandelic acid were therefore recovered at 100% ee.

For a recovery of (S)-(+)-mandelic acid on the industrial scale, there is thus the possibility of continuously extracting the aqueous mother liquor, for example in a countercurrent process with, for example, ethyl acetate, by maintaining the pH within the range from 2.5–1.0 by continuously adding 37% hydrochloric acid.

Example 12

Synthesis and isolation of the mixture of oxaborinanes having the main component of formula (C) [R$^1$ is o-nitrophenyl, R$^2$ is 2-pyridyl, R$^3$ is H, R$^4$ is 2-pyridyl and R$^5$ is phenyl]

In a 250 mL four-neck flask equipped with precision glass stirrer, internal thermometer and septum, the suspension of 6.37 g (15 mmol) of a Mannich base (I) [$R^1$ is o-nitrophenyl, $R^2$ is 2-pyridyl, $R^3$ is H, $R^4$ is 2-pyridyl and $R^5$ is phenyl] in 75 mL of toluene was cooled to an internal temperature of +1° C. using an ice bath. Within 2 minutes, 4.47 mL (45 mmol, 3.0 equiv.) of borane-dimethyl sulfide (95% in dimethyl sulfide) were added via a syringe which resulted in a maximum internal temperature increase of +3° C. The cooling bath was removed and the suspension heated to +18° C. within 15 minutes. The light yellow suspension was stirred vigorously at this temperature for 45 minutes.

HPLC analysis of the suspension [injection of 8.0 μL of a solution in acetonitrile onto a 250×4 mm steel column Nucleosil 100-5 C18, 5 μm, flow rate 1.0 mL/min., det. 254 nm, eluent A: water (900 mL)/acetonitrile (100 mL)/trifluoroacetic acid (1.00 mL), eluent B: water (100 mL)/acetonitrile (900 mL)/trifluoroacetic acid (0.75 mL); elution with a linear gradient: 0–2 min (75% A, 25% B), 22–26 min (35% A, 65% B), 27 min (75% A, 25% B)] showed that all but 2% of the Mannich base (I) had reacted ((I) and the retro-Mannich products forming on the column give a broad peak having shoulders at $t_{ret}$ 3–4 min). In addition to the toluene peak ($t_{ret}$ 20.8 min), several minor peaks and 3% of the 1,3-amino alcohol (II) ($t_{ret}$ 12.4 min), two peaks of relatively long retention time were detected ("peak 1" $t_{ret}$ 25.5 min, "peak 2" $t_{ret}$ 28.6 min) whose total peak area amounted to 93% of all peaks (apart from toluene). Between these two peaks, the base line was not reached again (remains on a plateau) that implies a conversion of the compound "peak 1" to the compound "peak 2" on the column.

The suspension was cooled to +5° C. and rapidly admixed with 5 mL of water, then stirred at room temperature for 5 min. The suspension was filtered via a Büchner funnel. The very pale yellow solid was washed with toluene (2×10 mL) and dried at +45° C./150 mbar under nitrogen. 6.22 g (14.26 mmol based on formula (C), 95% of theory) of colorless powder were obtained.

In DSC, this powder showed a weak endothermic peak at 104.6° C. (−9.5 J/g) and a very strongly exothermic (1718 J/g) decomposition peak at 166.8° C. (onset at 157° C.).

For "peak 1", HPLC-MS (API positive) gave M+H$^+$: m/z is 437.3 that corresponds to the empirical formula $C_{25}H_{21}BN_4O_3$ (molecular weight 436.28) of formula (C). For "peak 2", the following mass peaks were detected: m/z is 488.3, 449.2 and 439.3. This is possibly the boric acid adduct of the 1,3-amino alcohol (II) [$C_{25}H_{22}N_4O_3 \times H_3BO_3$, molecular weight 488.3]. Boric acid and amino alcohol (II) are the expected hydrolysis products of the oxazaborinane (C) in aqueous acidic medium.

Finally, a sample of the colorless powder (C) is solvolyzed using 3.0 equiv. of methanesulfonic acid in an excess of methanol at +20° C. HPLC analysis of the reaction mixture showed the virtually complete disappearance (<1%) of "peak 1" and "peak 2" with simultaneous continuous growth of the peak of the amino alcohol (II) (94%) and its diastereomer dia-(II) ($t_{ret}$ 8.2 min, 4%). A similar workup to Example 19 delivered the dihydrochloride of the pure amino alcohol (II) (100% ee, 99.5% de) in a yield of 75% of theory.

Example 13

Synthesis of the optically active Mannich salt of formula (III) [$R^1$ is o-nitrophenyl, $R^2$ is 2-pyridyl, $R^3$ is H, $R^4$ is 2-pyridyl and $R^5$ is Phenyl] by four-component coupling with dynamic optical resolution at room temperature; monitoring of the variation of ee with time (Table 1); use of (+)-dipivaloyltartaric acid as the chiral auxiliary [HY* is (+)-DPTA] and ethanol as solvent (Table 2, No. 5):

60 mL of ethanol (denatured with toluene) were initially charged with stirring into a 100 mL three-neck round-bottom flask equipped with a precision glass stirrer, nitrogen feed and bubble counter, and 4.63 g (23.5 mmol, 1.00 equiv.) of 2-pyridylmethyl phenyl ketone, 2.77 g (29.4 mmol, 1.25 equiv.) of 2-aminopyridine, 4.26 g (28.2 mmol, 1.20 equiv.) of 2-nitrobenzaldehyde and 7.48 g (23.5 mmol, 1.00 equiv.) of (+)-dipivaloyltartaric acid were introduced in succession. After approx. 10 min, a clear, yellow solution was formed which began to become cloudy approx. 15 min. later. Seed crystals (10 mg) of enantiomerically pure (+)-DPTA salt were added that resulted in a yellow suspension that was stirred at room temperature under a nitrogen atmosphere for 14 days. At each of the times visible from Table 1, small aliquots of the reaction suspension were withdrawn, the solids contained therein were separated from the mother liquor by microfiltration and derivatized with (−)-camphanoyl chloride as described in Example 1, and analyzed by means of HPLC. The variation of ee with time observed is reported in Table 1. On the 14th day, the ratio of the desired enantiomer to the undesired enantiomer was 97.67:2.33, corresponding to 95.34% ee. The suspension which was now white was filtered, and the filter residue was washed with the mother liquor and then twice with 10 mL of ethanol each time. The solid was dried at 45° C. under high vacuum for 2 hours. 11.45 g (9.81 mmol, 83.6% of theory) of the white salt were obtained which, according to $^1$H NMR and titration contained two Mannich base cations per DPTA dianion. It can be estimated that the actual yield was distinctly above 90% of theory, since the 10 intermediate sample withdrawals consumed significant amounts of product.

Example 14

Synthesis of the optically active Mannich salt of formula (III) [$R^1$ is o-nitrophenyl, $R^2$ is 2-pyridyl, $R^3$ is H, $R^4$ is 2-pyridyl and $R^5$ is phenyl] by four-component coupling with dynamic optical resolution at +40° C. Use of (+)-dipivaloyltartaric acid as the chiral auxiliary [HY* is (+)-DPTA] and ethanol as solvent (Table 2, No. 6):

In a 250 mL four-neck round-bottom flask equipped with a precision glass stirrer, nitrogen feed, and reflux condenser with bubble counter, 5.06 g (25.65 mmol, 1.00 equiv.) of 2-pyridylmethyl phenyl ketone were dissolved in 60 mL of absolute ethanol. Within 10 min, 2.99 g (31.76 mmol, 1.24 equiv.) of 2-aminopyridine, 4.61 g (30.53 mmol, 1.19 equiv.) of 2-nitrobenzaldehyde and 8.08 g (25.38 mmol, 0.99 equiv.) of (+)-DPTA were added in succession at an internal temperature of 40° C., and each addition was effected after waiting for just the amount of time required for the solid to go completely into solution. A clear yellow solution was obtained that transformed into a yellow suspension after 25 min. The reaction mixture was then stirred at 40° C. overnight. Samples taken intermediately and derivatized showed that the enantiomeric excess of the solid was 55.7% ee after 4.16 hours and 93.0% ee after 20 hours. After 23 hours, the heating bath was removed and the suspension cooled to 23° C. within 15 minutes, and the precipitate was filtered off with suction, washed twice with 10 mL of ethanol and then dried at 45° C. under high vacuum. 14.89 g (12.76 mmol, 25.52 mmol of the Mannich base (I) containing the substituents specified in the title, 99.5% of theory) were obtained as a very pale yellow solid. According to $^1$H NMR and titration, the salt consisted of (I) and DPTA in a ratio of 2:1. The enantiomeric excess was 95.9% ee.

Example 15

Synthesis of the optically active Mannich salt of formula (III) [$R^1$ is o-nitrophenyl, $R^2$ is 2-pyridyl, $R^3$ is H, $R^4$ is 2-pyridyl and $R^5$ is phenyl] by four-component coupling with dynamic optical resolution at +60° C. Use of (S)-(+)-mandelic acid as the chiral auxiliary [HY* is (+)-MDLA] and ethanol as the solvent (Table 3, No. 7):

In a 2 liter jacketed reactor (connected to a circulation thermostat) equipped with a temperature sensor and mechanical turbine stirrer, 97.2 g (492.8 mmol, 1.00 equiv.) of 2-pyridylmethyl phenyl ketone were dissolved in 1200 mL of ethanol (denatured with methyl ethyl ketone) at room temperature. Over the course of 15 minutes, the internal temperature was increased to 40° C. At this temperature, 55.66 g (591.4 mmol, 1.20 equiv.) of 2-aminopyridine, 89.37 g (591.4 mmol, 1.20 equiv.) of 2-nitrobenzaldehyde and 149.96 g (985.6 mmol, 2.00 equiv.) of (S)-(+)-mandelic acid were added in succession. Immediately afterwards, the internal temperature of the reaction mixture was increased to 60° C. and a clear solution was obtained. This heating procedure lasted 30 minutes, and 15 minutes later, the first precipitate formation could be observed. Sample withdrawal/derivatization/HPLC analysis according to Example 1 allowed an enantiomeric excess of the precipitate of 91.5% ee after 2 h, 93.0% ee after 3.5 h and 94.4% ee after 4.5 h to be determined. The reaction mixture was cooled to 20° C. within 2 h. The precipitate was filtered off with suction, washed 3 times with 50 mL of ethanol, and then dried at 40° C. under a vacuum of 50 mbar to constant weight. 262.4 g (455.2 mmol, 92.4% of theory) of the mandelate salt (III) with the substituents specified in the title were obtained. The melting point was 153–154° C. According to $^1$H NMR, it contained the corresponding Mannich base (I) and mandelic acid in a ratio of 1:1. The enantiomeric purity was 94.4% ee by derivatization with camphanoyl chloride and 97.5% ee by the more exact method of pivaloyl derivatization according to Example 2.

Example 16

Synthesis of the optically active Mannich salt of formula (III) [$R^1$ is o-nitrophenyl, $R^2$ is 2-pyridyl, $R^3$ is H, $R^4$ is 2-pyridyl and $R^5$ is phenyl] by four-component coupling with dynamic optical resolution at +40° C. Use of (S)-(+)-mandelic acid as the chiral auxiliary [HY* is (+)-MDLA] and acetone as the solvent (Table 3, No. 20):

In a 2 liter jacketed reactor (connected to a circulation thermostat) equipped with a temperature sensor and mechanical turbine stirrer, 97.2 g (492.8 mmol, 1.00 equiv.) of 2-pyridylmethyl phenyl ketone were dissolved at room temperature in 1200 mL of acetone. Over the course of 15 minutes, the internal temperature was increased to 40° C. At this temperature, 55.66 g (591.4 mmol, 1.20 equiv.) of 2-aminopyridine, 89.37 g (591.4 mmol, 1.20 equiv.) of 2-nitrobenzaldehyde and 149.96 g (985.6 mmol, 2.00 equiv.) of (S)-(+)-mandelic acid were added in succession that resulted in a clear solution which was stirred further at 40° C. After 4.5 h, the first formation of precipitate could be detected. After 24 h, sample withdrawal/derivatization/HPLC analysis according to Example 1 gave a 97.0% ee of the precipitate. The suspension was cooled to an internal temperature of 25° C. within 2.5 h. The suspension was filtered off with suction, washed 3 times with 50 mL of acetone and dried at 40° C. under a vacuum of 50 mbar. 250.4 g (434.4 mmol, 88.2% of theory) of the mandelate salt (III) with the substituents specified in the title were obtained as an almost colorless solid having a melting point of 156–158° C. According to $^1$H NMR, it contained the corresponding Mannich base (I) and mandelic acid in a ratio of 1:1. The enantiomeric purity was 95.7% ee by derivatization with camphanoyl chloride (Example 1) and 97.0% ee by the more exact method of piv-derivatization (Example 2).

Example 17

Synthesis of the optically active Mannich salt of formula (III) [$R^1$ is o-nitrophenyl, $R^2$ is 2-pyridyl, $R^3$ is H, $R^4$ is 2-pyridyl and $R^5$ is phenyl] by coupling with Schiff base preformed in situ with dynamic optical resolution at 40°–60° C.; use of (S)-(+)-mandelic acid as the chiral auxiliary [HY* is (+)-MDLA] and n-butyl acetate as the solvent (Table 3, No. 23):

In a 1 liter four-neck round-bottom flask equipped with a water separator with fitted reflux condenser, precision glass stirrer, nitrogen feed and vacuum connection, the solution of 25.87 g (275 mmol) of 2-aminopyridine and 37.75 g (250 mmol) of 2-nitrobenzaldehyde in 500 mL of n-butyl acetate was heated to reflux at 100 mbar and a bath temperature of 70° C. (50–60° C. internal temperature) that resulted in approx. 4.7 mL of water separating in the water separator within 2.2 h.

The mixture was then left to stand overnight at 22° C. under a nitrogen atmosphere. 49.2 g (250 mmol) of 2-pyridylmethyl phenyl ketone were then added with stirring and, once it had all dissolved, 45.6 g (300 mmol) of (S)-(+)-mandelic acid were added and heated to an internal temperature of 40° C. Precipitate formation was observed after 5 min. After 3 h at 40° C., further heating was effected to 60° C. and stirring was continued at this temperature for 24 h. The suspension was cooled to 25° C. with stirring, and the precipitate was filtered off with suction, washed twice with 50 mL of n-butyl acetate and dried at 50° C. under reduced pressure. 134.6 g (233.4 mmol, 93.4% of theory) of the mandelate salt (III) with the substituents specified in the title were obtained. According to $^1$H NMR, it contained the corresponding Mannich base (I) and mandelic acid in a ratio of 1:1. The enantiomeric purity was 95.4% ee by derivatization with camphanoyl chloride (Example 1) and 98.0% ee by the more exact method of pivaloyl derivatization (Example 2).

Example 18

Typical procedure for Table 8: diastereoselective reduction of the optically active free Mannich base (I) [$R^1$ is o-nitrophenyl, $R^2$ is 2-pyridyl, $R^3$ is H, $R^4$ is 2-pyridyl and $R^5$ is phenyl, corresponding to a compound of formula (XVII)] to the enantiomerically pure 1,3-amino alcohol (XIX) and subsequent workup (Table 8, No. 29):

In a 500 mL four-neck flask equipped with a precision glass stirrer, dropping funnel and internal thermometer, 21.39 g (50.39 mmol, 1.0 equiv.) of the Mannich base (XVII) (chem. purity>99%, 95.6% ee, 0.36% of $H_2O$) were suspended in 160 mL of toluene under a nitrogen atmosphere and cooled using an ice bath to an internal temperature of +1° C. At this temperature, 10.18 g (125.97 mmol, 2.5 equiv.) of borane-dimethyl sulfide complex (94% in dimethyl sulfide) were added dropwise within 25 min, and the internal temperature rose to +2° C. Once addition had been completed, the mixture was heated to +20° C. within 30 min and stirred further at this temperature that resulted in the yellow suspension turning beige. Reaction monitoring after 15 min (HPLC as in Example 12) indicated the virtually complete consumption of (XVII) with the formation of an equilibrium of the corresponding oxazaborinanes of the general formula (C) and oligomers thereof. After a total stirring time of 1.5 h at 20° C., 70 mL of methanol were added dropwise within 10 min at an internal temperature of the reaction mixture of between +15° C. and +22° C. with ice bath cooling. During this addition, gas development was observed. 6.5 mL (100.78 mmol, 2.0 equiv.) of methanesulfonic acid were then added dropwise within 10 min at an internal temperature of +20° C. with ice cooling, and vigorous gas development and exothermicity was observed. Toward the end of the addition, a yellow solution was formed that was stirred at average to high speed at an internal temperature of +40 to +45° C. After a stirring time of 1.25 h, reaction monitoring by HPLC at 254 nm indicated a total of 6.1% of "retro-Mannich" decomposition products, complete disappearance of the intermediate oxazaborinanes and a diastereoselectivity of the reduction of 94.3:5.6. After a total of 1.75 h at 40–45° C., the mixture was concentrated on a rotary evaporator at a bath temperature of +40° C./350 to 150 mbar to remove 78 mL of distillate (methanol, trimethyl borate, some toluene). The resulting biphasic mixture (toluene and separated yellow oil) were admixed with 30 mL of 2N hydrochloric acid and extracted. The yellow, aqueous acidic phase was removed and the toluene phase re-extracted with 5 mL of 2N hydrochloric acid plus 10 mL of water. According to HPLC, the toluene phase then contained no more product (XIX) and was discarded. The combined aqueous acidic product-containing aqueous phases were dissolved in 200 mL of 1-butanol and admixed at an internal temperature of +20° C. within 10 min with 95 mL (190 mmol, 3.77 equiv.) of 2N sodium hydroxide solution in a 500 mL four-neck flask equipped with a precision glass stirrer and dropping funnel to obtain an orange-yellow emulsion that was stirred for a further 5 min. The product-containing, orange-yellow butanol phase (upper) was removed from the colorless, clear aqueous phase (lower, pH 10), and 85 mL of 1-butanol/water were distilled off azeotropically on a rotary evaporator at a bath temperature of +50° C. and from 250 to 45 mbar. The resulting concentrated solution of (XIX) in butanol was heated under nitrogen in a 500 mL four-neck flask equipped with a precision glass stirrer, dropping funnel and internal thermometer to an internal temperature of +45° C., and admixed within 5 min with 11.1 mL (110 mmol, 2.18 equiv.) of 30% hydrochloric acid via the dropping funnel that resulted in an internal temperature rise to +48° C. and a yellow solution. This solution was cooled to an internal temperature of +20° C. within 1 h, which resulted in the onset of the crystallization of the white dihydrochloride and the formation of a pasty suspension. The mixture was then further cooled to +5° C. within 10 min and stirred for a further 15 min at this temperature. The viscous suspension was then filtered via a Buchner funnel to obtain a white filter cake and a yellow filtrate. The filter cake was washed with 2×20 mL of 1-butanol, suction-dried and then dried in a vacuum drying cabinet at 40° C./100 mbar. 20.22 g (40.48 mmol calculated as (XIX)·2 HCl) of white crystalline solid were obtained. According to HPLC, it contained 99.8% of (XIX) and <0.1% of the diastereomer dia-(XIX). The enantiomeric purity was 100% ee. According to titration (acid/base and also chloride titration) and $^1$H NMR, (XIX) was present as the dihydrochloride. According to $^1$H NMR, 11.5% by weight (corresponding to 87.5 mol %) of 1-butanol were present. Even on extended drying at 40–50° C. under high vacuum, the butanol could not be removed. This behavior was observed in all dihydrochlorides of Table 8 which had been precipitated from 1-butanol. The butanol contents were without exception 85–97 mol %, so that the product may be regarded as the monobutanol solvate of (II)-dihydrochloride. The yield was 80.3% of theory when the product weight was calculated as (XIX)-dihydrochloride neglecting the butanol content and is based on the weight of the reactant (XVII) used without taking into account its incomplete enantiomeric purity (93.4% ee) [known as the telquel yield].

Example 19

Diastereoselective reduction of the optically active free Mannich base (I) [$R^1$ is o-nitrophenyl, $R^2$ is 2-pyridyl, $R^3$ is H, $R^4$ is 2-pyridyl and $R^5$ is phenyl, corresponding to a compound of formula (XVII)] to the enantiomerically pure 1,3-amino alcohol (XIX); use of borane-dimethyl sulfide complex as the reducing agent according to Table 8, No. 33; optimized workup.

In a 1 l four-neck round-bottom flask equipped with a precision glass stirrer, dropping funnel and internal thermometer, 63.63 g (150 mmol, 1.0 equiv.) of the Mannich base (XVII) (chem. purity>99%, 93.4% ee, 0.02% of $H_2O$) were suspended under a nitrogen atmosphere in 400 mL of toluene and cooled to an internal temperature of +1° C. using an ice bath. At this temperature, 31.60 g (391.1 mmol, 2.6 equiv.) of borane-dimethyl sulfide complex (94% in dimethyl sulfide) were added dropwise within 15 min that resulted in an internal temperature rise to +4° C. Once addition had been completed, the mixture was heated to +20° C. within 30 min and then stirred further at this temperature which resulted in the yellow suspension turning beige. Monitoring of the reaction after 2.5 h (HPLC system as in Example 12) indicated the virtually complete consumption of (XVII) with the formation of an equilibrium of oxazaborinanes. After a total stirring time of 4 h at 20° C., 190 mL of methanol were added dropwise within 10 min at an internal temperature of the reaction mixture between +15° C. and +22° C. with ice bath cooling. During this addition, gas development was observed. 31.1 mL (478.9 mmol, 3.19 equiv.) of methanesulfonic acid were then added dropwise within 20 min, likewise within an internal temperature interval of from +15° C. to +22° C., and vigorous gas development was observed. Once ⅔ of the total amount of acid had been introduced, a yellow solution was obtained. Once addition had been completed, the dropping funnel was rinsed using a further 53 mL of methanol and stirring was continued at from +20° C. to +22° C. After a stirring time of 1 h, HPLC reaction monitoring at 254 nm indicated a total of 5.4% of Mannich base (XVII) and "retro-Mannich" decomposition products, 5.3% of dia-(XIX) and 88.4% of (XIX), and also complete disappearance of the intermediate oxazaborinanes. The diastereoselectivity in the crude reaction solution was therefore 94.4:5.6. The mixture was stirred overnight at room temperature (internal temperature of +18–+22° C.) and concentrated the next day on a rotary evaporator at a bath temperature of +40° C. and from 400 to 150 mbar to a final volume of 380 mL to remove methanol, trimethyl borate and some of the toluene. The resulting biphasic mixture was admixed with 212 mL of water at an internal temperature of from +10° C. to +25° C. After stirring had been continued for 5 min, there was a phase separation. The toluene phase was discarded. The yellow, acidic product-containing aqueous phase (approx. 330 mL) was dissolved in 303 mL of 1-butanol and admixed within 10 min with 61.72 g (509.2 mmol, 3.39 equiv.) of 33% sodium hydroxide solution at an internal temperature of from +10° C. to +15° C. in a 1 l four-neck flask equipped with a precision glass stirrer and dropping funnel to obtain an orange-yellow emulsion. Once the addition was complete, the mixture was stirred for a further 5 min. The product-containing, orange-yellow butanol phase (approx. 390 mL, upper) was removed from the virtually colorless clear aqueous phase (lower, approx. pH 9) and concentrated on a rotary evaporator at a bath temperature of +50° C. and from 300 to 50 mbar to such an extent that 115 mL of distillate (1-butanol/water) were azeotropically removed. The resulting concentrated solution of (XIX) in butanol was heated to an internal temperature of +49° C. under nitrogen in a 500 mL four-neck flask equipped with a precision glass stirrer, dropping funnel and internal thermometer and admixed within 5 min via the dropping funnel with 39.24 g (322.9 mmol, 2.15 equiv.) of 30% hydrochloric acid which resulted in an internal temperature rise to +53° C. and a yellow solution. This solution was cooled to an internal temperature of +20° C. within 15 min that resulted in the onset of crystallization of the white dihydrochloride and the formation of a pasty suspension. After a stirring time of 30 min at +20° C., the mixture was cooled to +1° C. within 30 min and stirred at this temperature for a further 1 h. Filtration was then effected through a Büchner funnel to obtain a white filter cake and a yellow filtrate. The filter cake was washed with 2×60 mL of 1-butanol, suction-dried and then dried in a vacuum drying cabinet under a gentle nitrogen stream at 40° C. and 50 mbar. 62.7 g (125.55 mmol) of (XIX)·2 HCl were obtained as a white crystalline solid. According to HPLC, it contained 99.68% of (XIX) and 0.14% of the diastereomer dia-(XIX). The enantiomeric purity was 100% ee. According to titration and $^1$H NMR, (XIX) was present as dihydrochloride. According to $^1$H NMR, 11.5% by weight (corresponding to 87.5 mol %) of 1-butanol were present. The yield was 83.7% of theory when the product weight (62.7 g) is calculated as (XIX)-dihydrochloride neglecting the butanol content and is based on the weight of the reactant (XVII) used without taking into account its incomplete enantiomeric purity (93.4% ee) [known as the telquel yield]. When the butanol content of (XIX)-dihydrochloride is taken into account, and the racemic proportion (6.6%) of the reactant (XVII) used which had been removed in the workup is subtracted, then the yield was 79.4% of theory. When the yield corrected for butanol is based on the all the reactant (XVII), then the yield was 74.1%.

Example 20

Diastereoselective reduction of the optically active free Mannich base (I) [$R^1$ is o-nitrophenyl, $R^2$ is 2-pyridyl, $R^3$ is H, $R^4$ is 2-pyridyl and $R^5$ is phenyl, corresponding to a compound of formula (XVII)] to the enantiomerically pure 1,3-amino alcohol (XIX) with borane generated in situ from chlorotrimethylsilane and sodium borohydride (Table 8, No. 34)

In a 500 mL four-neck round-bottom flask equipped with a precision glass stirrer, reflux condenser, internal thermometer and septum, 1.70 g (45.0 mmol, 3.0 equiv.) of sodium borohydride were suspended in 215 mL of tetrahydrofuran. After adding 4.89 g (45.0 mmol, 3.0 equiv.) of chlorotrimethylsilane (by syringe), the suspension was stirred at average to high speed at an internal temperature of 50° C. for 45 min, and a finely crystalline white solid precipitated out. The suspension was then cooled to +1° C. and admixed within 5 min with 6.36 g (15.0 mmol, 1.0 equiv.) of the Mannich base (XVII), which resulted in an internal temperature rise to +3° C. and a pale yellow suspension. The mixture was heated to 20° C. within 15 min and stirring was continued at this temperature. HPLC monitoring after 30 min indicated virtually complete conversion of (XVII) to the oxazaborinane (C). After a total stirring time of 2 h at 20° C., 25 mL of methanol were added dropwise to the mixture at from 10 to 15° C. within 5 min. 3.1 mL (47.9 mmol, 3.19 equiv.) of methanesulfonic acid were then added within 5 min. The mixture was then stirred further at an internal temperature of 20° C. HPLC monitoring after 15 min showed 23% of (XVII) and 72% of (C). After a stirring time of 30 min, a further 50 mL of methanol and 3.1 mL (47.9 mmol, 3.19 equiv.) of methanesulfonic acid were added to the mixture at 20° C. The mixture was then stirred at an internal temperature of 40–43° C. Further HPLC monitoring after 30 min indicated the complete conversion of (C) to (XIX) (85.1%), dia-(XIX) (5.4%), and also (XVII) and retro-Mannich decomposition products (8.5% in total). After a total stirring time of 1 h at 40–43° C., the yellow suspension was filtered to remove salts and the filtrate fully concentrated on a rotary evaporator at 40° C. and from 400 to 20 mbar. The remaining yellow, viscous oil was stored overnight at +4° C. in 50 mL of water. The aqueous product phase was dissolved in 60 mL of 1-butanol in a 250 mL four-neck round-bottom flask equipped with a precision glass stirrer, dropping funnel and internal thermometer under nitrogen and admixed within 5 min with 11.96 g (98.7 mmol, 6.58 equiv.) of 33% aqueous sodium hydroxide solution at from 15 to 22° C. The orange-yellow suspension was stirred for 5 min and the yellow butanol phase separated from the colorless aqueous phase (pH 13–14). The butanol phase was concentrated at 50° C. and from 200 to 20 mbar to such an extent that 22 mL of distillate (butanol/water) were azeotropically removed. The resulting concentrated butanolic solution was heated to an internal temperature of 47° C. in a 100 mL four-neck flask equipped with a precision glass stirrer, dropping funnel and internal thermometer under nitrogen and admixed within 5 min with 4.00 g (33.0 mmol, 2.20 equiv.) of hydrochloric acid that resulted in an internal temperature rise to 50° C. and a clear orange-red solution. This was cooled to 15° C. within 15 min that resulted in the onset of crystallization of the white dihydrochloride and a pasty suspension being obtained. After a stirring time of 30 min, the mixture was cooled further to 1° C. within 15 min and stirring was continued at this temperature for one hour. The precipitate was filtered off with suction, washed twice with 10 mL of butanol and dried at 40° C. and 50 mbar under a gentle nitrogen stream. 5.60 g (11.21 mmol, 74.8% of theory) of white solid were obtained which, according to HPLC, had >99% ee, and consisted of 99.6% of (XIX) and 0.2% of dia-(XIX). $^1$H NMR indicated a 1-butanol content of 12.0%. The water content (Karl-Fischer titration) was 0.99%. The chloride titration gave 1.97 equiv. of chloride ions per mole of (XIX).

Example 21

Liberation of the Mannich base (I) [$R^1$ is o-nitrophenyl, $R^2$ is 2-pyridyl, $R^3$ is H, $R^4$ is 2-pyridyl and $R^5$ is phenyl, corresponding to a compound of formula (XVII)] from the mandelate salt (XVIII) [Y* is (S)-(+)-mandelic salt] with NaHCO$_3$ in water/acetone according to Table 7, No. 23:

In a 2 liter jacketed reactor (connected to a circulation cryostat) equipped with a temperature sensor and mechanical turbine stirrer, 228.6 g (396.6 mmol, 1.0 equiv.) of mandelate salt (XVIII) (95.6% ee of the Mannich base (XVII) present) were suspended at room temperature in 1143 mL of water under a nitrogen atmosphere and with stirring. The white suspension was then cooled to an internal temperature of +10° C. 66.64 g (793.24 mmol, 2.0 equiv.) of sodium hydrocarbonate were added, followed after 5 min by 114 mL of acetone. The suspension that was gradually becoming yellow was stirred at an internal temperature of +10° C. The conversion was monitored by taking samples, filtration and $^1$H NMR of the solid. After 4.5 hours, 15.4% of mandelic acid were still present, and after 7.4 hours still 9.1%. After stirring overnight, no more mandelic acid was detected. The suspension was filtered off with suction and the filter cake washed 3 times with 50 mL of water each time. The solid was dried in a vacuum drying cabinet at 40° C. and approx. 50 mbar. 168.25 g (396.4 mmol, 99.95% of theory) of the free Mannich base (XVII) were obtained as a yellow powder, 96.8% ee (camph. method according to Example 1) or 96.2% ee (piv. method according to Example 2), m.p. 153–154° C., residual water content according to Karl-Fischer titration: 0.32% by weight. $^1$H NMR and HPLC confirm that it is a single compound that contains no more mandelic acid. $^1$H NMR also showed that the content of the anti-diastereomer of (XVII) was less than 1%.

Example 22

Liberation of the Mannich base (I) [$R^1$ is o-nitrophenyl, $R^2$ is 2-pyridyl, $R^3$ is H, $R^4$ is 2-pyridyl and $R^5$ is phenyl, corresponding to a compound of formula (XVII)] from the mandelate salt (XVIII) [Y* is (S)-(+)-mandelic acid salt] with 2N sodium hydroxide at pH-stat 8.5 in water/ethanol according to Table 7, No. 21

The reaction was carried out in a 10 liter jacketed reactor (connected to a circulation cryostat) equipped with a temperature sensor and mechanical bell stirrer to which a Metrohm 718 STAT-Titrino autotitrator was connected. The autotitrator was filled with 1150 mL of 2.00 N sodium hydroxide solution, and was controlled via a glass electrode dipping into the reaction suspension and set to the following parameters: maximum metering rate 20 mL/min, minimum metering rate 4 mL/min, recording time interval every 60 sec., $pH_{max}$ 8.5. The dropping tip of the autotitrator dipped into the reaction suspension. The jacket temperature of the reactor was controlled in such a manner that the temperature of the reaction suspension was maintained within the 20–25° C. range.

At room temperature, 1311.3 g (2.274 mol, 1.0 equiv.) of mandelate salt (XVIII) (94.4% ee of the Mannich base (XVII) present, approx. 1.3% of the anti-diastereomer of (XVII)) were suspended at room temperature in 5686 mL of water under a nitrogen atmosphere and with stirring, and 569 mL of ethanol (denatured with methyl ethyl ketone) were added. The pH of the suspension (before the beginning of the titration) was 4.8. After switching on the titrator, the pH briefly reached a maximum of pH 9.7. After only 30 sec., the reaction suspension had changed in color from pale yellow to intense yellow. The initially high metering rate slowed appreciably with time. After 4 hours, 92% of the theoretical amount of sodium hydroxide solution had been metered in. The mixture was stirred overnight under pH-stat conditions (pH 8.5). The next morning, the metered addition had come to a standstill. The pH of the suspension was 8.72 and a total of 1139.6 mL (100.2% of theory) had been added by titration. The suspension was filtered off with suction, and the filter cake was washed 4 times with 500 mL of water. The solid was dried in a vacuum drying cabinet under a nitrogen stream at 40° C. and approx. 100 mbar for 28 hours, then at 25° C. and 100 mbar for 70 hours and finally at 40° C. for a further 20 hours under high vacuum ($10^{-2}$ mbar). 960.9 g (2.26 mol, 99.5% of theory) of the free Mannich base (XVII) were obtained as a fine light yellow powder, 95.6% ee (piv. method according to Example 2), m.p. 150–152° C., residual water content according to Karl-Fischer titration: 0.35% by weight. $^1$H NMR and HPLC confirmed that it is a single compound that contains no more mandelic acid. $^1$H NMR also showed that the content of the anti-diastereomer of (XVII) was approx. 1.2%.

Example 23

Diastereoselective reduction of the optically active mandelate salt (III) [$R^1$ is o-nitrophenyl, $R^2$ is 2-pyridyl, $R^3$ is H, $R^4$ is 2-pyridyl and $R^5$ is phenyl, HY* is (S)-(+)-mandelic acid, corresponding to a compound of formula (XVIII)] to the 1,3-amino alcohol (XIX) according to Table 9, No. 18; solvolysis of the oxazaborinane using hydrochloric acid In a 1 l four-neck round-bottom flask equipped with a precision glass stirrer, dropping funnel with fitted bubble counter, internal thermometer and nitrogen feed, 30.0 g (52.0 mmol, 1.0 equiv.) of the mandelate salt (XVIII) (96.5% ee of the Mannich base (XVII) present) were suspended in 400 mL of THF and cooled to +1° C. by means of an ice bath. 15.5 mL (156 mmol, 3.0 equiv.) of borane-dimethyl sulfide complex (95%) were added dropwise within 10 min under a nitrogen atmosphere at a reaction temperature of from +1 to +3° C. Once the addition had been completed, the ice bath was removed and the reaction mixture brought to 23° C. within 15 min, and then stirred for a further 1.5 hours. Sample taking/HPLC analysis showed that the conversion of (XVIII) to oxazaborinane (C) had been completed after only 1 hour. The reaction mixture was cooled again to 1° C. with the ice bath and then 25 mL of water were slowly added dropwise at a maximum internal temperature of 12° C. This resulted in vigorous gas development and the solution became pale yellow. Stirring was continued at room temperature until gas development was complete (30 min). A white solid precipitated out. The THF was distilled out of the reaction mixture at 40° C. and approx. 100 mbar. Toward the end of distillation, a full water-jet vacuum (approx. 20 mbar) was applied for 5 min. After cooling to +5° C., 200 mL (2400 mmol) of conc. hydrochloric acid (37%) were slowly added dropwise at a maximum internal temperature of the reaction mixture of 20° C., and the mixture was then stirred at 40° C. for 1 hour. The 1,3-amino alcohol (XIX) went into solution as the hydrochloride and boric acid precipitated out. The suspension was left to stand overnight in a refrigerator at 4° C. in order to complete the crystallization. The boric acid was filtered off with suction and washed with 40 mL of water. After drying under reduced pressure, it weighed 7.23 g (116.9 mmol, 75% of theory). The acidic filtrate had a total volume of 250 mL. In a 1 l four-neck flask equipped with a precision glass stirrer and dropping funnel, 96 g (2400 mmol) of sodium hydroxide solution were dissolved in 520 mL of water, cooled to 13° C., and then said acidic filtrate was slowly added dropwise within 60 min at a maximum internal temperature of 15° C. The crude 1,3-amino alcohol (XIX) precipitated out in roughly crystalline form. The suspension was stirred at room temperature for a further 1 hour, and the precipitate was filtered off with suction and washed with 250 mL of water (the precipitate which formed when the washing water ran into the filtrate consisted predominantly of polar impurities and was therefore discarded). The crude (XIX) was dried in a vacuum drying cabinet at 40° C. and approx. 100 mbar. 20.7 g (48.54 mmol, 93.4% of theory) of pale yellow solid was obtained. It was suspended in 100 mL of diisopropyl ether and stirred vigorously at 55° C. for 1 hour. The solid was filtered off with suction, washed with 100 mL of diisopropyl ether and dried under reduced pressure at 40° C. and approx. 100 mbar. 17.5 g (41.0 mmol, 78.9% of theory) of pale yellow powder were obtained that, according to HPLC analysis, was 95% pure and contained 3.1% of the diastereomer dia-(XIX) and 1.8% of by-products.

Example 24

Diastereoselective reduction of an optically active mannich salt (III) [$R^1$ is o-nitrophenyl, $R^2$ is 2-pyridyl, $R^3$ is H, $R^4$ is 2-pyridyl, $R^5$ is phenyl and HY* is (+)-DPTA] to the 1,3-amino alcohol of the general formula (II), corresponding to a compound of formula (XIX) according to Table 10, No. 5; solvolysis of the oxazaborinane with hydrochloric acid.

In a 250 mL four-neck round-bottom flask equipped with a precision glass stirrer, septum, bubble counter, internal thermometer and nitrogen feed, 10.0 g (8.57 mmol; according to $^1$H NMR determination of the ratio of the compound (XVII) to DPTA, containing 16.08 mmol of (XVII); 1.0 equiv.) of the DPTA salt (III) (95.1% ee of the Mannich base (XVII) present) were suspended in 100 mL of THF, then cooled to an internal temperature of from 0 to 5° C. 7.63 mL (80.45 mmol, 5.0 equiv.) of borane-dimethyl sulfide complex (95%) were added dropwise within 15 min by syringe under nitrogen. The ice bath was then removed and the suspension heated to room temperature. After 20 min at room temperature, there was a clear solution. Taking a sample and HPLC analysis showed that (III) had been quantitatively converted to the oxazaborinane (C) and that only a few by-products had been formed. 45 mL of water were added dropwise within 15 min (gas development, vigorous foaming), which resulted in an internal temperature rise to 40° C. 10 mL of 37% hydrochloric acid were added dropwise within 15 min, and then the internal temperature was increased to 60° C. After 15 min at 60° C., HPLC analysis indicated that no more boron compound was present and that (XIX) had formed as the main product. 30 mL of 33% sodium hydroxide solution were used to adjust the pH to 13, and the reaction mixture was then cooled to room temperature and extracted twice with 100 mL of dichloromethane. The combined organic extracts were evaporated to dryness under reduced pressure and the residue (solid foam) was dried in a vacuum drying cabinet at 40° C. and 50 mbar. 8.11 g of pale yellow powder were obtained which, according to an HPLC assay, had a purity of 75.1%, based on a pure reference standard of (XIX). The yield of (XIX) was therefore 6.09 g (14.28 mmol, 88.8% of theory). The HPLC 100% purity was 94.8%, the ratio of (XIX) to dia-(XIX) was 97.8:2.2, and the enantiomeric purity was 96.8% ee.

Example 25

Diastereoselective reduction of an optically active Mannich salt (III) [$R^1$ is o-nitrophenyl, $R^2$ is 2-pyridyl, $R^3$ is H, $R^4$ is 2-pyridyl, $R^5$ is phenyl and HY* is (+)-DPTA] to the 1,3-amino alcohol of the general formula (II), corresponding to a compound of formula (XIX) according to Table 10, No. 3; solvolysis of the oxazaborinane using potassium hydroxide solution In a 250 mL four-neck round-bottom flask equipped with a precision glass stirrer, septum, bubble counter, internal thermometer and nitrogen feed, 10.0 g (8.57 mmol; according to $^1$H NMR determination of the ratio of the compound (XVII) to DPTA, containing 16.08 mmol of (XVII); 1.0 equiv.) of the DPTA salt (III) (95.1% ee of the Mannich base (XVII) present) were suspended in 100 mL of THF, then cooled to an internal temperature of from 0 to 5° C. 7.63 mL (80.45 mmol, 5.0 equiv.) of borane-dimethyl sulfide complex (95%) were added dropwise within 15 min by syringe under nitrogen. The ice bath was removed and the reaction mixture stirred while heating to room temperature. After 30 min, there was a clear solution. Taking a sample and HPLC analysis showed the complete conversion of the reactant to 91% of oxazaborinane and 9% of (XIX). 45 mL of water were added dropwise within 15 min, followed by 45 mL of 20% aqueous potassium hydroxide solution within 15 min. This resulted in gas development, vigorous foaming and an internal temperature rise to 40° C. The reaction mixture was heated to 60° C. and the solvolysis of the oxazaborinane to the 1,3-amino alcohol (XIX) was followed by HPLC monitoring. After 3 hours at 60° C., the ratio (C)/(XIX) was 53.3:46.7, after 10 hours 19.4:80.6, and after 16 hours 6.9:93.1. The solvolysis was aborted at this point and the reaction mixture cooled to room temperature. Extraction was effected twice with 100 mL of dichloromethane and the combined organic extracts were washed with 50 mL of saturated sodium chloride solution. The dichloromethane solution was then evaporated to dryness under reduced pressure and the residue was dried under reduced pressure at 40° C. and 50 mbar. 7.05 g of pale yellow powder were obtained which, according to an HPLC assay, had a purity of 77.2% based on a pure reference standard of (XIX). The yield of (XIX) was therefore 5.44 g (12.76 mmol, 79.3% of theory). The HPLC 100% purity was 93.0%, the ratio of (XIX)/dia-(XIX) 98.5:1.5, and the enantiomeric purity 95.2% ee. 5.5% of unsolvolyzed oxazaborinane (C) were still present.

Example 26

Diastereoselective reduction of an optically active Mannich salt (III) [$R^1$ is o-nitrophenyl, $R^2$ is 2-pyridyl, $R^3$ is H, $R^4$ is 2-pyridyl, $R^5$ is phenyl and HY* is (+)-DPTA] to the 1,3-amino alcohol of the general formula (II), corresponding to a compound of formula (XIX) according to Table 10, No. 9; solvolysis of the oxazaborinane using methanol/methanesulfonic acid In a 250 mL four-neck round-bottom flask equipped with a precision glass stirrer, septum, bubble counter, internal thermometer and nitrogen feed, 15.33 g (13.13 mmol; according to $^1$H NMR determination of the ratio of the compound (XVII) to DPTA, containing 25.30 mmol of (XVII); 1.0 equiv.) of the DPTA salt (III) (93.2% ee of the Mannich base (XVII) present) were suspended in 125 mL of THF, then cooled to an internal temperature of from 0 to 5° C. 4.86 mL (63.94 mmol, 2.5 equiv.) of borane-dimethyl sulfide complex (95%) were added dropwise within 15 min by syringe under nitrogen. The ice bath was removed and the reaction mixture stirred while heating to room temperature. After 45 min, there was a clear solution. After 2 h, no more reactant could be detected by HPLC. At 5° C., 20.9 g of methanol were added dropwise within 15 min, immediately followed by 4.92 g of methanesulfonic acid. The yellow solution was heated to an internal temperature of 35° C. and the solvolysis of the oxazaborinane (C) was followed by HPLC monitoring. After 4.5 h, 3.7% of (C), 94.2% of (XIX) and 2.1% of the diastereomer dia-(XIX) were detected. After 6.5 h at 35° C. and standing of the solution overnight at room temperature, 1.8% of (C), 96.9% of (XIX) and 1.8% of dia-(XIX) were detected. The yellow, clear solution was evaporated under reduced pressure on a rotary evaporator to a residue of 22.95 g (yellow oil plus solid) and dissolved in 15 mL of methanol to give a clear solution (ultrasound bath, 35° C.). This highly concentrated methanol solution was added dropwise within 15 min into the solution of 10 mL of 25% ammonia solution in 75 mL of water (25° C.), and (XIX) precipitated out immediately. The suspension was stirred at room temperature for 1 hour, then filtered off with suction. According to an HPLC assay against a pure reference standard of (XIX), this crude product had a purity of 88% and a (XIX)/dia-(XIX) ratio of 98.1:1.9. It was resuspended in a solution of 1 mL of conc. ammonia solution in 75 mL of water and stirred vigorously at room temperature for two hours, then filtered off with suction and dried at 45° C. and 150 mbar. 11.0 g (25.79 mmol, 101.9% of theory) of a light yellow powder that, according to an HPLC assay against a standard, had a purity of 96.1% (i.e., corrected yield: 97.9% of theory), 93.2% ee and an unchanged (XIX)/dia-(XIX) ratio of 98.1:1.9. This roughly purified (XIX) was stirred vigorously in 66 mL of boiling diisopropyl ether for 30 min, stirred for a further hour under ice bath cooling, then filtered off with suction and dried at 50° C. under high vacuum ($10^{-2}$ mbar). 9.50 g (22.28 mmol, 88.1% of theory) of light yellow powder were obtained which, according to an HPLC assay against a standard, had 97.9% purity (i.e., corrected yield: 86.2% of theory), 95.2% ee and an (XIX)/dia-(XIX) ratio of 99.2:0.8.

Example 27

Synthesis of the optically active Mannich salt of formula (III) [$R^1$ is p-tolyl, $R^2$ is 2-pyridyl, $R^3$ is H, $R^4$ is 2-pyridyl and $R^5$ is phenyl] by four-component coupling with dynamic optical resolution at room temperature; use of (S)-(+)-mandelic acid as the chiral auxiliary [HY* is (+)-MDLA)] and ethanol as the solvent:

In a 100 mL three-neck flask equipped with a precision glass stirrer, 30 mL of ethanol (denatured with methyl ethyl ketone) were initially charged. At room temperature (22° C.), 2.32 g (11.76 mmol, 1.00 equiv.) of 2-pyridylmethyl phenyl ketone, 1.40 g (14.70 mmol, 1.25 equiv.) of 2-aminopyridine, 1.75 g (14.11 mmol, 1.20 equiv.) of 4-tolylaldehyde and 3.65 g (23.52 mmol, 2.00 equiv.) of (S)-(+)-mandelic acid were added in succession under an $N_2$ atmosphere. The mechanical stirrer was switched on and after a few minutes a clear yellow solution formed. After 1 h, considerable amounts of precipitate had formed. The suspension was stirred further at room temperature. After 40 h and 64 h of reaction time, samples of the suspension (each containing approx. 50 mg of precipitate) were withdrawn and the precipitate in it filtered off with suction in each case. The syn/anti ratio was determined by $^1$H NMR spectroscopy (measured immediately after dissolving the sample in DMSO-d6). The diastereomeric ratio can in principle be calculated from the integrals of a plurality of signals, most simply from the methyl singlet that for the syn-isomer is at δ is 2.15 ppm, and for the antiisomer at δ is 2.11 ppm. The optical purity of the Mannich base was determined by chiral phase HPLC analysis after piv. derivatization using the procedure described at the end of Example 27.

For both samples, the syn/anti ratio calculated from the NMR integrals was 95:5. Taking into account the period of 3.5 min that was required after dissolving the sample for introducing the sample into the NMR instrument, sample shimming and data accumulation, an original syn/anti ratio of the precipitate of >99:<1 is extrapolated from the kinetics (Example 28) of the syn/anti-isomerization. In both cases, the molar ratio of Mannich base to mandelic acid was exactly 1:1. The enantiomeric excess of the Mannich base was 96.0% ee in the sample after 40 h and 97.0% ee in the sample after 64 h.

The precipitate of the reaction mixture was filtered off with suction, washed with mother liquor and then with a little ethanol, suction-dried and dried under high vacuum. 5.66 g (10.4 mmol, 88.2% of theory) of pale yellow powder were obtained. Taking into account the two samples taken previously (approx. 100 mg), the yield was 90% of theory.

$^1$H NMR (400 MHz, DMSO-d$^6$): δ is 2.15 (s, 3H), 5.02 (s, 1H, CHOH of the mandelate anion), 5.65 (d, 1H), 5.95 (t, 1H), 6.32 (d, 1H), 6.37 (t, 1H), 6.89 (d, 1H), 699 (d, 2H), 7.20 (m, 2H), 7.25–7.48 (m, 11H), 7.50–7.60 (m, 2H), 7.68 (td, 1H), 7.87 (d, 2H), 7.92 (~d, 1H), 8.46 (~d, 1H).

$^{13}$C NMR (100.62 MHz, DMSO-d$^6$): δ is 20.52 (CH$_3$), 55.20 (CH), 60.55 (CH), 72.44 (CHOH of the mandelate anion), 107.84 (CH), 111.87 (CH), 119.10 (CH), 121.80 (CH), 126.60–128.70 (12 signals, CH), 133.13 (CH), 135.40 (C), 136.50 (CH), 136.63 (CH), 138.95 (C), 140.20 (C), 147.25 (CH), 148.87 (CH), 156.10 (C), 157.90 (C), 174.20 (CO$_2$—), 196.8 (C is O).

Derivatization and ee Determination:

20 μL of pivaloyl chloride, followed by 10 μL of triethylamine are added to 2–5 mg of the Mannich salt in a Reacti-Vial. The solution is sonicated for 2 min in an ultrasound bath. 500 μL of acetonitrile (HPLC grade) are added and 1 μL of the solution is injected onto a Chiralpak AS 250 mm×4.6 mm column. Isocratic elution at 25° C. and 1.0 mL/min of the eluent 50% isopropanol/50% n-hexane/0.1% trifluoroacetic acid and UV detection at 254 nm. The main isomer (98.5%) was eluted at t(ret) 12.14 min, and the mirror image (1.5%) at t(ret) 7.34 min. An appropriately derivatized racemic comparative sample delivered 50% of each peak.

Example 28

Syn/anti-isomerization of the Mannich base mandelate from Example 26 in DMSO-d$^6$ solution at 300K. Kinetics and equilibrium location of the retro-Mannich/Mannich reactions:

8 mg of the product from Example 27 were dissolved in DMSO-d$^6$ as rapidly as possible in a $^1$H NMR tube at room temperature. The sample was immediately introduced into the NMR instrument (400 MHz, 300.0 K), shimmed rapidly and analyzed. The first spectrum was obtained 3.5 min after the sample dissolution. It showed the syn- and anti-isomers of the Mannich salt in a ratio of 95.1:4.9. Further spectra of the solution were each obtained at an interval of 3–4 min. They showed a continuous increase of the anti-isomer at the expense of the syn-isomer. The variation can be seen from the graphics and the table of the appendix. 69 min after dissolution of the Mannich salt, the NMR monitoring was aborted at a syn/anti ratio of 50:50. A repeat measurement 20.5 hours after dissolution of the Mannich salt indicated a syn/anti ratio of 41.5:58.5. After a total of 44.5 hours, this ratio was unchanged. The thermodynamic equilibrium of the two isomers is thus achieved in less than 20 h and the anti-isomer is preferred in solution. In contrast, the four-component coupling (Example 27) results in the crystallization of virtually pure syn-isomer, apparently owing to lower solubility. Even the spectrum obtained 3.5 min after sample dissolution indicates (in addition to the syn- and anti-isomers of the Mannich salt) the presence of the retro-Mannich products 2-pyridylmethyl phenyl ketone (formula VI; singlet at δ is 4.53 ppm) and tolylaldehyde (or corresponding imine) (formula IV or X, singlets at δ is 2.40 and 9.12 ppm) in small but significant amounts. The best fitting curve between the measurement points of the graph was obtained by 3rd order polynomial formation. Extrapolation of these curves to time t is 0 shows that the solid had a syn/anti ratio of >99:<1.

| NMR Measurment No. | Time afer sample dissolution [min] | cis-isomer [%] | trans-isomer [%] |
|---|---|---|---|
| 1 | 3.5 | 95.1 | 4.9 |
| 2 | 6.5 | 92.5 | 7.5 |
| 3 | 10.5 | 89.0 | 11.0 |
| 4 | 13.5 | 85.0 | 15.0 |
| 5 | 17.5 | 81.7 | 18.3 |
| 6 | 20.5 | 77.3 | 22.7 |
| 7 | 24.5 | 76.8 | 23.2 |
| 8 | 27.5 | 71.8 | 28.2 |
| 9 | 31.5 | 68.0 | 32.0 |
| 10 | 34.5 | 66.2 | 33.8 |
| 11 | 37.5 | 63.8 | 36.2 |
| 12 | 41.5 | 61.7 | 38.3 |
| 13 | 44.5 | 60.1 | 39.9 |
| 14 | 48.5 | 58.7 | 41.3 |
| 15 | 51.5 | 56.8 | 43.2 |
| 16 | 55.5 | 54.5 | 45.5 |
| 17 | 58.5 | 53.6 | 46.4 |
| 18 | 61.5 | 52.9 | 47.1 |
| 19 | 65.5 | 52.0 | 48.0 |
| 20 | 68.5 | 50.5 | 49.5 |
| 21 | 1230 | 41.5 | 58.5 |
| 22 | 2670 | 41.6 | 58.4 |

Example 29

Synthesis of the optically active Mannich salt of formula (III) [$R^1$ is o-chlorophenyl, $R^2$ is 2-pyridyl, $R^3$ is H, $R^4$ is 2-pyridyl and $R^5$ is phenyl] by four-component coupling with dynamic optical resolution at room temperature; use of (S)-(+)-mandelic acid as the chiral auxiliary [HY* is (+)-MDLA)] and ethanol as the solvent:

In a 50 mL two-neck flask equipped with a magnetic stirrer bar, 30 mL of ethanol (denatured with methyl ethyl ketone) were initially charged. At room temperature (20° C.), 2.32 g (11.76 mmol, 1.00 equiv.) of 2-pyridylmethyl phenyl ketone, 1.41 g (14.70 mmol, 1.25 equiv.) of 2-aminopyridine, 2.03 g (14.11 mmol, 1.20 equiv.) of 2-chlorobenzaldehyde and 3.65 g (23.52 mmol, 2.00 equiv.) of (S)-(+)-mandelic acid were added in succession under an $N_2$ atmosphere. The magnetic stirrer was switched on and a yellow, slightly cloudy solution formed. After a reaction time of 30 min, the cloudiness had distinctly increased, and after 1 h, considerable amounts of precipitate had already appeared. The mixture was stirred at room temperature over the weekend. After a total of 3, 4, 5, 6 and 7 days of reaction time, samples (each of approx. 50 mg) were taken. Derivatization with pivaloyl chloride and similar HPLC analysis to Example 27 gave the following enantiomeric excesses: 97.2% ee, 97.4% ee, 97.6% ee, 98.2% ee, 98.4% ee. The main isomer was eluted at t(ret) is 9.38 min, and the mirror image at t(ret) is 6.31 min. An appropriately derivatized racemic comparative sample delivered 50% of each of these peaks.

In $^1$H NMR spectra (400 MHz, DMSO-d$^6$) of the samples, the anti-isomer could not be detected (i.e., syn/anti>>99:1), and likewise no o-chlorobenzaldehyde or its imine. Traces of the retro-Mannich product 2-pyridylmethyl phenyl ketone could be detected. The precipitate of the reaction batch was filtered off with suction, washed with mother liquor and then with a little ethanol, suction-dried and dried under high vacuum. 5.77 g (10.19 mmol, 86.7% of theory) of pale yellow powder were obtained. Taking into account the five previously taken samples (approx. 250 mg), the isolated yield was 90.4% of theory.

$^1$H NMR (400 MHz, DMSO-d$^6$): δ is 5.02 (s, 1H, C$\underline{H}$OH of the mandelate anion), 5.73 (d, 1H), 6.22 (t, 1H), 6.38 (d, 1H), 6.40 (t, 1H), 6.90 (d, 1H), 7.14 (t, 2H), 7.18 (~td, 1H), 7.25–7.30 (m, 2H), 7.30–7.38 (m, 3H), 7.38–7.45 (m, 4H), 7.45–7.57 (m, 3H), 7.67 (td, 1H), 7.87 (m, 3H), 8.48 (dd, 1H).

$^{13}$C NMR (100,62 MHz, DMSO-d$^6$): δ is 52.65 (CH), 58.92 (CH), 72.41 (CHOH of the mandelate anion), 107.37 (CH), 112.25 (CH), 122.35 (CH), 124.66 (CH), 126.60–129.29 (9 signals, CH), 132.83 (CH), 133.02 (C), 136.30 (C), 136.71 (CH), 136.77 (CH), 139.68 (C), 140.22 (C), 147.37 (CH), 148.90 (CH), 156.36 (C), 157.44 (C), 174.09 ($CO_2$—),196.43 (CisO).

Example 30

Synthesis of the racemic Mannich salt of formula (III) [$R^1$ is phenyl, $R^2$ is 2-pyridyl, $R^3$ is H, $R^4$ is 2-pyridyl and $R^5$ is phenyl] by four-component coupling at room temperature; use of (S)-(+)-mandelic acid as the chiral auxiliary [HY* is (+)-MDLA)] and ethanol as the solvent:

In a 100 mL three-neck flask equipped with a precision glass stirrer, 30 mL of ethanol (denatured with methyl ethyl ketone) were initially charged. At room temperature (22° C.), 2.32 g (11.76 mmol, 1.00 equiv.) of 2-pyridylmethyl phenyl ketone, 1.41 g (14.70 mmol, 1.25 equiv.) of 2-aminopyridine, 1.51 g (14.11 mmol, 1.20 equiv.) of benzaldehyde and 3.65 g (23.52 mmol, 2.00 equiv.) of (S)-(+)-mandelic acid were added in succession under an $N_2$ atmosphere. The mechanical stirrer was switched on and after a few minutes a yellow, slightly cloudy solution formed. After 20 min, a precipitate had formed. The suspension was stirred further at room temperature for 3 days. A sample was taken in a similar manner to Example 27 and derivatized with pivaloyl chloride. The analysis was effected isocratically on a Chiralpak AD 250 mm×4.6 mm column using a 25% isopropanol/75% n-hexane/0.1% trifluoroacetic acid eluent. The enamtiomers, as in an appropriately derivatized racemic reference sample, were eluted in a 50:50 ratio [t(ret) is 12.25 and 14.46 min]. $^1$H NMR showed that the Mannich mandelate salt was present in high purity. Diastereomer and retro-Mannich products could be detected in very small amounts in the NMR solution (DMSO-d$^6$).

The reaction mixture was then heated to 60° C. for 7 h, then allowed to cool to RT, and the solid was filtered off, washed with a little ethanol and dried under high vacuum. 5.55 g (10.44 mmol; 88.8% of theory) of pale yellow powder was obtained. The $^1$H NMR spectrum was unchanged. Derivatization resulted in the Mannich base remaining unchanged in racemic form. In contrast to Examples 27 and 29, (S)-(+)-mandelic acid in an ethanol solvent does effect formation of the Mannich base from the reactants (IV), (V) and (VI), and also crystallization of the mandelate salt, but no dynamic optical resolution.

$^1$H NMR (400 MHz, DMSO-d$^6$): δ is 5.02 (s, 1H, C$\underline{H}$OH of the mandelate anion), 5.68 (d, 1H), 5.99 (t, 1H), 6.32 (d, 1H), 6.37 (t, 1H), 6.97 (d, 1H), 7.07 (t, 1H), 7.15–7.25 (m, 5H), 7.41 (t, 2H), 7.50–7.60 (m, 3H), 7.70 (t, 1H), 7.87 (d+m, 3H), 8.47 (d, 1H).

We claim:

1. A process for preparing a compound of formula (III) or its diastereoisomer

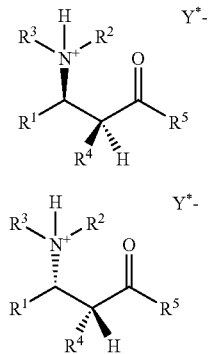

wherein
R$^1$ is hydrogen;
    tert-butyl; or
    aryl or heteroaryl;
R$^2$, R$^3$ and R$^4$ are each, independently,
    hydrogen;
    (C$_1$–C$_7$)alkyl, optionally substituted by aryl;
    (C$_3$–C$_7$)cycloalkyl; or aryl or heteroaryl;
R$_5$ is aryl or heteroaryl;
and
Y*$^-$ is the conjugated base of an optically active, organic Brønsted acid,
provided that R$^1$ and R$^4$ are not concurrently present as hydrogen,
comprising
reacting compounds of formulae (IV), (V), (VI) and (VII)

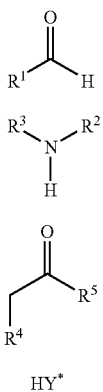

wherein R$^1$, R$^2$, R$^3$, R$^4$ and R$^5$ are as defined in the present claim, and HY* is the optically active, organic Brønsted acid, without a solvent or in one or more suitable solvents,
(i) simultaneously in a direct Mannich reaction, or
(ii) sequentially wherein initially the compounds of formulae (IV) and (V) are reacted to give an imine of formula (X) or an aminal of formula (XI), either of which is optionally isolated,

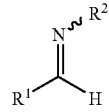

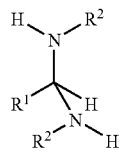

and then reacting the compound of formula (X) or (XI) with the compounds of formula (VI) and (VII).

2. The process according to claim 1, wherein the optically active, organic Brønsted acid is an optically active, carboxylic acid.

3. The process according to claim 1, wherein the optically active, organic Brønsted acid is an acid selected from the group consisting of (R)-(−)-mandelic acid, (S)-(+)-mandelic acid, D-(−)-tartaric acid, L-(+)-tartaric acid, (+)-di-O,O′-pivaloyl-D-tartaric acid (−)-di-O,O′-pivaloyl-L-tartaric acid, (+)-O-O′-dibenzoyl-D-tartaric acid, (−)-O-O′-dibenzoyl-L-tartaric acid, (−)-di-O,O′-benzoyl-L-tartaric mono(dimethylamide), (+)-O,O′-dianisoyl-D-tartaric acid, (−)-O,O′-dianisoyl-L-tartaric acid, (+)-di-O,O′-p-tolyl-D-tartaric acid, (−)-di-O,O′-p-tolyl-L-tartaric acid, D-(+)-malic acid, L-(−)-malic acid, L-(+)-lactic acid, D-(−)-lactic acid, (S)-(−)-2-(phenylaminocarbonyloxy)propionic acid, (R)-(+)-2-(phenylaminocarbonyloxy)propionic acid, D-(+)-gluconic acid, (−)-2,3,4,6-di-O-isopropylidene-2-keto-L-gulonic acid, (D)-(−)-quinic acid, (−)-3,4,5-trihydroxy-1-cyclohexene-1-carboxylic acid, (S)-(+)-(2,2-dimethyl-5-oxodioxolan-4-yl)acetic acid, (+)-camphoric acid, (−)-camphoric acid, (1R)-(+)-camphanic acid, (1S)-(−)-camphanic acid, (R)-(−)-O-acetylmandelic acid, (S)-(+)-O-acetylmandelic acid, (R)-2-phenoxypropionic acid, (S)-2-phenoxypropionic acid, (S)-(+)-α-methoxyphenylacetic acid, (R)-(−)-α-methoxyphenylacetic acid, (R)-(+)-α-methoxy-α-trifluoromethylphenylacetic acid, (S)-(−)-α-methoxy-α-trifluoromethylphenylacetic acid, (S)-(+)-2-phenylpropionic acid, (R)-(−)-2-phenylpropionic acid, (R)-(+)-2-chloropropionic acid, (S)-(−)-2-chloropropionic acid, (R)-(+)-N-(α-methylbenzyl)phthalic monoamide, (S)-(−)-N-(α-methylbenzyl)phthalic monoamide, (R)-(−)-5-oxotetrahydrofuran-2-carboxylic acid, (S)-(+)-5-oxotetrahydrofuran-2-carboxylic acid, D-(+)-3-phenyllactic acid, L-(−)-3-phenyllactic acid, L-(+)-α-hydroxyisovaleric acid, D-(−)-α-hydroxyisovaleric acid, (+)-menthyloxyacetic acid, (−)-menthyloxyacetic acid, (+)-mono-(1S)-menthyl phthalate, (−)-mono-(1R)-menthyl phthalate, (+)-trans-5-norbornene-2,3-dicarboxylic acid, (−)-trans-5-norbornene-2,3-dicarboxylic acid, (R)-(+)-methylsuccinic acid, (S)-(−)-methylsuccinic acid, (R)-(+)-6-hydroxy-2,5,7,8-tetramethylchroman-2-carboxylic acid, (S)-(−)-6-hydroxy-2,5,7,8-tetramethylchroman-2-carboxylic acid, (S)-(+)-2-(4-isobutylphenyl)propionic acid, (R)-(−)-2-(4-isobutylphenyl)propionic acid, (+)-2-(6-methoxy-2-naphthyl)propionic acid, (−)-2-(6-methoxy-2-naphthyl)propionic acid, a natural or unnatural α- or β-amino acid and an N-acylated derivatives of the natural or unnatural α- or β-amino acid.

4. The process according to claim 1, wherein the optically active, organic Brønsted acid is an optically active sulfonic acid.

5. The process according to claim 1, wherein the optically active, organic Brønsted acid is an acid selected from the group consisting of (1S)-(+)-camphor-10-sulfonic acid, (1R)-(−)-camphor-10-sulfonic acid, (−)-3-bromocamphor-8-sulfonic acid and (+)-3-bromocamphor-10-sulfonic acid.

6. The process according to claim 1, wherein the optically active, organic Brønsted acid is an optically active phosphoric acid derivative, an optically active phosphinic acid derivative or an optically active phosphonic acid derivative.

7. The process according to claim 1, wherein the optically active, organic Brønsted acid is an acid selected from the group consisting of (R)-(−)-1,1'-binaphthalene-2,2'-diyl hydrogenphosphate, (S)-(+)-1,1'-binaphthalene-2,2'-diyl hydrogenphosphate, (+)-phosphinothricin and (−)-phosphinothricin.

8. The process according to claim 1, wherein the optically active, organic Brønsted acid is an optically active phenol.

9. The process according to claim 1, wherein the optically active, organic Brønsted acid is (R)-(+)- or (S)-(−)-binaphthol.

10. The process according to claim 1, wherein the optically active, organic Brønsted acid is an acid selected from the group consisting of (R)-(−)-mandelic acid, (S)-(+)-mandelic acid, D-(−)-tartaric acid, L-(+)-tartaric acid, (+)-di-O-O'-pivaloyl-D-tartaric acid, (−)-di-O,O'-pivaloyl-L-tartaric acid, (+)-O,O'-dibenzoyl-D-tartaric acid, (−)-O,O'-dibenzoyl-L-tartaric acid, (−)-di-O,O'-benzoyl-L-tartaric mono (dimethylamide), (+)-O,O'-dianisoyl-D-tartaric acid, (−)-O,O'-dianisoyl-L-tartaric acid, (+)-O,O'-p-tolyl-D-tartaric acid, (−)-di-O,O'-p-tolyl-L-tartaric acid, D-(+)-malic acid, L-(−)-malic acid, L-(+)-lactic acid, D-(−)-lactic acid, (S)-(−)-2-(phenylaminocarbonyloxy)propionic acid, (R)-(+)-2-(phenylaminocarbonyloxy)propionic acid, D-(+)-gluconic acid, (−)-2,3,4,6-di-O-isopropylidene-2-keto-L-gulonic acid, (D)-(−)-quinic acid, (−)-3,4,5-trihydroxy-1-cyclohexene-1-carboxylic acid, (S)-(+)-(2,2-dimethyl-5-oxodioxolan-4-yl)acetic acid, (+)-camphoric acid, (−)-camphoric acid, (1R)-(+)-camphanic acid, (1S)-(−)-camphanic acid, (R)-(−)-O-acetylmandelic acid, (S)-(+)-O-acetylmandelic acid, (R)-2-phenoxypropionic acid, (S)-2-phenoxypropionic acid, (S)-(+)-α-methylphenylacetic acid, (R)-(−)-α-methoxyphenylacetic acid, (R)-(+)-α-methoxy-α-trifluoromethylphenylacetic acid, (S)-(−)-α-methoxy-α-trifluoromethylphenylacetic acid, (S)-(+)-2-phenylpropionic acid, (R)-(−)-2-phenylpropionic acid, (R)-(+)-2-chloropropionic acid, (S)-(−)-2-chloropropionic acid, (R)-(+)-N-(α-methylbenzyl) phthalic monoamide, (S)-(−)-N-(α-methylbenzyl)phthalic monoamide, (R)-(−)-5-oxotetrahydrofuran-2-carboxylic acid, (S)-(+)-5-oxotetrahydrofuran-2-carboxylic acid, D-(+)-3-phenyllactic acid, L-(−)-3-phenyllactic acid, L-(+)-α-hydroxyisovaleric acid, D-(−)-α-hydroxyisovaleric acid, (+)-methyloxyacetic acid, (−)-methyloxyacetic acid, (+)-mono-(1S)-methyl phthalate, (−)-mono-(1R)-menthyl phthalate, (+)-trans-5-norbornene-2,3-dicarboxylic acid, (−)-trans-5-norbornene-2,3-dicarboxylic acid, (R)-(+)-methylsuccinic acid, (S)-(−)-methylsuccinic acid, (R)-(+)-6-hydroxy-2,5,7,8-tetramethylchroman-2-carboxylic acid, (S)-(−)-6-hydroxy-2,5,7,8-tetramethylchroman-2-carboxylic acid, (S)-(+)-2-(4-isobutylphenyl)propionic acid (R)-(−)-2-(4-isobutylphenyl)propionic acid, (+)-2-(6-methoxy-2-naphthyl)propionic acid, (−)-2-(6-methoxy-2-naphthyl)propionic acid, and a natural or unnatural α- or β-amino acid.

11. The process according to claim 1, wherein the compound of formulae (III) or (IIIA) has an enantioneric purity of equal or greater than 95% ee.

12. The process according to claim 1, wherein the compound of formulae (III) or (IIIA) has an enantioneric purity of equal or greater than 98% ee.

13. The process according to claim 1, wherein $R^1$ is tert-butyl; or
   aryl or heteroaryl; and
$R^4$ is $(C_1–C_7)$alkyl, optionally substituted by aryl;
   $(C_3–C_7)$cycloalkyl; or
   aryl or heteroaryl.

* * * * *